United States Patent
Guarino et al.

(12) 
(10) Patent No.: US 6,511,832 B1
(45) Date of Patent: Jan. 28, 2003

(54) IN VITRO SYNTHESIS OF CAPPED AND POLYADENYLATED MRNAS USING BACULOVIRUS RNA POLYMERASE

(75) Inventors: Linda A. Guarino; Wen Dong; Jianping Jin, all of College Station, TX (US)

(73) Assignee: Texas A&M University System, College Station, TX (US)

( * ) Notice: Subject to any disclaimer, the term of this patent is extended or adjusted under 35 U.S.C. 154(b) by 3 days.

(21) Appl. No.: 09/684,854

(22) Filed: Oct. 6, 2000

Related U.S. Application Data

(60) Provisional application No. 60/157,921, filed on Oct. 6, 1999.

(51) Int. Cl.[7] ................................................. C12Q 1/68
(52) U.S. Cl. .............................. 435/91.1; 435/5; 435/6; 435/91.2; 435/69.1; 935/69; 935/70; 935/71
(58) Field of Search ............................... 435/5, 6, 91.1, 435/91.2, 69.1; 935/69, 70, 71

(56) References Cited

U.S. PATENT DOCUMENTS 5,460,950 A * 10/1995 Barr et al. .................. 435/69.1

OTHER PUBLICATIONS

Ambion, MmESSAGE MmACHINE—Background and Brief Protocol, Version 9703, pp. 1–2.
Farfan, Abigail, "Ribo ma7G Cap Analog", Technically Speaking—Q&A, p. 23.
McCracken, S, et al, "The C-terminal domain of RNA polymerase II couples mRNA processing to transcription", Nature vol. 385, Jan. 23, 1997; 357–361.
Gross, C and Stewart Shuman, "RNA 5'-riphosphatase, Nucleoside Triphosphatase, and Guanylytransferase Activities of Baculovirus LEF–4 Protein", Journal of Virology, vol. 72, No. 12, Dec. 1998, 10020–10028.
Jiaping, Jin, et al, "The Lef–4 Subunit of Baculovirus RNA Polymerase Has RNA 5'–Triphosphatase and ATPase Activities", Journal of Virology, Vol. 72, No. 12, Dec. 1998, 10011–10019.
Jiaping, Jin, et al, "3'–End Formation of Baculovirus Late RNAs", Journal of Virology, vol. 74, No. 19, Oct. 2000, 8930–8937.
Guarino, L, et al. "Guanylytransferase Activity of the LEF–4 Subunit of Baculovirus RNA Polymerase", Journal of Virology, vol. 72, No. 12, Dec. 1998, 10003–10010.
Guarino, L, et al. "A Virus–Encoded RNA Polymerase Purified from Baculovirus–Infected Cells", Journal of Virology, vol. 72, No. 10, Oct. 1998, 7985–7991.
Mizuguchi, Hiroyuki, et al, "Cytoplasmic Gene Expression System Enchances the Efficiency of Cationic Liposome–Mediated in Vivo Gene Transfer into Mouse Brain", Biochemical and Biophysical Research Communications 234, 1997, 15–18.
McCraken, S. et al, 5'Capping enzymes are targeted to pre–mRNA by binding to the phosphorylated carboxy–terminal domain of RNA polymerase II Genes & Development/ 11, 1997, 3306–3318.
Westwood, John,et al, "Analyses of Alternative Poly(A) Signals for Use in Baculovirus Expression Vectors", Virology 195, 1993, 90–99.
Proudfoot, Nicolas, "Ending the Message is Not So Simple", Cell, v. 87, Nov. 1996, 779–781.
Pasquinelli, Amy E., et al, Reverse 5' caps in RNAs made in vitro by phage RNA polmerases, RNA, 1998, 957–967.

* cited by examiner

Primary Examiner—W. Gary Jones
Assistant Examiner—Janell E. Taylor
(74) Attorney, Agent, or Firm—Fulbright & Jaworski, L.L.P.

(57) ABSTRACT

The present invention relates to the use of baculovirus RNA polymerase for the production of capped and polyadenylated transcripts in vivo and especially in vitro. More particularly, the purified RNA polymerase of the present invention may be used to produce in vitro transcription and/or in vitro transcription/translation kits.

24 Claims, 36 Drawing Sheets

A
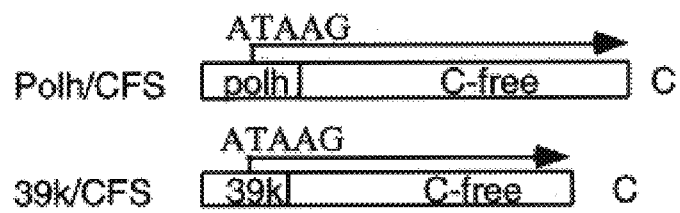
B
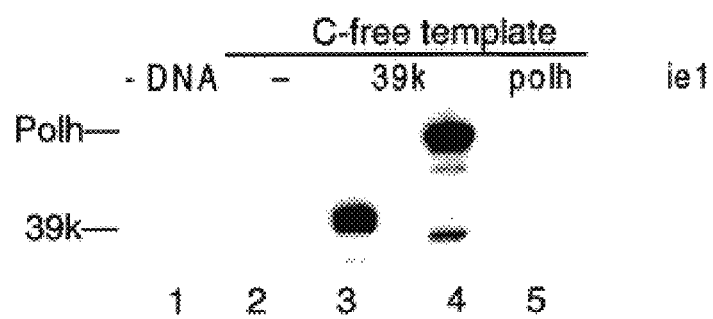
FIG. 5

A
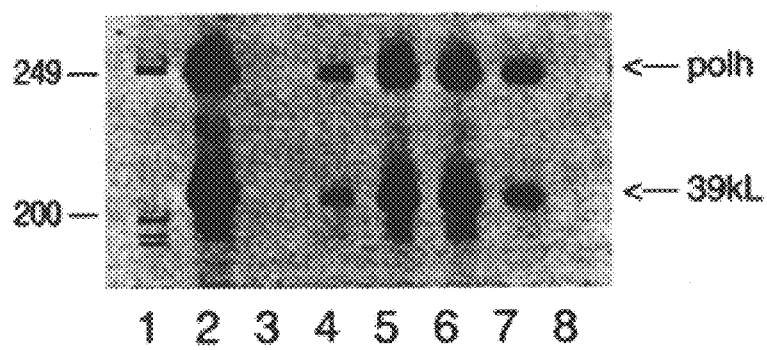
B
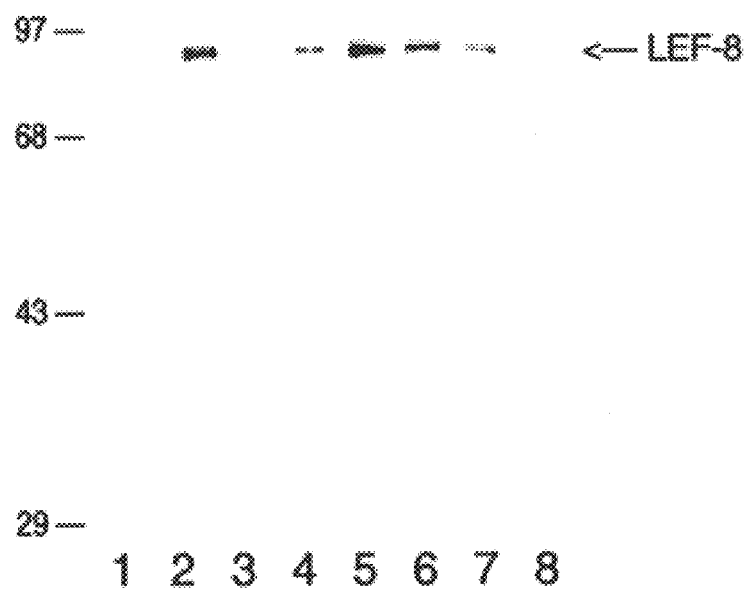
FIG. 6

```
       251 SVKKWALKLDGMRGRGLFMRNFCIIQTDDMQFYKTKMANLFALNNIVAFQCEVMDKQKIY 310
AcNPV      SVKKWALKLDGMRGRGLFMRNFCIIQTDDMQFYKTKMANLFSLNNIVAFQCEVMDKQKIY
BmNPV      GVKKWAFKLDGVRGRGAFRRGYCLVQTDDMQLHAACISSPFGLNNVVTFQCEVV-ADKIF
OpNPV      YYVCEKTDGLR                                      TLLDGELV
Sce CE            I                                            III

311 ITDLLQVFKYKYNNRTQYECGVNASYAIDPVTAIECINYMNNVQSVTLTDTCPAIELRF 370
AcNPV      ITDLLQVFKYKYNNRTQYECGVNASYAIDPVTAIECINYMNMSNVQSVTLTDTCPEIELRF
BmNPV      VTDLLQVFRYKYNNRTQYECNLHDAYPINADVAVECLNRLHCAVGSVPWPGLG---ELRF
OpNPV                       RYLMFDCLAING
Sce CE                           IIIa

371 QQFFDPPLQQSNYMTVSVDGYVVLDTELRYVKYKWMPTTELEYDAVNKSFNTLNGPLNGL 430
AcNPV      QQFFDPPLQQSDYMTVSVDGYVVLDTELRYVKYKWMPTTELEYDAVNNSFNTLNGPLNGL
BmNPV      QQFFDPPLAPTHYTTIPIDGYIVLDEQLQYAKYKWLPTVELEYDAPSGALHSIDGPLLGK
OpNPV                                     DGLIF    LLKWKPEQENTVD
Sce CE                                       IV         V

431 MILTDLPELLHENIYECVITDTTINVLKHRRDRIVPN                        470
AcNPV      VILTNLPELLHENIYECVIADTTINVLKHRRDRIVPN
BmNPV      TVVADL-QLKHGAVYECAITDNAINVLKCRPDRIVPSKVC
OpNPV                                WEMLRFRDDK
Sce CE                                   VI
```

```
                          *  *
AcNPV     MDYGDFVIEKEISYS-INFSQDLLYKILNSYIVPNYSL-AQQYFDLYDE-
BmNPV     MDHGNFMIEKEISYS-INFSQDLLYKILNSYIVPNYSL-AQQYFDLYDE-
OpNPV     MGA-DVLIEQEISYT-INFSQDLLYLILDSYIKKRCAAPAERYTDLYDA-
VAC       STAYEINNELELVFI-KPPLITLTNVVNISTIQE--SFIRFTVTNKEGVK
ASF       QSLKNSTIELEIRFQQINFLLFKT-VYEALVAQEIPSTISHSIRCIKKVH

*
AcNPV     --NGFRTRIPIQSACNNIISSVKKTNSKHKKFVYWPKDTNALVPLVWRES
BmNPV     --NGFRTRIPIQSACNNIISSVKKTNSKHKKFVYWPKDTNALVPLVWRES
OpNPV     --NNVRTRQTADSAV-----SVHKTNLRDERFVHWLRSSNALVPLVRREN
VAC       I----RTKIPL-SKVHGLDVKNVQLVDAIDNIV-WEKKS--LVTEN-RLH
ASF       HENHCREKIPL-SENLYFKKQPLMFFKFSEPASLGCKVSLAIEQPIRKFI

F
AcNPV     KEIKLPYKTLSHNLSKIIKVYVYQHDKIEIKFEHVYFSKSDIDLFDSTMA
BmNPV     KEIKLPYKTLSHNLSKIIKVYVYQHDKIEIKFEHVYFSKSDIDLFDSTMA
OpNPV     RETAVPHDRVSRHIASLIETTVYKLDGVDVKFEHVYMQSGPADRYESTAA
VAC       KECLLRLSTEERHIFLD-----YKKYGSSIRLELV--NLIQAKTKNFTID
ASF       LDSSVLVRLKNRTTFRVSELWK-------IELTIVK-QLMGSECSAKLAA

*  *
AcNPV     NKISKLLTLLENGDA-SETLQNSQVGSDEILARIRLEYEFDDDAPDDAQL
BmNPV     NKISKLLTLLENGNASSETLQNSQVGSDEILARIRLEYEFDDDAPDDAQL
OpNPV     HKIAALKTALLGVDCARPS-QNLQLGSDAVLARVRLELEFEGAAPAAASL
VAC       FKLKYFLGSGAQSKSSLLHAINHPKSRPNTS----LEIEFTPRDNETVPY
ASF       FKTLLFDTPEQQTTKNMMTLINP---DDEYL--YEIEIEYTFKPESLTAA
```

A
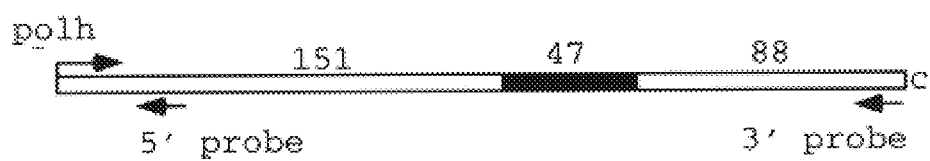
B  C
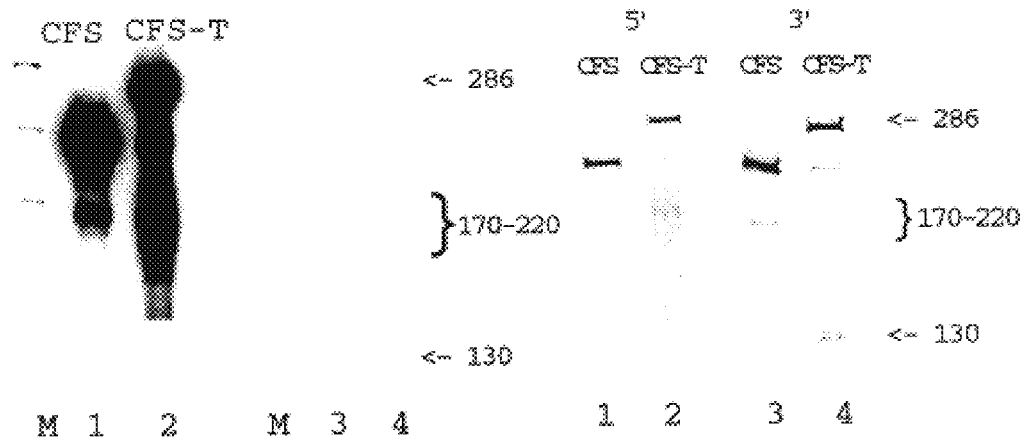
FIG. 25

AATAAAAGATGTTTATTTTGATTAGATGTGTGTTGGTTTTTTTGTGTAAAT

FIG. 31

IN VITRO SYNTHESIS OF CAPPED AND POLYADENYLATED MRNAS USING BACULOVIRUS RNA POLYMERASE

This application claims priority to U.S. Provisional Application No. 60/157,921, which was filed Oct. 6, 1999.

BACKGROUND OF THE INVENTION

At least some of the present invention may have been made with funds from the United States Government, which may therefore have certain rights in this invention.

1. Field of the Invention

Aspects of the present invention relate to the discovery and use of baculovirus RNA polymerase for the production of capped and polyadenylated transcripts in vivo and in vitro. Aspects relate to useful tools and techniques for biotechnologists, including more stable RNA transcripts produced.

2. Background of the Related Art

A. Baculovirus

Baculoviruses are popular eukaryotic expression vectors. The baculovirus system has been used to produce hundreds of different proteins for basic research and pharmaceutical applications such as medical therapeutics, diagnostics, vaccines, and drug discovery. Baculoviruses have been adapted as expression vectors because they normally produce abundant amounts of a viral protein called polyhedrin during the very late stage of viral infection. Polyhedrin is essential for the propagation of baculoviruses in insects, but is nonessential for growth in tissue culture. Thus the polyhedrin open reading frame can be replaced by coding regions for target genes of choice, and in many cases, target proteins are expressed at levels equivalent to that of polyhedrin, which is approximately 1 mg per ml of culture. In addition, eukaryotic proteins are frequently subject to the appropriate post-translational modifications, including phosphorylation, glycosylation, and acylation.

*Autographa californica* nuclear polyhedrosis virus (AcNPV) is the prototype member of the Baculoviridae, which is a large family of DNA viruses that are pathogenic for invertebrates. The AcNPV genome consists of a double-stranded, supercoiled DNA molecule of 134 kbp, and potentially encodes 150 proteins (Ayres et al., 1994). In infected cells, AcNPV genes are expressed in a temporally controlled and ordered fashion (Blissard and Rohrmann 1990; O'Reilly et al., 1992). Viral genes are classified as early or late based on their requirements for viral DNA replication. Transient expression assays suggest that there are two distinct classes of early genes. One class includes genes like ie1 and ie2 that are highly expressed in the absence of other viral proteins and enhancer elements (Guarino and Summers, 1986a; Carson et al., 1988). The other class includes genes like 39k that are expressed at basal levels in the absence of viral factors, but whose expression is enhanced approximately 1000-fold in the presence of IE1 and cis-linked enhancer elements (Guarino and Summers, 1986b). Baculovirus early promoters resemble those transcribed by eukaryotic RNA polymerase II (pol II). Transcription of the early genes is inhibited by α-amanitin, consistent with the hypothesis that early genes are transcribed by host pol II (Fuchs et al., 1983; Grula et al., 1981). Transcription of several early baculovirus genes initiates within a conserved 'CAGT' motif. Mutagenesis of this element was shown to affect transcription initiation in the 39k promoter (Guarino and Smith, 1992) and in the gp64 promoter (Blissard et al., 1992), suggesting that CAGT functions as an initiator element.

Late genes are also divided into two classes: the late genes, many of which encode viral structural proteins, and the very late genes, which are associated with the formation of viral occlusions. Transcription of both classes of late genes is resistant to (α-amanitin (Huh and Waver, 1990), suggesting that these genes are transcribed by a viral-encoded RNA polymerase. This polymerase may be encoded by the lef-8 gene of AcNPV (Passarelli et al., 1994). Late and very late genes contain the consensus late promoter element, TAAG. This core element appears to function as both a promoter and an mRNA start site (Rankin et al., 1988).

Several proteins (LEF=late expression factor) required for late gene expression have been identified (Table 1; Passarelli and Miller, 1993a,b,c,1994; Passarelli et al., 1994; Li et al., 1993; Morris et al., 1994; Lu and Miller, 1994; McLachlin and Miller, 1994). The genes encoding these proteins were mapped using a transient transfection assay. Some of these proteins may be directly involved in late gene expression, and some may only be required for earlier events in the virus life cycle. For example, IE1 and IE2 transactivate early gene expression (Guarino and Summers, 1986a; Carson et al., 1988); and LEFs 1–3, helicase, and DNA polymerase are required for DNA replication (Kool et al., 1994). Little is known about the roles of LEFs. The predicted amino acid sequence of LEF-8 contains a motif that is conserved in RNA polymerases from various sources (Passarelli et al., 1994).

TABLE 1

Viral proteins required for the expression of late and very late genes.

| Protein | Molecular weight | Structural features | Associated functions |
|---|---|---|---|
| IE1 | 71 kDa | Acidic region and DNA binding domain | Transactivates early genes. Binds to enhancers/origins |
| IE2 | 47 kDa | Several motifs common to transcription factors | Co-activator for early transcription |
| LEF-1 | 31 kDa | Nucleotide triphosphate binding motif | Required for DNA replication |
| LEF-2 | 23 kDa | | Required for DNA replication |
| LEF-3 | 44 kDa | | Required for DNA replication Single-stranded DNA binding protein |
| Helicase | 143 kDa | Homology with helicases | ts mutants are DNA negative. Required for DNA replication. |
| DNA pol | 114 kDa | Homology with DNA polymerases | Required for DNA replication |
| P35 | 35 kDa | | Suppressor of apoptosis |
| LEF-4 | 54 kDa | | |
| LEF-5 | 31 kDa | | |
| LEF-6 | 20 kDa | | |
| LEF-7 | 24 kDa | Zinc finger | |
| LEF-8 | 102 kDa | RNA polymerase motif | |
| LEF-9 | 59 kDa | | |
| LEF-10 | 9 kDa | | |
| pp31/39K | 31 kDa | | DNA binding protein |
| VLF-1 | 44 kDa | Homology with integrases | Very late expression factor |

B. In Vitro Transcription of Capped RNAs

A number of research protocols have been developed that require milligram amounts of purified mRNAs. These RNAs are usually transcribed in vitro using plasmids or PCR fragments as templates. The most commonly used RNA polymerases for in vitro transcription are the enzymes encoded by the bacteriophages T3, T7, and SP6. These RNA polymerases are useful because they are highly active, very processive enzymes that recognize a specific promoter. In vitro transcription reactions with these enzymes are usually done as run-off assays. In this type of assay, the plasmid DNA is linearized prior to transcription, and so the 3'-end of the message is determined by the end of the DNA template. As a result, the transcripts produced are appropriate for translation in prokaryotic systems, but are not optimal for eukaryotic systems because they are not processed at the 5' end with a 5'-methyl-7-guanosine cap and at the 3' end with a poly(A) tail.

The most common use of in vitro transcribed RNAs is cell free translation, either in rabbit reticulocyte or in wheat germ extracts. Efficient in vitro translation of the RNAs requires the presence of a 5'-methyl-7-guanosine cap. The cap structure is important for binding of ribosomes to the RNA and also for message stability. Thus uncapped transcripts, which are the normal product of bacteriophage RNA polymerases, are not efficiently translated in eukaryotic cell free systems. Other protocols that require capped transcripts include microinjection of mRNAs into oocytes or transfection of mRNAs into animal cells or plant cells for the purpose of studying in vivo RNA processing, RNA transport, or protein function. Capping for these in vivo is essential because RNAs that are uncapped are rapidly degraded by cellular RNases. Also, in vitro splicing assays and the characterization of splicing factors require capped RNAs as substrate because the cap structure helps to target splicing enzymes to their substrates.

The production of capped mRNAs is usually done by adding cap analog (7mGpppG) to the in vitro transcription reactions. Cap analog can be incorporated in place of GTP al the 5' end of the message. Although this is not the typical route of cap formation, the use of cap analog in transcription reactions yields RNAs with authentic and fully functional caps. There are, however, several disadvantages to the use of cap analog. First, cap analog is an expensive reagent, and costs approximately 20-times more than GTP. Second, the use of cap analog reduces the yields of RNA because the GTP concentration must be reduced to favor incorporation of the cap. Furthermore, even under these optimized conditions, only 80% of the messages are capped. For very long messages, the ratio of GTP to cap analog has to be increased to permit synthesis of full-length messages, thus further reducing the proportion of capped messages. Another problem is that cap analog binds to eukaryotic translation initiation factors and so is a competitive inhibitor of translation. This necessitates the complete removal of cap analog from the mRNA prior to translation, a step that could potentially lead to loss of RNA or other complications. Finally, it has been shown that methylated cap analogs are frequently incorporated into RNAs in a reverse orientation, so that the 5' end of the message is Gppp7mGNNN instead of 7mGpppGNNN (Pasquinelli et al., 1995). The proportion of reverse-capped RNAs can be as high as 50%, and this is particularly problematical because many proteins that interact with mRNA caps do not recognize reverse caps.

The only commercially available alternative to cap analog is vaccinia virus capping enzyme. This two-subunit complex contains all three of the enzymatic activities (RNA 5'-triphposphatase, guanylyltransferase, and cap methyltransferase), that are required for the formation of a 5' cap. Thus vaccinia virus capping enzyme can be used for posttranscriptional modifications of RNA after synthesis by one of the bacteriophage RNA polymerases. Caps can then be added using GTP and S-adenosyl-methionine (SAM). This is the normal route of synthesis, and these reagents are cheaper than cap analog. The drawback is that vaccinia capping enzyme is normally targeted to RNA substrates through interactions with vaccinia RNA polymerase, and in the absence the cognate RNA polymerase, very high molar amounts of capping enzyme have to be used to drive the capping reaction. Thus the advantage gained by avoiding the use of cap analog is more than offset by the expense of the capping enzyme.

C. In Vitro Transcription of Polyadenylated RNAs

The 3' end of most eukaryotic mRNAs contains a stretch of adenylate residues, usually 100–200 nt in length. In vivo, the poly(A) tail has two primary effects. It increases message stability, and also binds factors that enhance translation initiation (Jackson and Standart, 1990). In vivo, the effects of capping and polyadenylation are synergistic so that the translational efficiency of capped and polyadenylaled messages is increased 450-fold compared unprocessed messages; capping alone increases translation only 20-fold, while polyadenylation alone has little effect (Gallie, 1991). Thus polyadenylation is highly recommended for RNAs to be used for transfection into eukaryotic cells.

The commercially available eukaryotic translation systems, wheat germ and rabbit reticulocyte, are relatively insensitive to the polyadenylation signals, however, and so 3' processing is often omitted. Some companies (e.g. Promega) recommend it for optimal translational efficiencies because it does result in a 2–5-fold increase, lower than in vivo but still significant.

There are no commercially available enzymes for the production of polyadenylated RNAs, so messages with poly(A) tails are commonly produced using vectors that contain an oligo(dT) region on the template strand. The disadvantage of these vectors is that the poly(A) tail is usually shorter than normal (30 nt instead of 100–200), and there are frequently non-A residues at the end of the tail because it is necessary to have a restriction enzyme recognition site downstream of the templated adenylates.

Recently, two in vitro translation systems have been developed that better mimic the response of the eukaryotic translational machinery to the 5' cap and poly(A) tails. In the yeast system, capped and polyadenylated mRNAs were translated 750-fold more efficiently than unprocessed RNAs, as compared to only a 3.7-fold increase for the same RNAs in reticulocyte extracts and a 6.8-fold increase in wheat germ extracts (Iizuka et al., 1994). A Drosophila embryo in vitro translation system, which similarly reproduces the synergism between the cap and poly(A) tail, has also been reported (Gebauer et al., 1998). The use of these systems promises to increase the power and utility of in vitro translation systems, but they can only be widely adapted by the research and diagnostic communities if convenient systems are simultaneously supplied for in vitro transcription of capped and polyadenylated RNAs.

The present invention solves these problems in the art by providing a baculovirus RNA polymerase that is relatively simple, being a four subunit complex, that can transcribe, cap and polyadenylate transcripts in vitro. Polyadenylation offers at least significant increases in stability of mRNAs and at least increases the efficiency of translation. The present invention hence solves the limitations in the prior art, including those addressed above. Present objects of the present invention therefore relate to materials and methods for producing stable, capped and polyadenylated RNAs in vitro and in vivo using a single RNA polymerase enzyme in methods that overcome prior art limitations.

SUMMARY OF THE INVENTION

The inventors have discovered that baculovirus RNA polymerase has the intrinsic ability to both cap and polyadenylate transcripts. The inventors presently understand that no other RNA polymerase is known with the intrinsic ability to both cap and polyadenylate transcripts. Prior to the discoveries of the present invention, most baculovirologists long assumed that polyadenylation was mediated by host enzymes. Indeed, showing this belief, most baculovirus expression vectors currently sold commercially have incorporated eukaryotic signals for cleavage and polyadenylation.

An embodiment disclosed herein provides a method of capping and polyadenylating RNA transcripts comprising the steps of: producing an RNA transcript using baculovirus RNA polymerase, wherein the baculovirus RNA polymerase caps and polyadenylates the RNA transcript.

In specific embodiments, producing the RNA transcript comprises an expression vector comprising a promoter sequence, a polynucleotide sequence and a baculovirus terminator sequence. The expression vector is prokaryotic or eukaryotic. More, particularly, the promoter sequence comprises a baculovirus consensus sequence or a sequence that is functionally equivalent. The consensus sequence is TAAG.

In further embodiments producing RNA transcripts may further comprise an accessory protein. These accessory proteins may enhance, for example, transcription, capping and/or polyadenylation. Exemplary accessory proteins include, but are not limited to, LEF-5 or VLF-1. Another accessory protein is a viral methyltransferase. Also, contemplated is that more than one accessory protein may be used to further enhance transcription.

In further embodiments, the method is performed in a cell. The cell is prokaryotic or eukaryotic. Yet further, the method is performed in a cell-free system or in vivo.

Specifically, the polymerase is a four subunit complex. The subunit complex comprises LEF-8, LEF-4, LEF-9 and p47. More particularly, LEF-4 subunit mediates capping. Yet further, polymerase terminates after a T-rich region in the transcript.

Also disclosed herein is a method of capping RNA transcripts comprising the steps of: producing an RNA transcript in vitro using baculovirus RNA polymerase, wherein the baculovirus RNA polymerase caps the RNA transcript. Specifically, the polymerase is a four subunit complex comprising LEF-8, LEF-4, LEF-9 and p47. hi specific embodiments, LEF-4 subunit mediates capping.

Another embodiment is a method of polyadenylating RNA transcripts comprising the steps of: producing an RNA transcript in vitro using baculovirus RNA polymerase, wherein the baculovirus RNA polymerase polyadenylates the RNA transcript. More specifically, the polymerase terminates after a T-rich region in the transcript.

In other specific embodiments, the present invention herein discloses an in vitro transcription kit comprising: a vector comprising a promoter sequence, a multiple cloning site and a baculovirus terminator sequence; transcription mix; and a baculovirus RNA polymerase. More particularly, the vector is prokaryotic or eukaryotic.

Yet further, the promoter comprises a baculovirus promoter consensus sequence or a functional equivalent of the baculovirus consensus sequence. The consensus sequence is TAAG. The polymerase is a four subunit complex. Specifically, the subunit complex comprises LEF-8, LEF-4, LEF-9 and p47. In specific embodiments, LEF-4 mediates capping.

In further embodiments, the kit may comprise an accessory protein. It is contemplated that an accessory protein enhances transcription. Exemplary accessory proteins include, but are not limited to, LEF-5, VLF-1 or a viral methyltransferase. It is also contemplated that more than one accessory protein may be used in the kit.

Another embodiment of the present invention is a coupled transcription-translation kit comprising: a vector comprising a promoter sequence, a multiple cloning site and a baculovirus terminator sequence; transcription mix; translation mix; and a baculovirus RNA polymerase. Specifically, the vector is prokaryotic or eukaryotic.

In specific embodiments, the promoter comprises a baculovirus promoter consensus sequence or a functional equivalent. More particularly, the consensus sequence is TAAG.

In a further specific embodiment, the polymerase is a four subunit complex. Specifically, the subunit complex comprises LEF-8, LEF-4, LEF-9 and p47. LEF-4 mediates capping.

In further embodiments, the kit may comprise an accessory protein. The accessory protein may be LEF-5, VLF-1 or a viral methyltransferase. Yet further, the kit may comprise more than one accessory protein.

As used herein the specification, "a" or "an" may mean one or more. As used herein in the claim(s), when used in conjunction with the word "comprising", the words, "a" or "an" may mean one or more than one. As used herein "another" may mean at least a second or more.

Other objects, features and advantages of the present invention are apparent in the following detailed description. It should be understood, however, that the detailed description and the specific examples, while indicating preferred embodiments of the invention, are given by way of illustration only, since various changes and modifications within the spirit and scope of the invention are apparent to those skilled in the art in this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
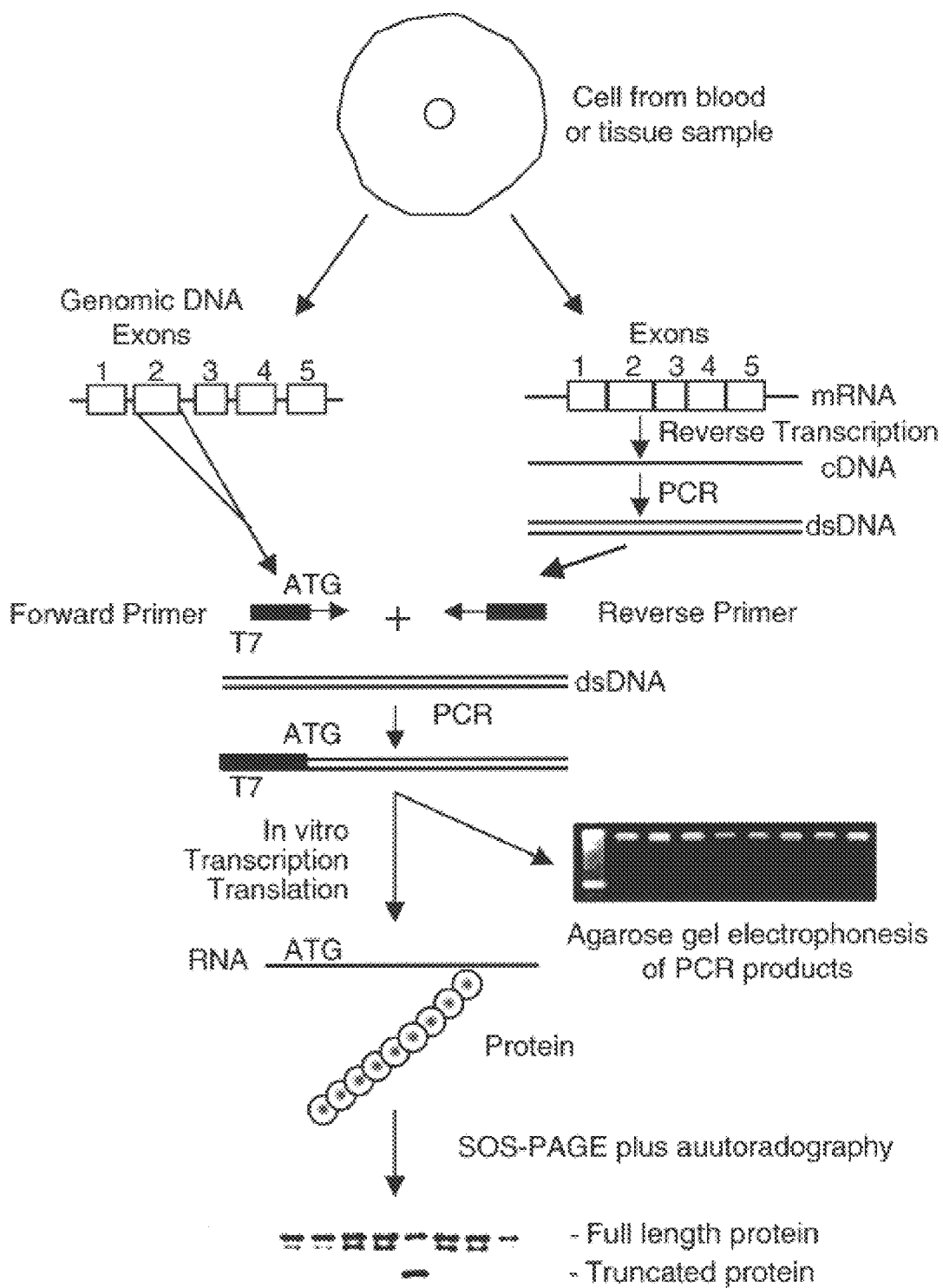
FIG. 1 Schematic diagram of the protein truncation test (Hogervorst 1997).

CFS are indicated on the right. The positions of elution of blue dextran 2000 (BD), thyroglobulin (THY; 669 kDa), ferritin (FER; 4043 kDa), catalase (CAT; 232 kDa), and aldolase (ALD; 158 kDa) were determined by elution of protein standards under the same conditions. (B) Proteins in the corresponding fractions were separated by electrophoresis of an SDS-8% polyacrylamide gel and visualized by staining with silver. The apparent molecular weights (in kilodaltons) of the bands that correspond with transcription activity are shown on the right. The migration of protein molecular weight markers (in kilodaltons) are indicated on the left. (C) Quantitation of subunits. Purified RNA polymerase (lanes 8 and 9 contain 300 and 150 ng. Respectively) was separated by SDS-PAGE and stained with Coomassie brilliant blue. Lanes 2 to 6 contain bovine serum albumin (100, 200, 400, 600, and 800 ng); lane 1 contains molecular markers.

FIG. 5. Transcription templates. Standard in vitro transcription reactions contain two cytidine-free templates (A). Transcription initiates from the late 39k promoter or the very late polh promoter and pauses at the first cytidine downstream of the C-free cassette. Transcription reactions are analyzed by acrylamide gel electrophoresis (B). The plasmid ie1/CFS contains the immediate early ie1 promoter linked to the same C-free cassette. The ie1 promote is transcribed by host RNA polymerase II.

FIG. 6. Recognition of the large subunit with LEF-8 antiserum. (A) The Mono Q peak fraction (lane 2) was filtered through Superose 6. Proteins corresponding to the peak of protein at 560,000 were assayed for transcription activity (lanes 3 to 8). Positions of the polh and 39kL transcripts are indicated on the right. ΦX174 molecular markers are shown in lane 1. (B) Superose 6 factions containing transcription activity were electrophoresed on SDS-8% polyacrylamide gels, transferred to nitrocellulose membranes, and probed with LEF-8 antiserum. Lane 1, prestained molecular weight markers, with sizes (in kilodaltons) indicated on the left. The position of the immunoreactive protein is shown on the right.

Figure 7:
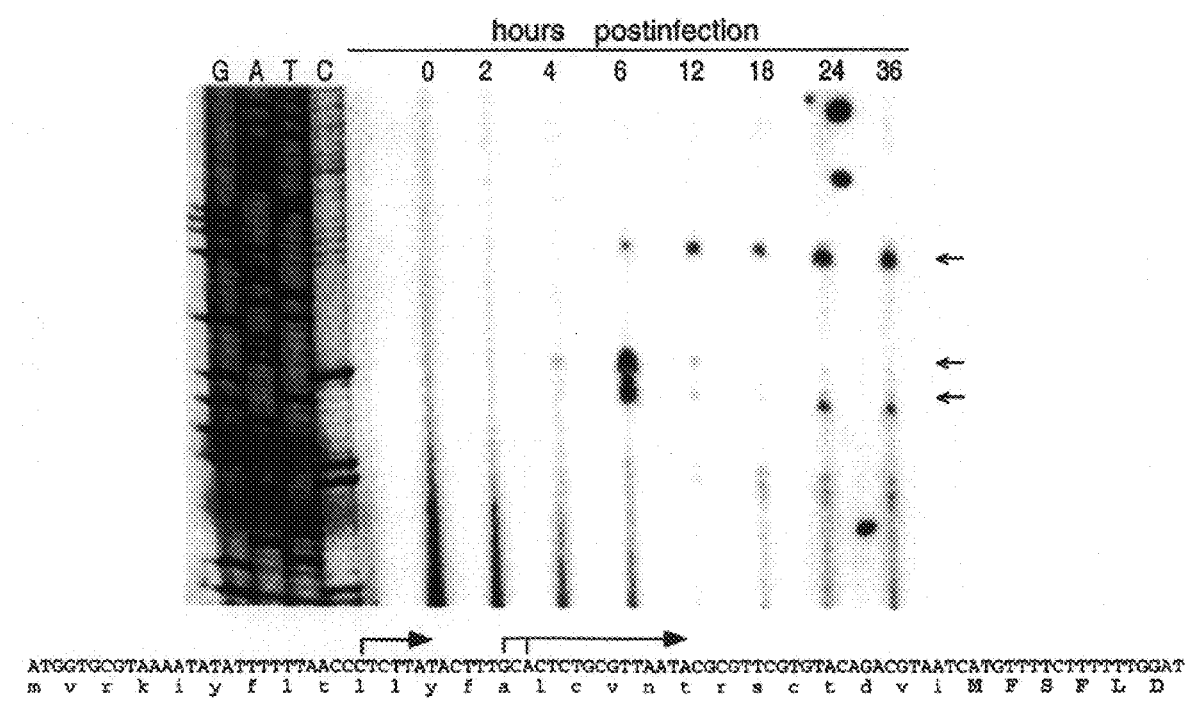

FIG. 7. Primer extension mapping of lef-9 mRNA. Total cellular RNA was isolated from AcNPV-infected Sf9 cells at the indicated times postinfection. The 5' end of the transcripts was mapped by primer extension analysis using an oligonucleotide complementary to nt 49300 to 49319 of the AcNPV genome sequence (1). Sequencing ladders were generated by using the same primer. The sequence ladder is antisense relative to the sequence of the lef-9 promoter shown below. The primer extension products are denoted by arrows on the right and correspond to arrows above the sequence, which indicate the transcription start sites. The amino acid residues identified by N-terminal sequencing are shown in uppercase; the 26-residues predicted to be at the N terminal of LEF-9 are shown in lowercase.

Figure 8:
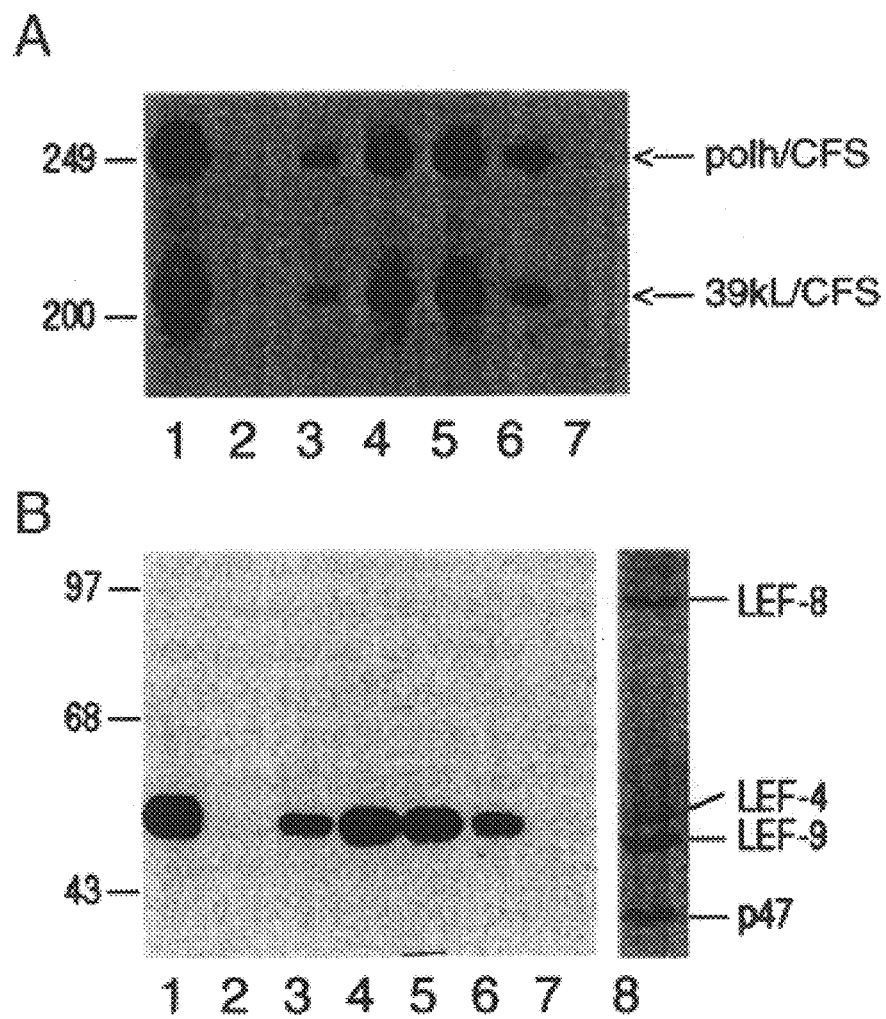

FIG. 8. Guanylyltransferase activity of baculovirus RNA polymerase. (A) Gel filtration chromatography of RNA polymerase. RNA polymerase was filtered through Superose 6 as previously described (11). Fractions corresponding to the peak of absorbance at 280 nm were assayed for in vitro transcription activity (lanes 2 to 7). A transcription assay of the material loaded onto the column is shown in lane 1. The transcripts corresponding to polyhedrin the (Polh/CFS) and 39k (39kL/CFS) promoters are indicated on the right. The sizes of the relevant (ΦX174-Hinfl molecular markers are shown on the left. (B) Guanylyltransferase assays. Proteins in the corresponding fractions were incubated with 50 mM Tris (pH 7.9), 2 mM DTT, 2 mM MgCl2, and 1 μM [α-$^{32}$P]GTP. After incubation for 15 min at 30° C., samples were resolved by SDS-PAGE. Gels were dried and exposed to X-ray film Lane 8 shows the migration of the RNA polymerase subunits as detected by silver staining. The positions of the four polymerase subunits are indicated on the right. The positions of relevant molecular weight protein markers are shown in kilodaltons on the left.

FIG. 9. Sequence of the LEF-4 guanylyltransferase domains. The C-terminal 220 residues of LEF-4 proteins from AcNPV, Bombyx mori nuclear polyhedrosis virus (BmNPV), and Orgyia pseudotsugata nuclear polyhedrosis virus (OpNPV) were aligned by using the GCG Pileup program (30). Residues corresponding to six sequence elements (designated motifs I, III, IIIa, IV, V, and VI) from the S. cerevisiae capping enzyme (Sce CE) (30) were aligned by eye with the corresponding regions in the baculovirus enzymes. Residues in the yeast capping enzyme that have been shown to be essential for function by alanine substitution (30) are underlined.

Figure 10:
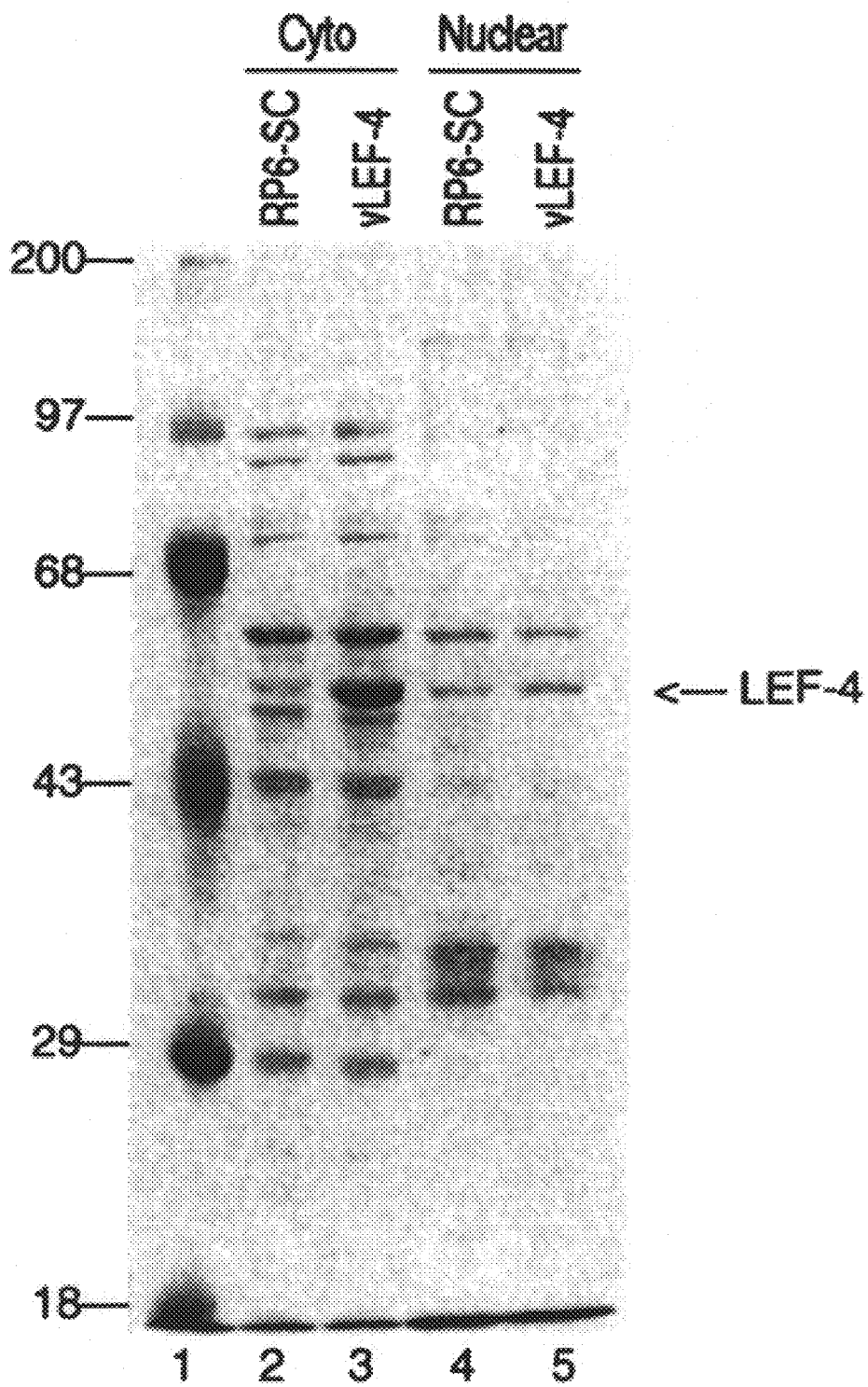

FIG. 10. Expression and localization of LEF-4 in baculovirus-infected cells. S. frugiperda cells infected with vLEF-4 (lanes 3 and 5) or the parental virus RP6-SC (lanes 2 and 4) at a multiplicity of infection of 10. At 48 h postinfection, cells were harvested, washed in phosphate-buffered saline, and separated into nuclear and cytosolic (cyto) fractions. Equivalent amounts of protein each fraction were separated on SDS-polyacrylamide gels and stained with Coomassie brilliant blue. Protein molecular weight markers were loaded in lane 1, and the sizes of the relevant proteins are shown in kilodaltons on the left. The position of LEF-4 is indicated on the right.

Figure 11:
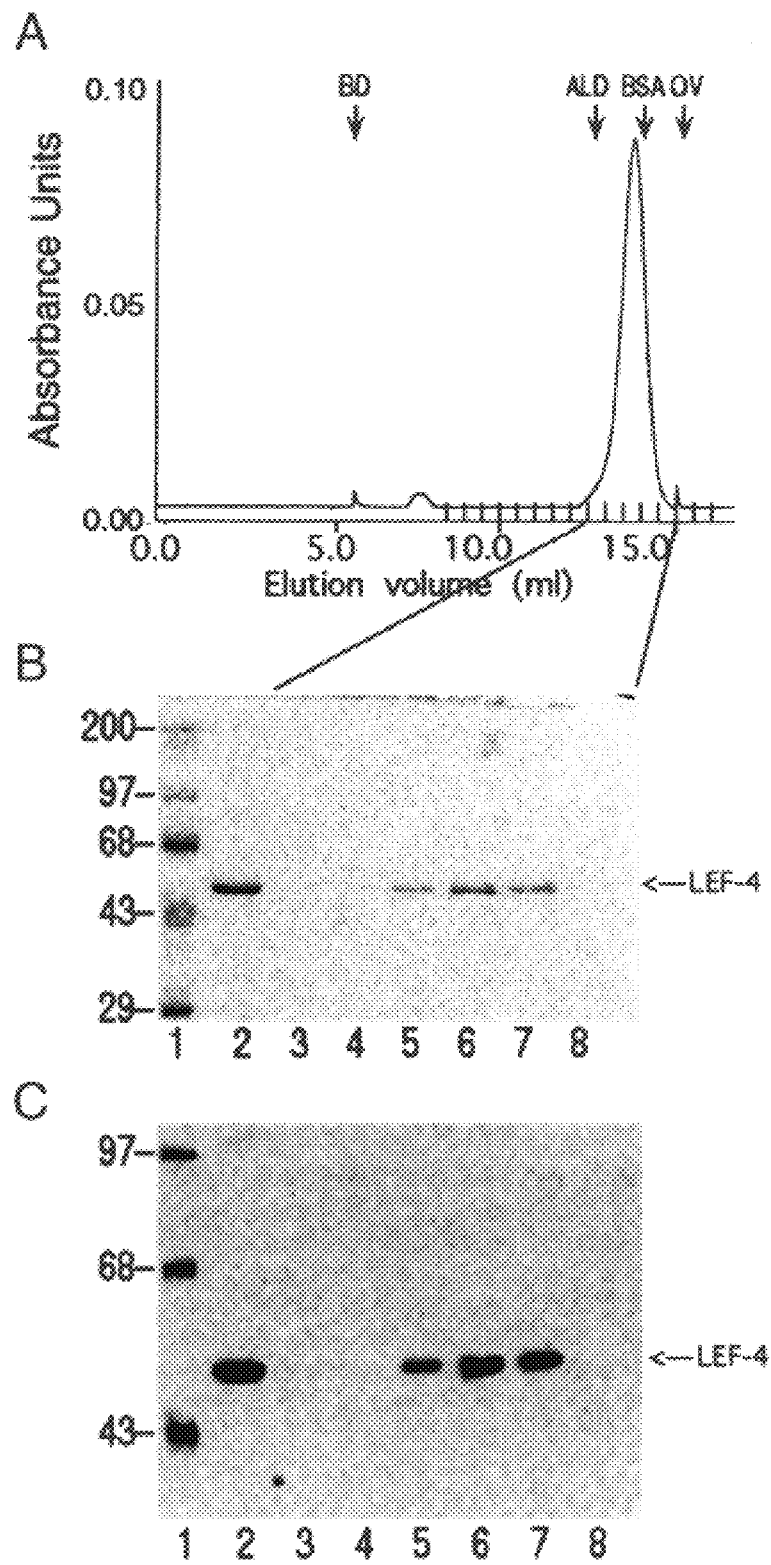

FIG. 11. Guanylyltransferase activity LEF-4. (A) Gel filtration chromatography of LEF-4. The peak of LEF-4 protein from a Mono Q column was filtered through Superdex 200. Fractions (0.5 ml) were collected from 8.5 to 16 ml. Marker proteins used for calculation of the molecular mass of LEF-4 were aldolase (ALD), bovine serum albumin (BSA), and ovalbumin (OV). The exclusion volume was determined by gel filtration of blue dextran 2000 (BD). (B) SDS-PAGE analysis of Superdex 200 fractions. Fractions 9 to 14 from the Superdex column were separated on an SDS-polyacrylamide gel (lanes 3 to 8) and stained with Coomassie brilliant blue. Lane 2 shows the Mono Q peak fraction that was loaded onto the column. Protein molecular weight markers were loaded in lane 1, and the sizes of the relevant proteins are shown in kilodaltons on the left. LEF-4 is indicated on the right. (B) Guanylyltransferase assays. Proteins in the corresponding fractions were incubated with 50 mM Tris (pH 7.9), 2 mM DTT, 1 mM MnCl2, and 1 μM [α-32P]GTP. After incubation for 15 min at 30° C., samples were resolved by SDS-PAGE. An autoradiograph of the dried gel is shown. Protein molecular weight markers were loaded in lane 1, and the sizes of the relevant proteins are shown in kilodaltons on the left. The position of LEF4 as judged by analysis of the Coomassie blue-stained gel is indicated on the right.

Figure 12:
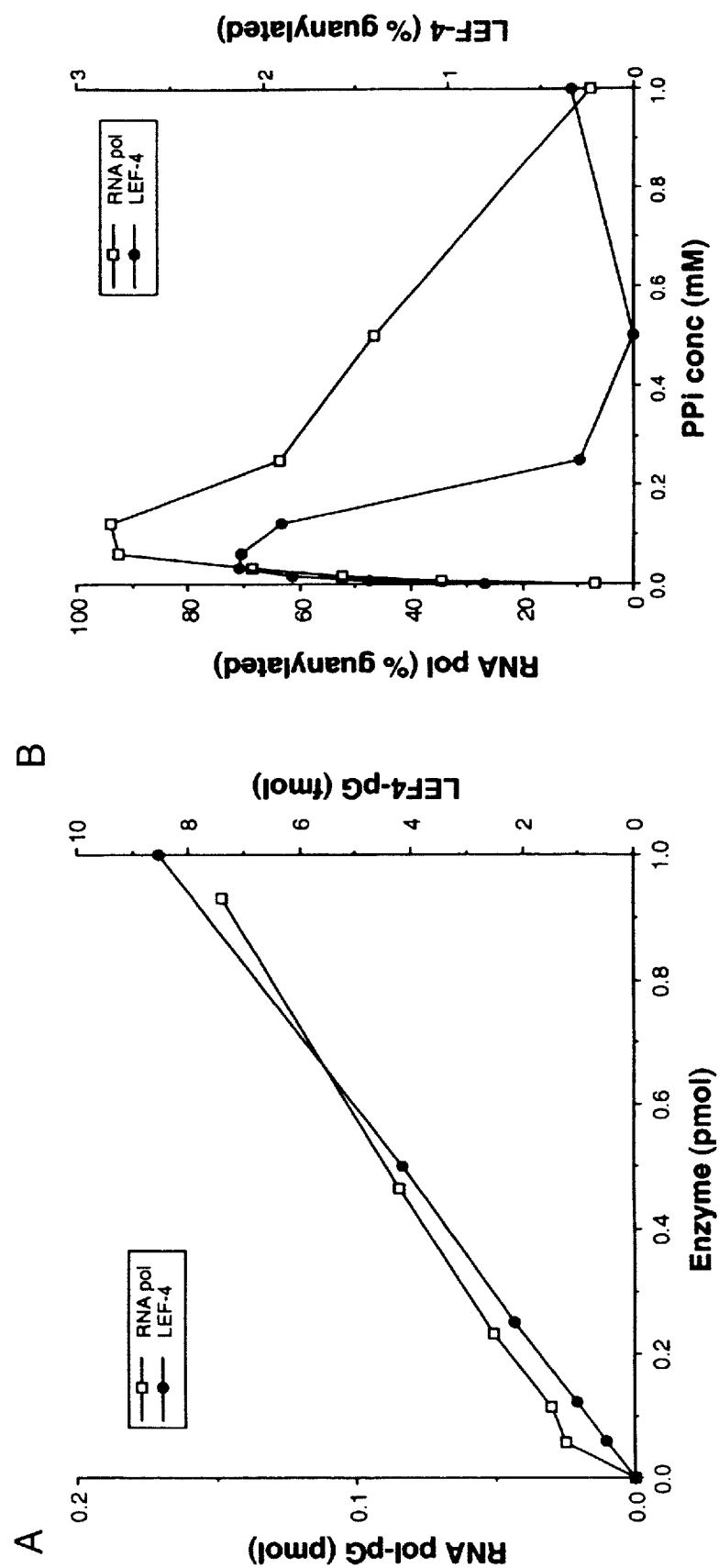

FIG. 12. Guanylyltransferase activity of purified LEF-4 and RNA polymerase (A Protein titration. Guanylyltransferase assays were performed with purified AcNPV RNA polymerase (pol) or with LEF-4 subunit. The reaction mixtures contained 50 mM Tris (pH 7.9), 5 mM DTT, 1 mM MnCl$_2$, and 5 μM [α-$^{32}$P]GTP, and RNA polymerase or LEF-4, as indicated. Reaction products were quantitated by scanning the SDS-polyacrylamide gel in a PhosphorImager. The yield of guanylated RNA polymerase (pol-pG) is plotted on the left (in picomoles of radiolabeled protein), and the yield of guanylated LEF-4 is plotted on the right. (B) Inhibition of guanylyltransferase activity by PP1. The reaction mixtures contained 50 mM Tris (pH 7.9), 5 mM DTT, 5 mM MnCl$_2$, 5 μM [60 -$^{32}$P]GTP, 1 pmol of RNA polymerase or LEF-4, and NaPP1 as indicated. The yield of guanylated RNA polymerase (expressed as percentage of input RNA polymerase radiolabeled) is plotted as a function of PP1 concentration on the left, and the yield of guanylated LEF-4 (expressed as percentage of input protein) is plotted on the right.

Figure 13:
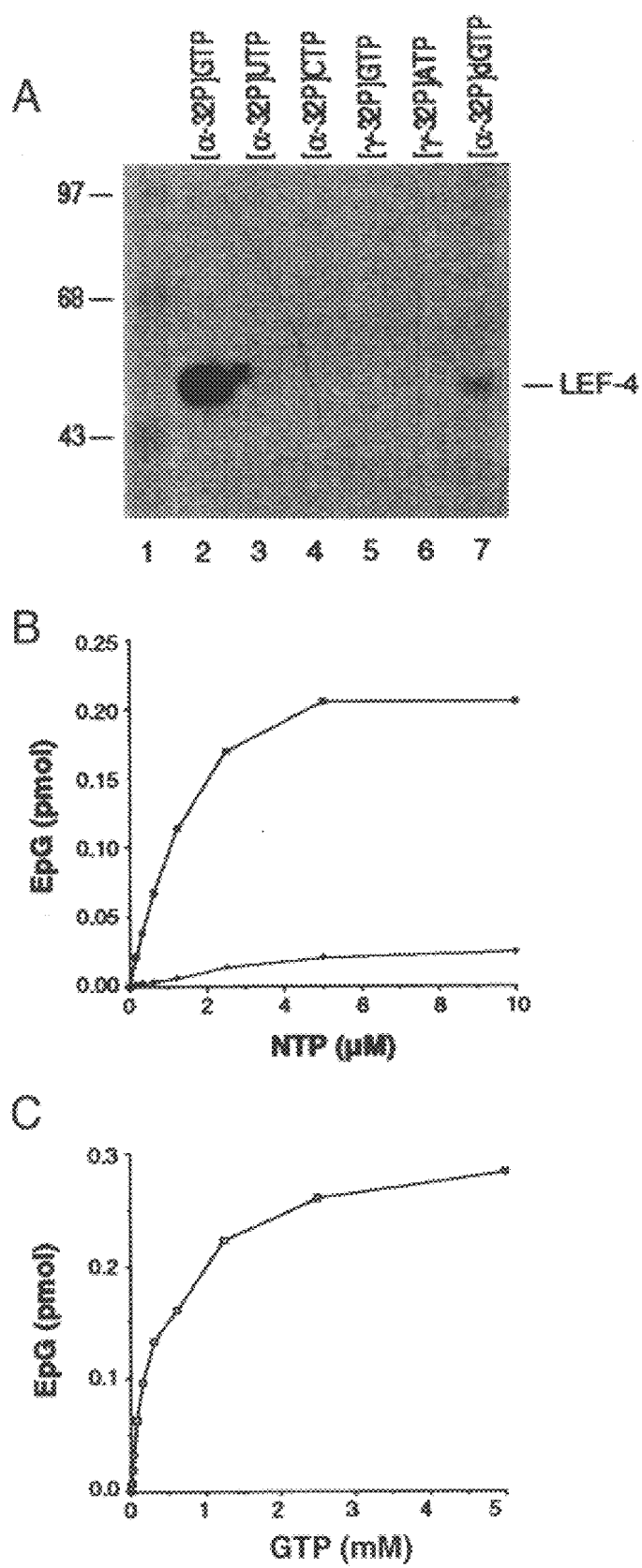

FIG. 13 Nucleotide and sugar specificity of the guanylyltransferase activity of RNA polymerase and purified LEF-4. (A) Nucleotide specificity. Incubations were preformed with 0.2 μM indicated nucleoside triphosphate. An autoradiograph of the dried gel is shown. The position of LEF-4 is indicated on the right, and the migration of molecular weight standards is shown in kilodaltons on the left. Reaction mixtures contained 1 pmol of purified RNA polymerase, 50 mM Tris HCl (pH 7.9), 1 mM MnCl$_2$, 5 mM DTT, and radiolabeled nucleotides as indicated. The specific activities of the nucleotides were as follows: [α-$^{32}$P]GTP, 5.9×10$^5$ cpm/pmol; [α-$^{32}$P]CTP, 5.3×10$^5$ cpm/pmol; [α-$^{32}$p]UTP, 4.0×10$^5$ cpm/pmol; [γ-$^{32}$P]GTP, 7.6×10$^5$ cpm/pmol; [γ-$^{32}$P]ATP, 4.0×10$^5$ cpm/pmol; and [α-$^{32}$P]dGTP, 5.5×10$^5$ cpm/pmol. (B) Nucleotide sugar specificity of guanylyltransferase of LEF-4. Reaction mixtures contained 1 pmol of purified RNA polymerase, 50 mM Tris HCl (pH 7.9), 1 mM MnCl$_2$, 5 mM DTT, and [α-32P]GTP (squares) or [α-$^{32}$P]dGTP (diamonds). Samples were incubated at 30° C. for 15 min. (C) GTP titration with purified LEF-4. Reaction mixtures contained 1 pmol of purified LEF-4, 50 mM Tris HCl (pH 7.9), 5 mM MnCl$_2$, 5 mM DTT, and [α-$^{32}$P]GTP.

Figure 14:
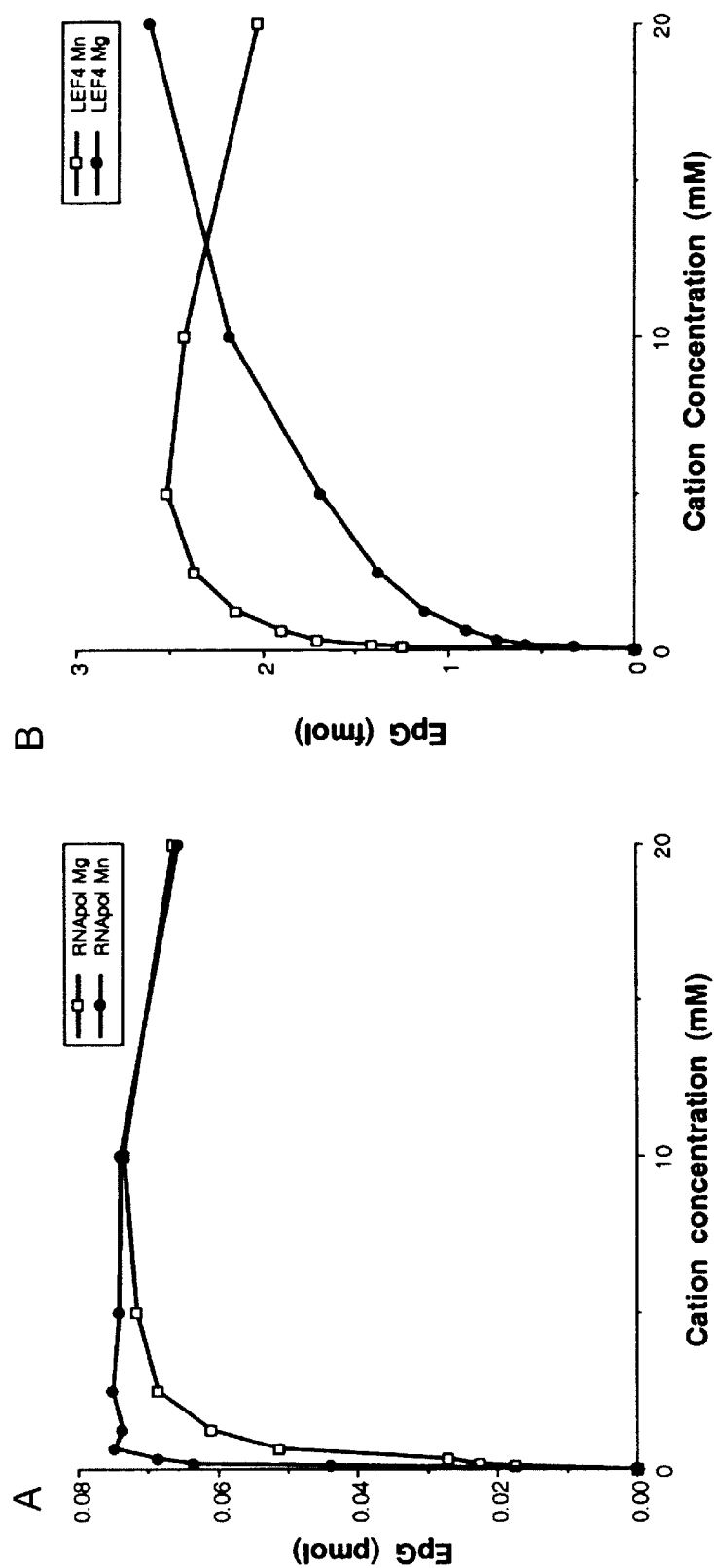

FIG. 14. Cation requirements of the guanylyltransferase activity of RNA polymerase (RNApol) (A) and purified LEF-4(B). Reaction mixtures contained 50 mM Tris HCl (pH 7.9), 5 mM DTT, 5 μM [α-$^{32}$P]GTP, and divalent cation as indicated in 25 μl. Reaction mixtures were incubated at 30° C. for 15 min and denatured in 1% SDS, and proteins were separated by PAGE. The yield of EpG is plotted as a function of magnesium or manganese concentration.

FIG. 15. Sequence of the LEF-4 RNA triphosphatase domain. The amino acid sequence of the AcNPV LEF-4 from residues 1 to 194 is aligned with the LEF-4 sequences of Bombyx mori nuclear polyhedrosis virus BmNPV) and Orgyia pseudotsugata nuclear polyhedrosis virus (OpNPV) and the N-terminal regions of the capping enzymes of vaccinia virus (VAC) and African swine fever virus (ASF). Gaps in the-sequence alignment are denoted by hyphens; residues that are identical in at least four of the five sequences are shown in bold; residues shown to be essential for RNA triphosphatase activity in vaccinia virus are indicated by asterisks above the sequence (44). Leucine 105 (underlined) is substituted with a phenylalanine in the LEF-4 ts virus.

Figure 16:
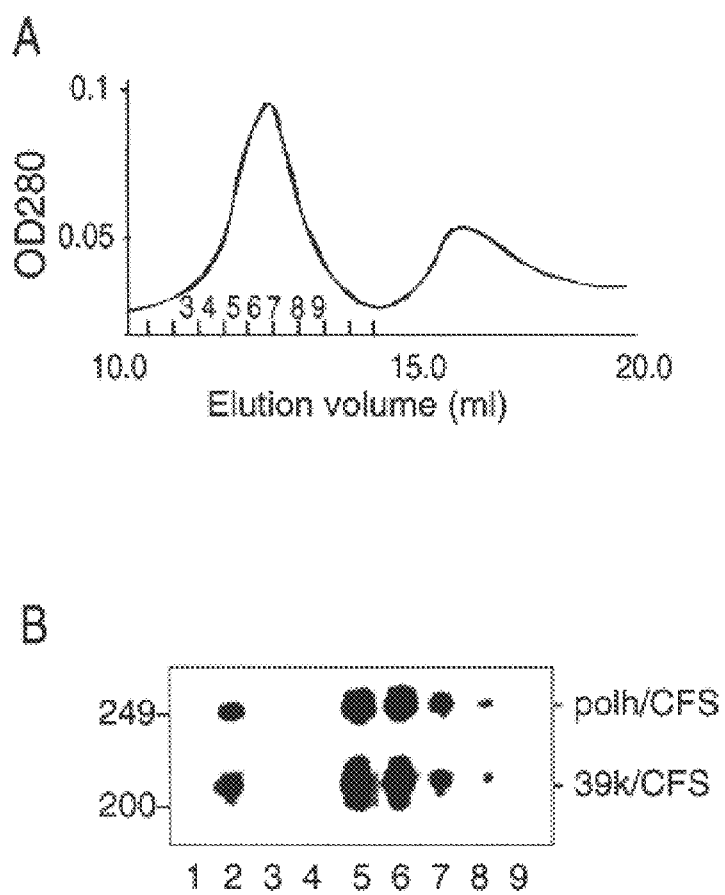
Figure 16:
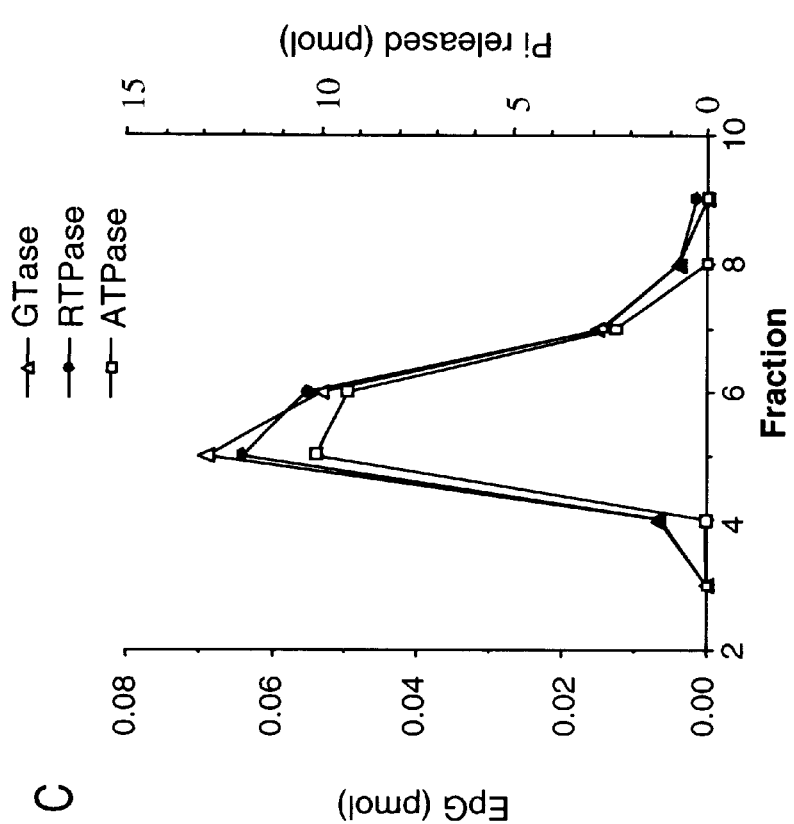

FIG. 16. RNA triphosphatase and ATPase activities of baculovirus RNA polymerase. (A) Gel filtration chromatography of RNA polymerase. RNA polymerase was filtered through Superose 6 as previously described (13). OD280, optical density at 280 nm. (B) In vitro transcription. Fractions corresponding to the peak of absorbance at 280 nm were assayed for in vitro transcription. The positions of molecular size markers are shown in kilodaltons on the left. The radiolabeled products corresponding to initiation from the polyhedrin (polh/CFS) and 39k (39k/CFS) promoters are shown on the right. (C) Guanyltransferase, RNA triphosphatase (RTPase), and ATPase assays. Guanylyltransferase mixtures (25 μl) contained 50 mM Tris HCl (pH 7.9), 5 mM DTT, 1 μM [α-$^{32}$P]GTP, 1 mM MnCl2, and 2 μl of each fraction. Reactions were incubated at 30° C. for 15 min, stopped by the addition of 1% SDS, and separated on an 8% polyacrylamide gel. RNA triphosphatase mixtures (10 μl) contained 50 mM Tris HCl (pH 7.9), 5 mM DTT, 1 mM MnCl$_2$, 1 μM (5' termini) γ-$^{32}$P-labeled RNA, and 0.2 μl of each fraction. Reactions were incubated at 30° C. for 15 min, stopped by the addition of 1 M formic acid, spotted on the PEI-cellulose plates, and quantitated by scanning in a PhosphorImager. Picomoles of phosphate released is plotted on the right. ATPase mixtures (10 μl) contained 50 mM Tris HCl (pH 7.9), 5 mM DTT, 1 mM MnCl$_2$, 1 μM [γ$^{32}$P]ATP, and 0.2 μl of each fraction. Δ, EpG; ● and □, Pi released.

Figure 17:
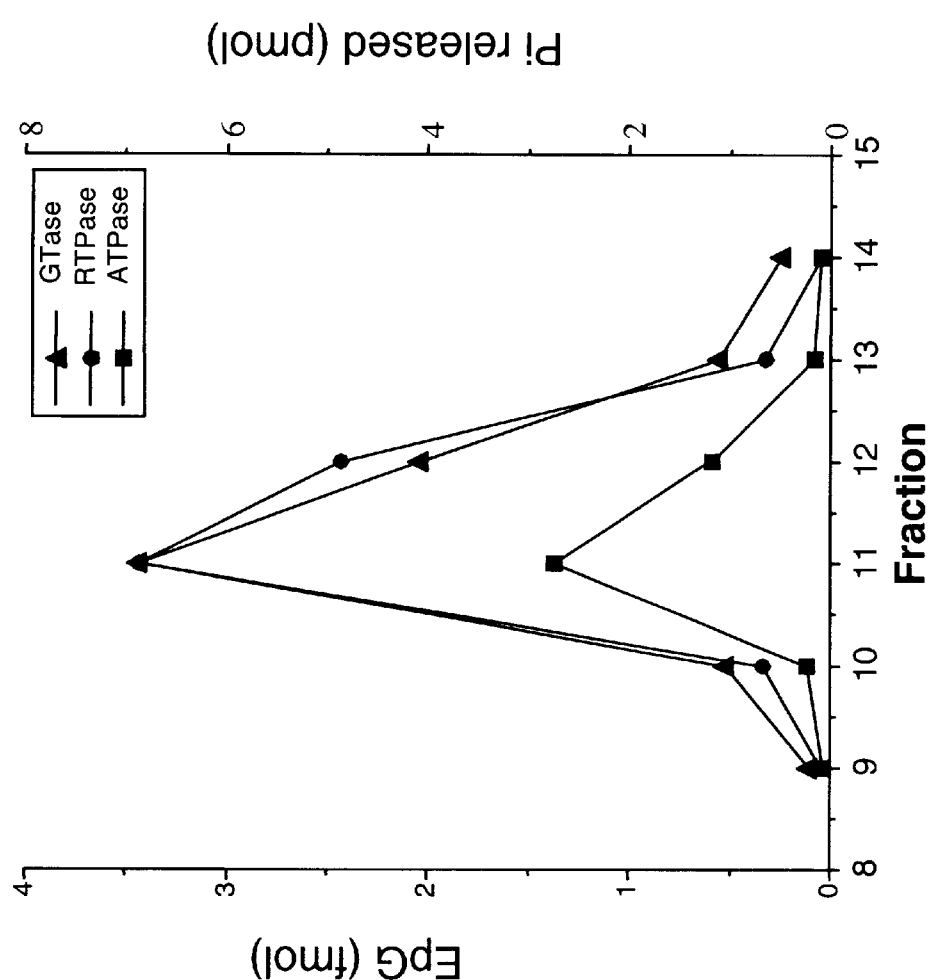

FIG. 17. RNA triphosphatase and ATPase activities of LEF-4. LEF-4 was purified by recombinant baculovirus-infected cells and filtered through Superdex 200 as previously described. Fractions corresponding to the peak of absorbance at 280 nm were assayed for guanylyltransferase, RNA triphosphatase (RTPase), and ATPase activities. Guanylyltransferase activity is plotted on the left; picomoles of phosphate released from gamma-labeled RNA or ATP is plotted on the right. Δ, EpG; ● and □, Pi released.

Figure 18:
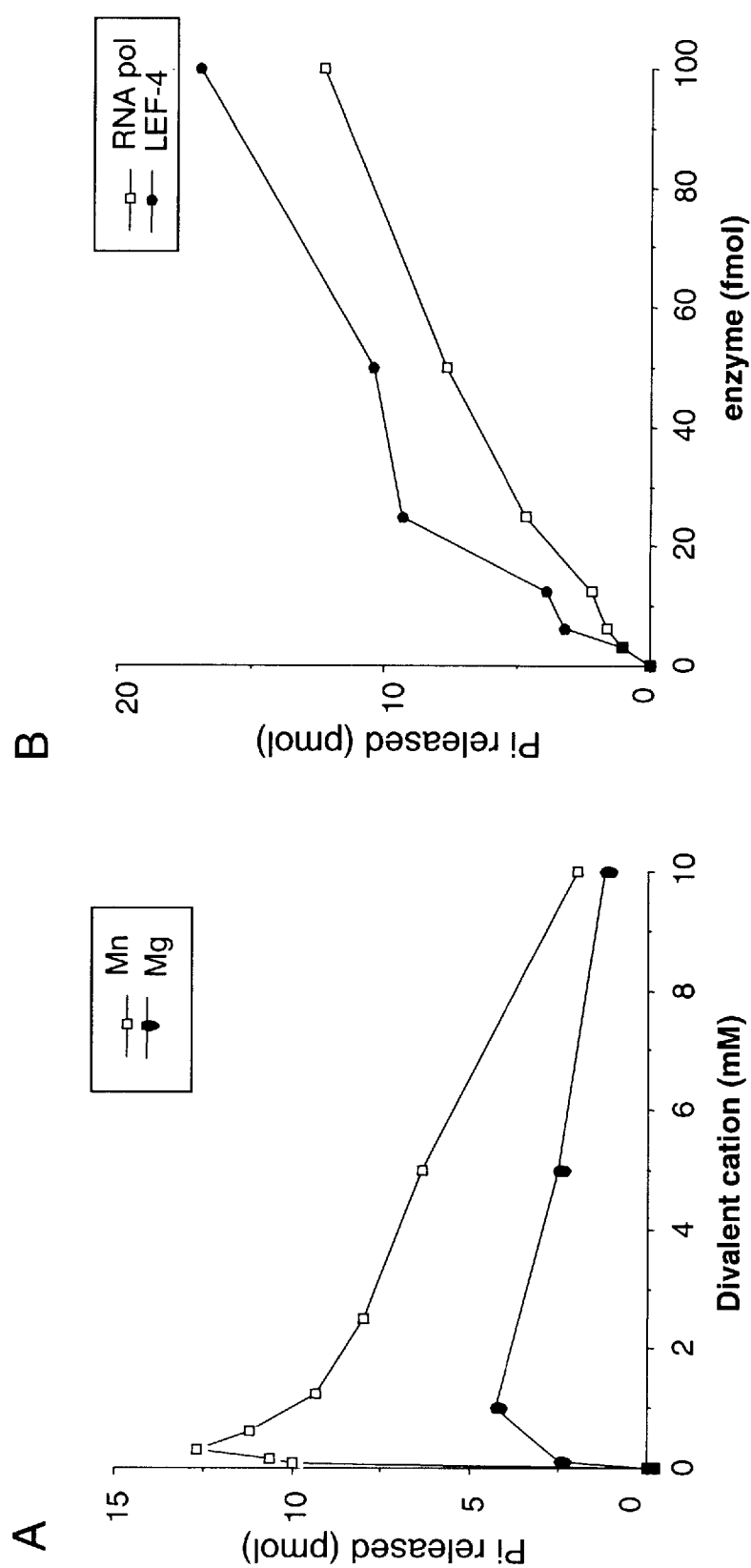

FIG. 18. Characterization of the RNA triphosphatase activity of LEF-4. (A) Cation requirements. Reaction mixtures contained 50 mM Tris HCl (pH 7.9), 5 mM/DTT, 1 μM (5' termini) γ-$^{32}$P-labeled RNA, 0.1 pmol of LEF-4, and divalent cation as indicated in 20 μl. Reactions were incubated at 30° C. for 15 min, spotted on PEI-cellulose plates, and quantitated by scanning in a PhosphorImager. Picomoles of phosphate released is plotted as a function of magnesium or manganese concentration. (B) Protein titration. Reaction mixtures (20 μl) contained 50 mM Tris HCl (pH 7.9), 5 mM DTT, 1 μM γ-$^{32}$P-labeled RNA, 0.3 mM MnCl$_2$, and AcNPV RNA polymerase or LEF-4 purified from baculovirus-infected insect cells as indicated. Picomoles of phosphate released is plotted as a function of input protein.

Figure 19:
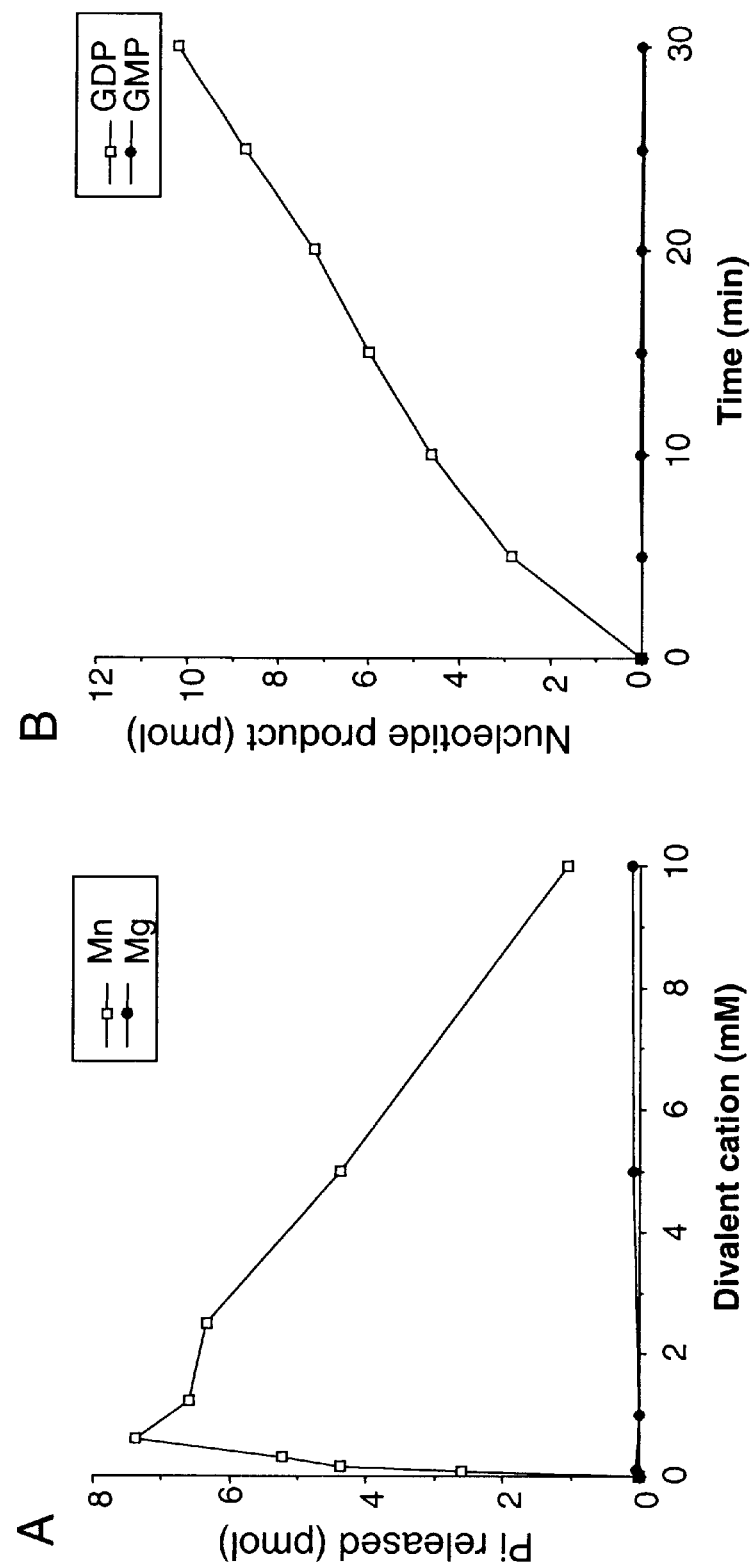

FIG. 19. Characterization of the nucleoside triphosphatase activity of LEF-4. (A) Cation requirements. Reaction mixtures contained 50 mM Tris HCl (pH 7.9), 5 mM DTT, 1 μM [α-$^{32}$P]ATP, 0.2 pmol of LEF-4 purified from baculovirus-infected cells, and divalent cation as indicated in 20 μl. Reactions were incubated at 30° C. for 15 min, spotted on PEI-cellulose plates, and quantitated by scanning in a PhosphorImager. Picomoles of phosphate released is plotted as a function of magnesium or manganese concentration. (B) Phosphate specificity. Reaction mixtures contained 50 mM Tris HCl (pH 7.9), 5 mM DTT, 1 μM [α-$^{32}$P]GTP, 0.3 mM MnCl2, and 0.2 pmol of LEF-4 purified from baculovirus-infected cells in 20 μl. Picomoles of GDP or GMP produced is plotted as a function of input protein.

Figure 20:
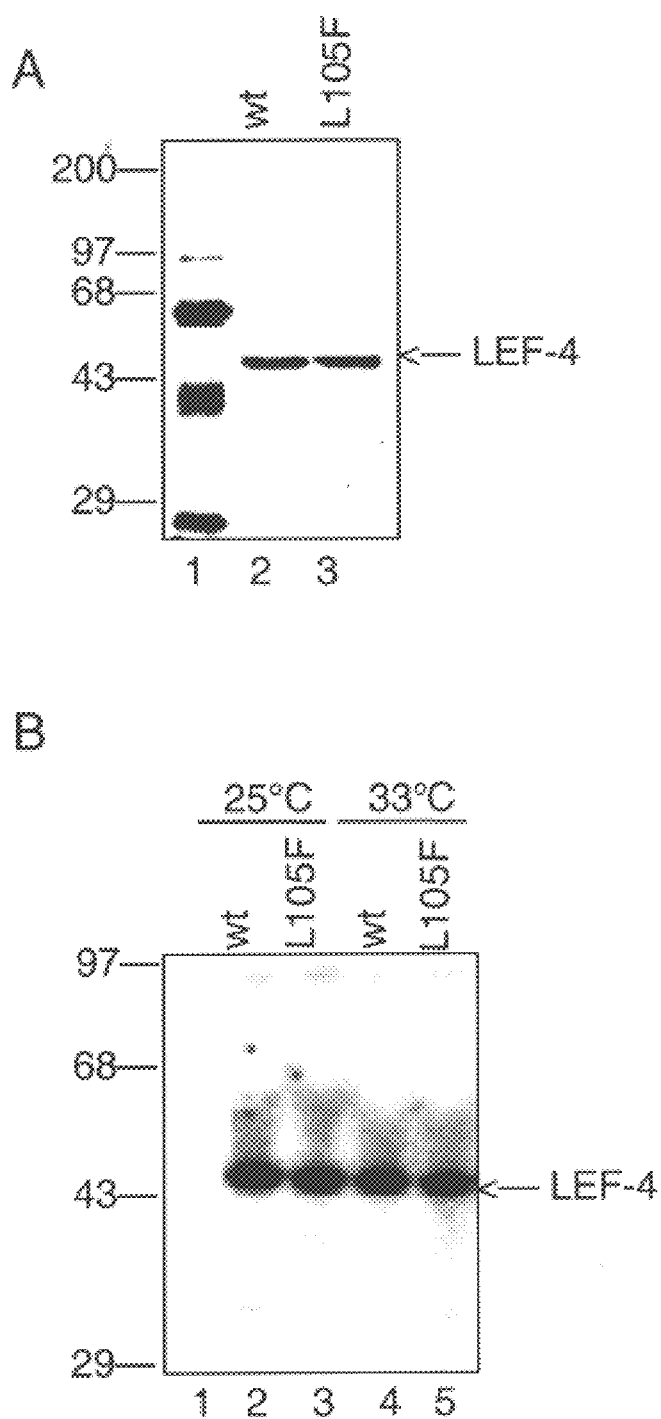

FIG. 20. Purification and guanylyltransferase activities of LEF-4 mutants. (A) SDS-PAGE analysis of wild-type (wt) and mutant (E9/11 A, R51A, K255A, and E181/183A) proteins purified from bacteria. Protein (1.35 μg per lane) purified by Mono Q chromatography was analyzed on SDS-8% polyacrylamide gels. The migration of prestained molecular markers is indicated on the left. (B) (Guanylyltransferase assays. Guanylyltransferase activities were measured by formation of a covalent enzyme-GMP complex. Reaction mixtures (25 μl) contained 50 mM Tris (pH 7.9), 5 mM DTT, 5 mM MnCl2, 1 μM [$^{32}$P]GTP, and 0.1 μg of the indicated protein. Reactions were stopped by the addition of 1% SDS and electrophoresed through an SDS-8% polyacrylamide gel. The positions of $^{14}$C-labeled protein markers are shown in kilodaltons on the left. The position of LEF-4 is indicated on the right.

Figure 21:
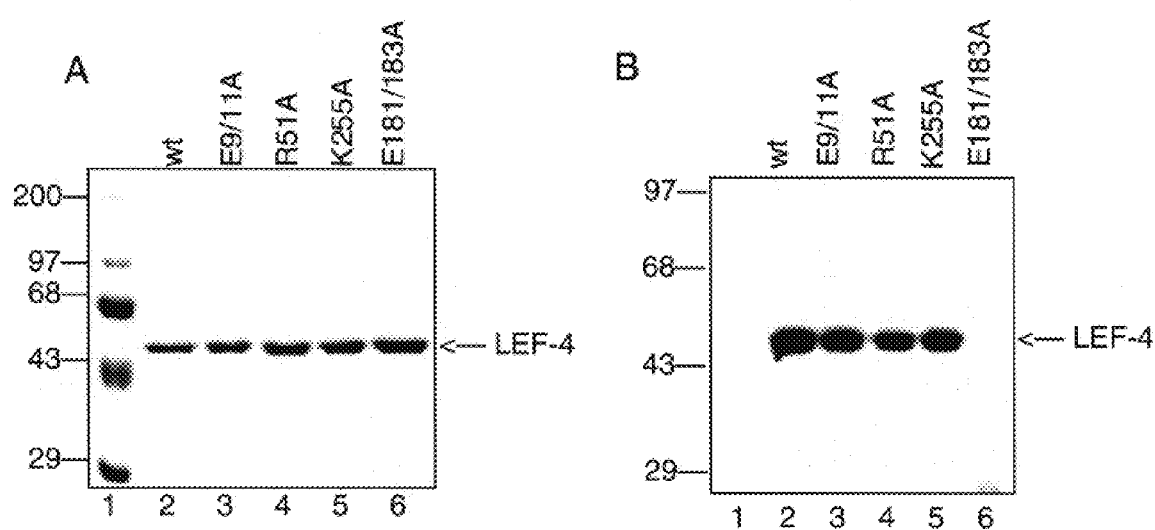

FIG. 21. Characterization of the L105F protein. (A) SDS-PAGE analysis wild-type (wt) and L105F mutant LEF-4 proteins purified from bacteria. Protein (1 µg per lane) purified by Mono Q chromatography was analyzed on SDS-8% polyacrylamide gels. The migration of prestained molecular markers is indicated in kilodaltons on the left. (B) Guanylyltransferase assays. Guanylyltransferase activities were measured by formation of a covalent enzyme-GMP complex. Reactions mixtures (25 µl) contained 50 mM Tris (pH 7.9), 5 mM DTT, 5 mM MnCl$_2$, 1 µM [$^{32}$P]GTP, and 0.1 µg of the indicated protein. Reactions were incubated for 15 min at 25° C. (lanes 2 and 4) or 33° C. (lanes 3 and 5), stopped by the addition of 1% SDS, and electrophoresed through an SDS-8% polyacrylamide gel. The positions of $^{14}$C-labeled protein markers are shown in kilodaltons on the left. The migration of LEF-4 is indicated on the right.

Figure 22:
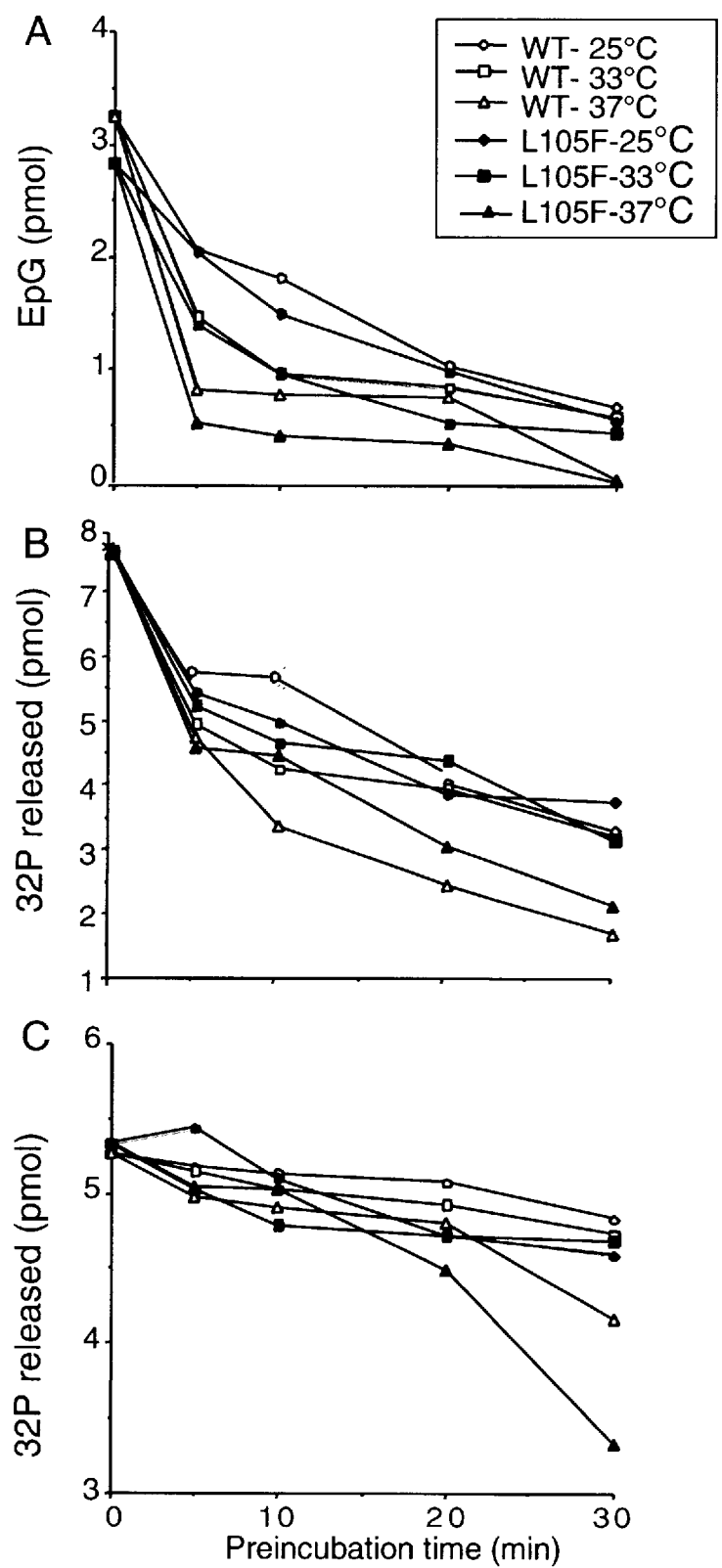

FIG. 22. Thermal stability of LEF-4 L105F. (A) Guanylyltransferase assays. Guanylyltransferase activities were measured by formation of a covalent enzyme-GMP complex. Reactions mixtures (25 µl) contained 50 mM Tris (pH 7.9), 5 mM DTT, 5 mM MnCl$_2$, 5 µM [$^{32}$P]GTP, and 0.01 µM wild-type (WT) or L105F protein. After incubation the absence of GTP for the indicated times at 25, 33, or 37° C. , the samples shifted to 25° C., GTP was added, and the samples were incubated for 15 min. Reactions were quantitated by scanning SDDS-protein gels in a PhosphorImager. EpG, LEF-4. (B) ATPase assays. Reaction mixtures (20 µl) contained 50 mM Tris HCl (pH 7.9), 5 mM DTT, 1 µM [γ-$^{32}$P]ATP, 0.3 mM MnCl2 and 0.01 µM of wild-type or L105F protein. (C) RNA triphosphatase assays. Reaction mixtures (20 µl) contained 50 mM Tris HCl (pH 7.9), 5 mM DTT, 1 µM γ-$^{32}$P-labeled RNA, 0.3 mM MnCl$_2$, and 5 nM of wild-type or L 105F protein. Samples for RNA triphosphatase and ATPase activities were incubated for the indicated amounts of time at 25, 33, or 37° C. in the absence of substrate; then the samples were shifted to 25° C., RNA or ATP was added, and the samples were incubated for 15 min. Reactions were quantitated by scanning TLC plates in a PhosphorImager. Each point represents the average of triplicate reactions.

Figure 23:
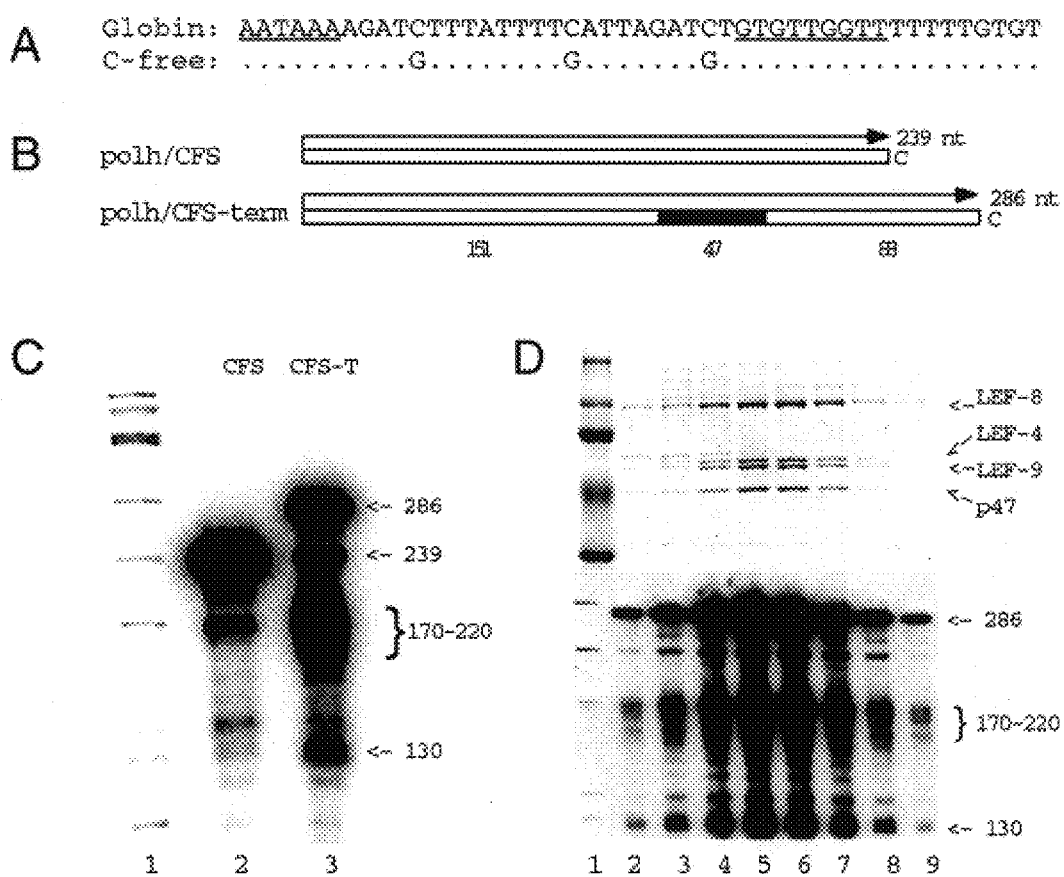

FIG. 23. The globin cleavage/polyadenylation signal is recognized by purified baculovirus RNA polymerase. (A) Sequence of the globin cleavage/polyadenylation signal. To all transcription in the absence of CTP, the three C's on the nontemplate strand of the globin sequence were changed to G. (B) Schematic diagram of transcription templates Polh/CFS and Polh/CFS-T. (C) RNA transcription pattern. Purified RNA polymerase (0.2 pmol) was incubated with 0.2 pmol of the indicated DNA template using standard transcription reaction conditions at 30° C. for 15 min. Lane 1 ΦX174/Hinfl marker; lane 2, Polh/CFS as template; lane 3, Polh/CFS-T as template. Sizes of the transcripts produced from Polh/CFS (left) and Polh/CFS-T (right) are indicated. (d) Transcription termination actively copurified with baculovirus RNA polymerase. RNA polymerase was filtered through a Superose 6 size exclusion column. Fractions were collected and dialyzed individually against polymerase storage buffer (60 mM Tris [pH 7, 9], 400 MM KCl, 0.1 mM EDTA, 1 mM DTT, 50% glycerol). Fractions across the peak of RNA polymerase were analyzed by SDS-PAGE followed by straining with Coomassic brilliant blue (top). The same fractions were assayed for transcription termination using 2 ul from each fraction and 1.0 mg of Polh.CFS-T as template. The RNA transcripts were resolved on a 6% polyacrylamide-8M urea gel and exposed to X-ray film. Lane 1 contains protein (top) or DNA (bottom) molecular markers.

Figure 24:
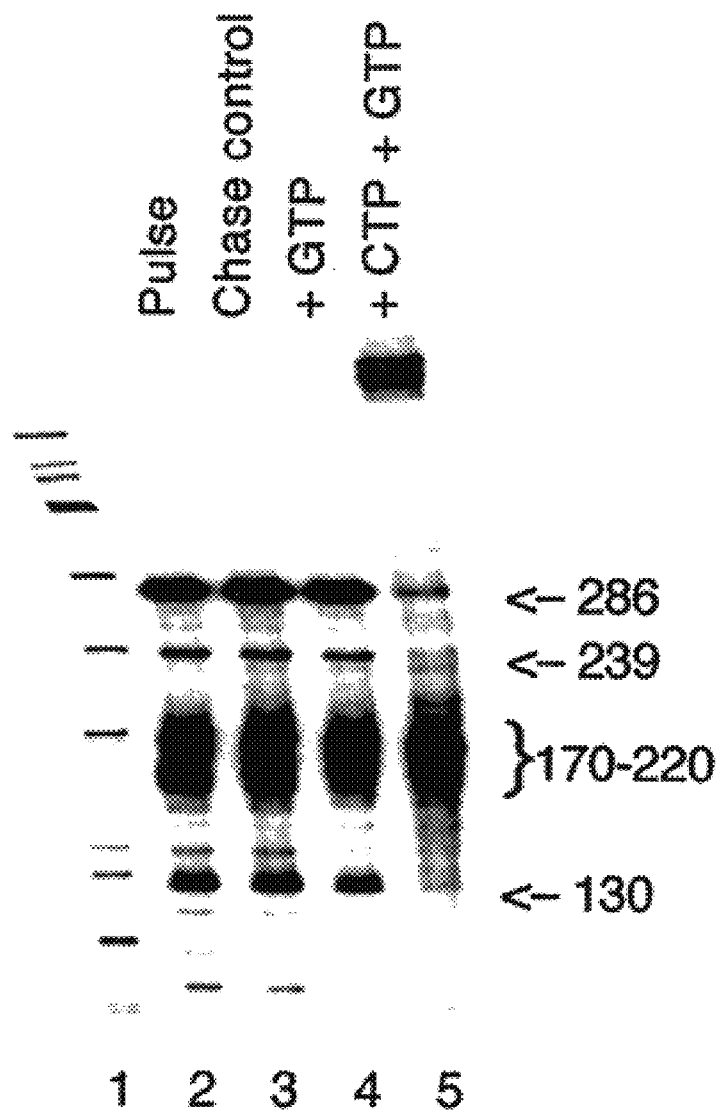

FIG. 24. Terminated transcripts are released from ternary complexes. After a 15-min transcription reaction, parallel transcription reactions were topped immediately (lane 2) or chased for 5 min at 30° C. with 1 mM GTP (lane 4), 1 mM GTP plus 1 mM CTP (lane 5), or an equivalent volume of transcription buffer (land 3). Sizes are indicated in nucleotides.

FIG. 25. Mapping of terminated transcripts. (A) Schematic diagram of Polh/CFS-Tit the relative positions of the 5' and 3' probes indicated. (B) Transcription reactions, RNA transcripts were resolved on a 6% polyacyiamide-8 M urea gel, transferred to a nylon membrane, and detected by exposure to X-ray film, Lanes: M, φX174/Hinfl marker, 1 and 3, Polh/CFS as template; 2 and 4, Polh/CFS-T as template. (C) Northern blot analysis. The nylon membrane was hybridized with hintin-labeled probes and directed using alkaline phosphatose-conjugated strepravidin and a chromogenic substrate. Sizes are indicated in nucleotides.

Figure 26:
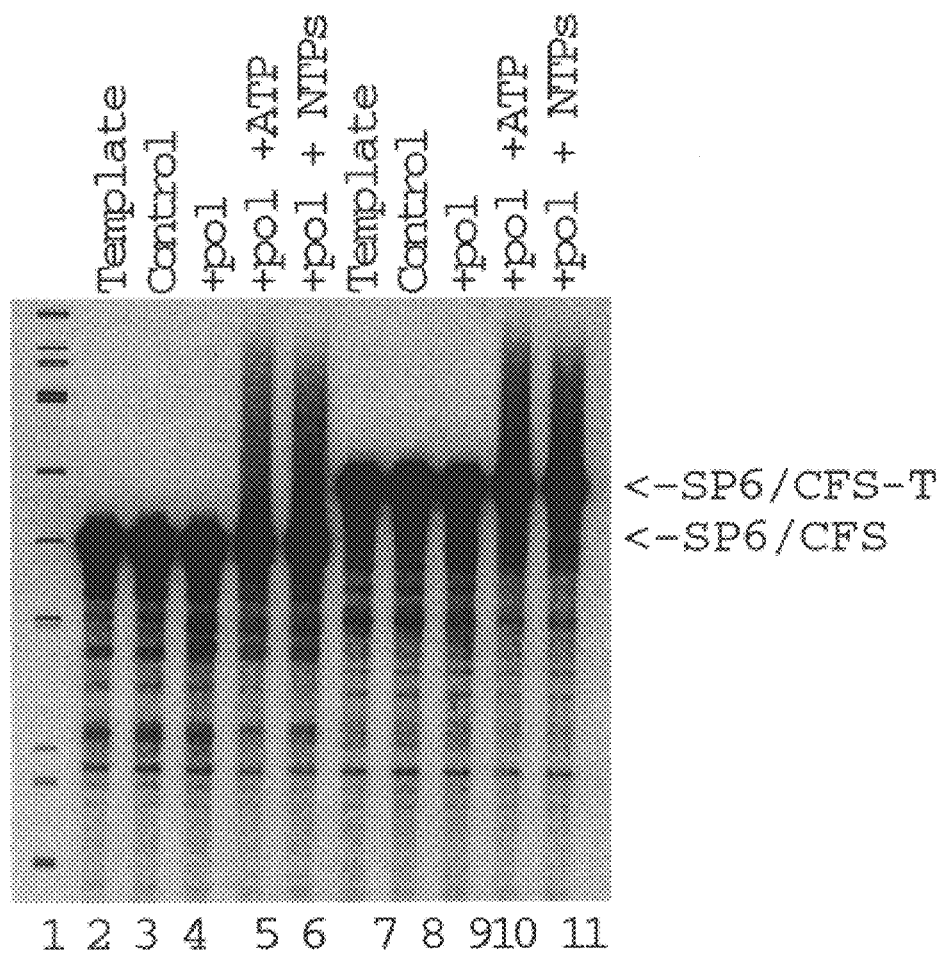

FIG. 26. Cleavage and polyadenylation activities of purified baculovirus RNA polymerase. The two C-free cassettes were cloned under the control of the SP6 promoter, and RNA was produced in vitro using SP6 RNA polymerase. Ten fenitomoles of each RNA was analyzed directly or incubated at 30° C. for 15 min in transcription buffer with RNA polymerase and nucleotides as indicated. The samples were then were extracted with phenol and chloroform, precipitated with ethanol, and resolved on 6% polyacrylamide-S M urea gel. Lanes: 1. φX174/Hinfl marker, 2 and 7, SP6 RNA transcripts; 3 and 8, buffer only; 4 and 9, RNA polymerase; 5 and 10, RNA polymerase plus 1 mM ATP; 6 and 11, RNA polymerase plus 1 mM ATP and UTP plus 20 µM GTP.

Figure 27:
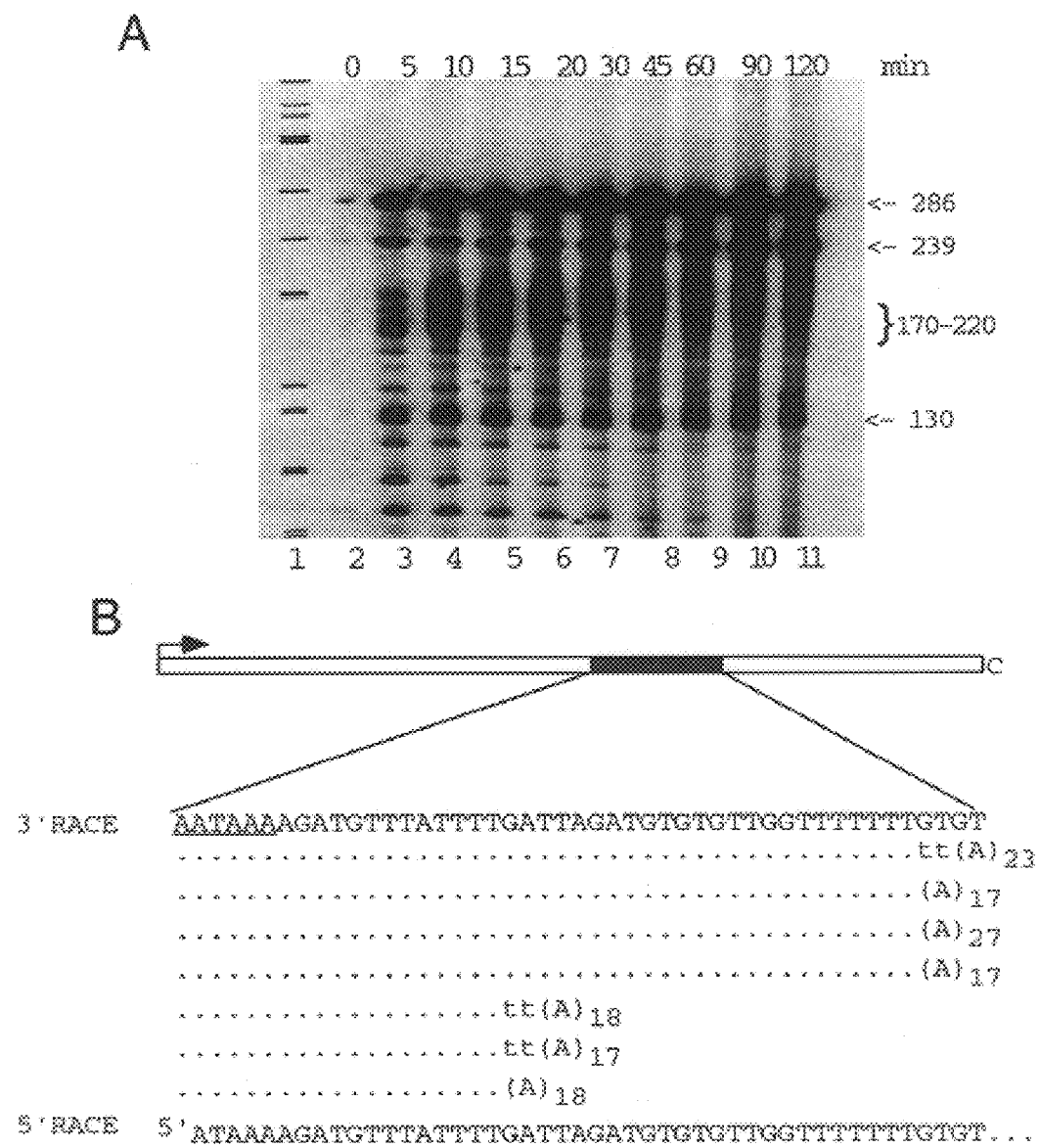

FIG. 27. Terminated transcripts are polyadenylated. (A) Time course of transcription and polyadenylation. In vitro transcription reactions with Poly/CFS-T and purified RNA polymerase were stopped at the times and indicated above the lanes. RNA transcripts were resolved on a 6% polyacrylamide-S M urea gel. Lane 1, φX174/Hinfl marker. Positions of the relevant transcripts are indicated in nucleotides on the right. (B) Sequences of cDNA clones, RNA 3' RACE and cDNA sequencing were used to determine the sites of transcription termination. The sequence corresponds to the nontemplate strand of the globin cleavage/polyadenylation signal in polh/CFS-T; the poly(A) signal is underlined. The viral RNA polymerase terminates at the end of two T-rich sequences in the globin sequence. Three clones contained two nontemplated T residues before the poly(A) tails.

Figure 28:
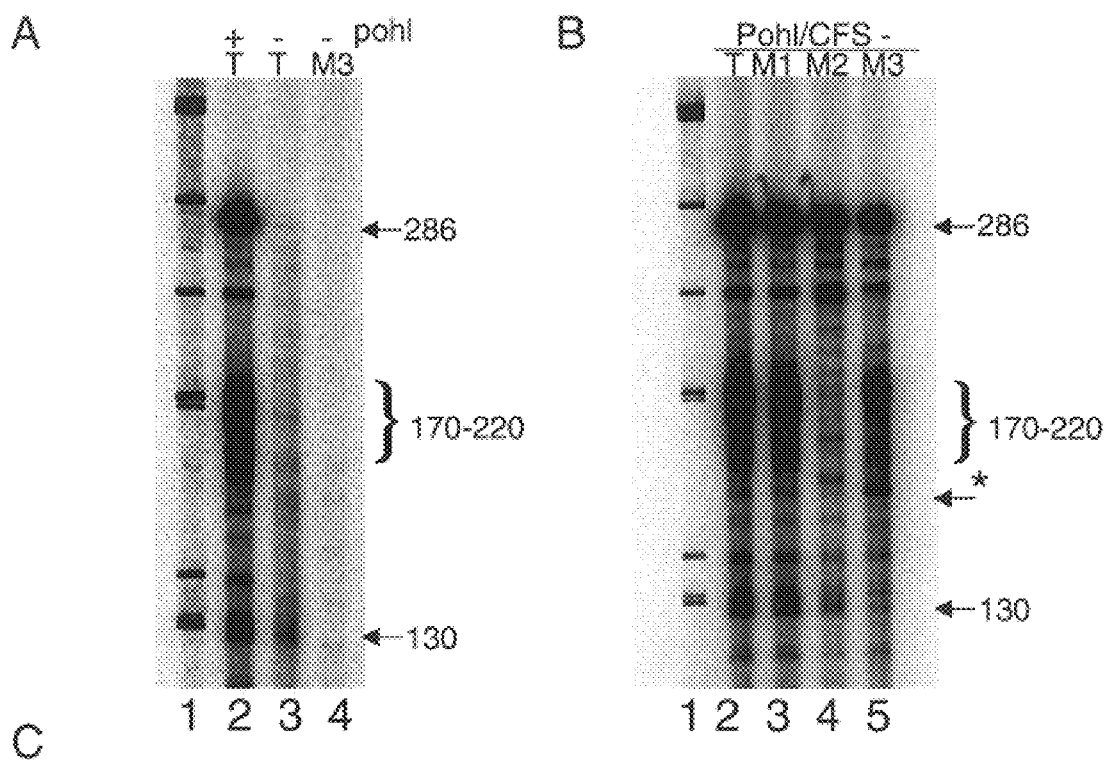

FIG. 28. Mutational analysis of globin cleavage/polyadenylation cassette. (A) Nonspecific transcription initiation at the globin poly(A) signal. Standard in vitro transcription reactions were carried out with 0.2 pmol of purified RNA polymerase and 0.2 pmol of the indicated templates at 30° C. for 15 min. Lanes: 1, φX174/HinFl marker, 2, Polh/CFS-T; 3, SP5/CFS-T; 4, SP6/Polh-M3 as template in which AATAAA was changed to AGGAAA in the C-free cassette. Sizes are indicated nucleotides. (B) Sequence requirements for termination. Lanes 1, φX174/Hinfl marker, 2, RNA transcripts synthesized from Polh/CFS-T plasmid; 3, RNA transcripts from Polh/CFS-M1 plasmid; 4, RNA transcripts from Polh/CFS-M2 plasmid; 5, RNA transcripts from Polh/CFS-T3 plasmid. (C) Sequences of the globin cleavage/polyadenylation cassette and three mutant versions. The relevant substituted regions are underlined.

Figure 29:
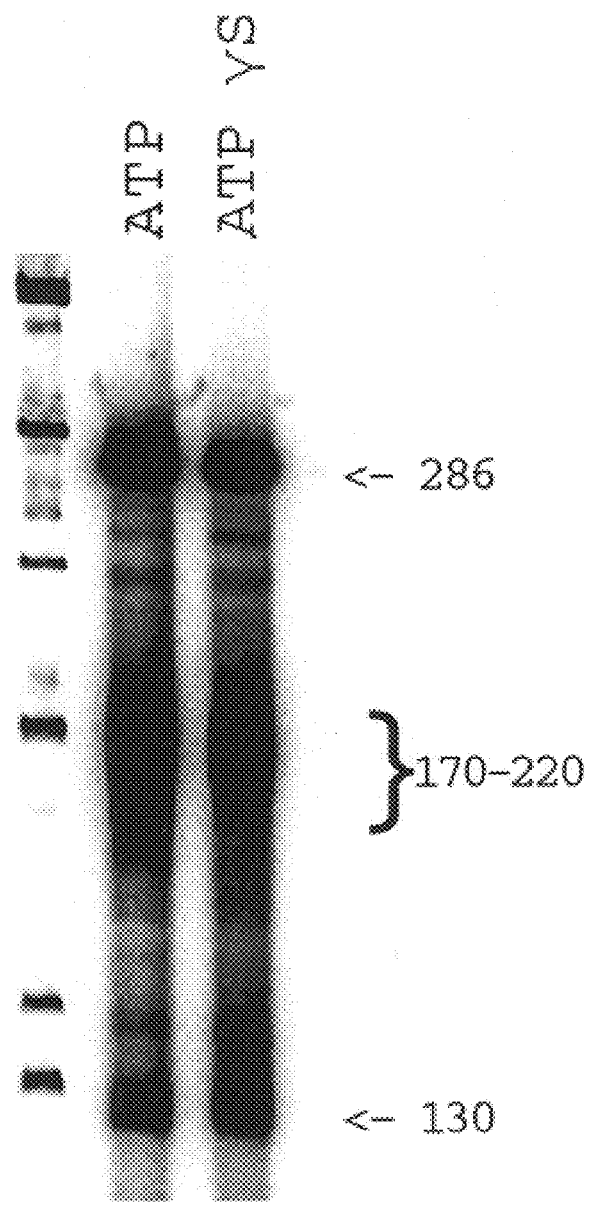

FIG. 29. ATP hydrolysis is not required for transcription termination by baculovirus RNA polymerase. Purified RNA polymerase (0.3 pmol) was incubated with 0.2 pmol of Polh/CFS-T plasmid at 30° C. for 60 min in standard transcription buffer containing 1 mM ATP (land 2) or 1 mM ATPγs to replace ATP. Lane 1. φX174/Hinfl marker. Sizes are indicated in nucleotides.

Figure 30:
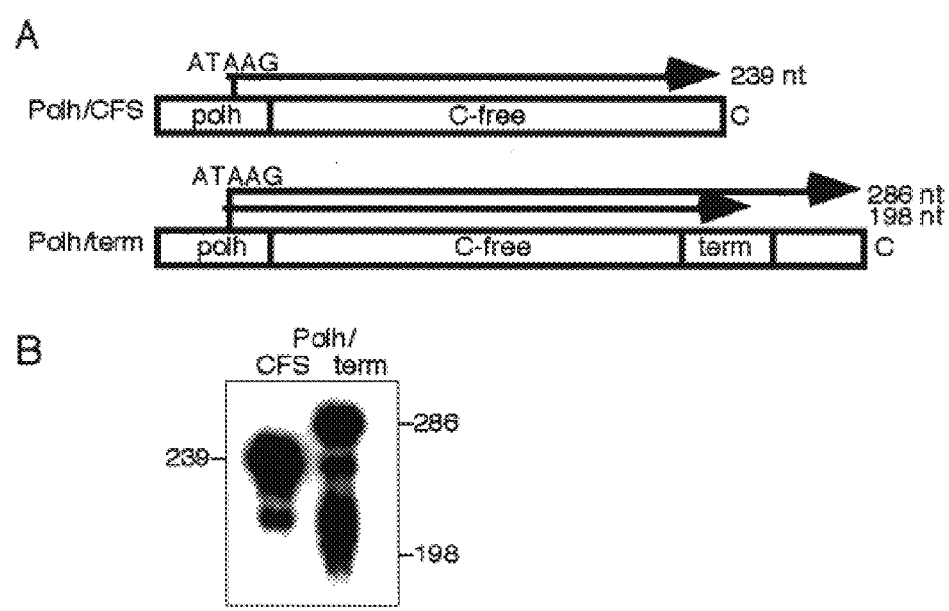

FIG. 30. In vitro transcription using the polyhedrin termination templates. Panel A shows the essential features of Polh/CFS and Polh/tern and indicates the expected sizes transcripts made by initiation at the ATAAG motif and pausing at the first C residue downstream of the C-free cassette. Panel B shows the results obtained after transcription with purified baculovirus RNA polymerase.

FIG. 31. Sequence of the globin termination signal. Sequencing of clones from 3'RACE revealed that the termination sites were heterogeneous and mapped to the two underlined regions of the globin sequence. All clones contained a polyA tails.

Figure 32:
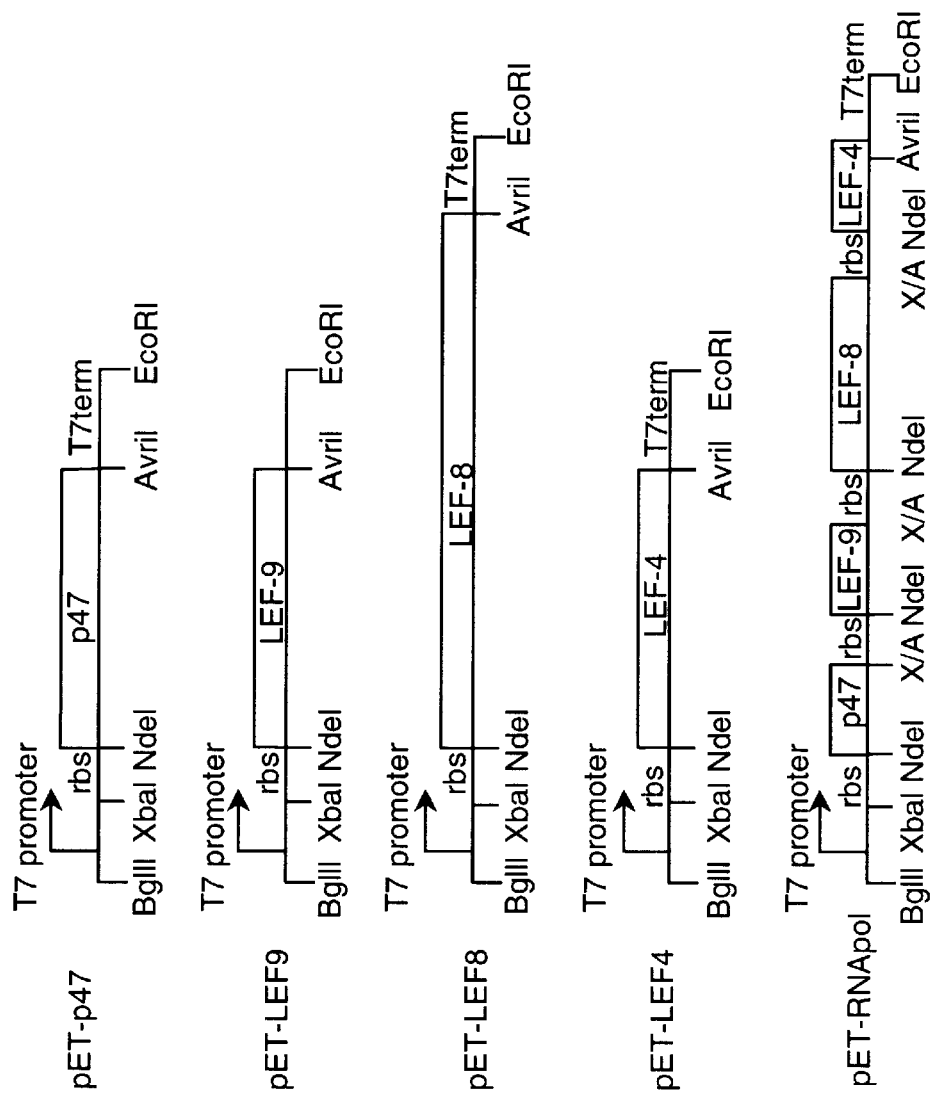

FIG. 32. Construction of pET-RNApol. The four subunits of RNA pol were separately cloned into pET expression vectors in an orientation that yielded Ndel sites at the start of translation and an Avrll site immediately downstream of each open reading frame. The ribosome binding site (rbs) is located between the Xbal site and the Ndel site of each plasmid. The T7 transcription terminator (T7 term) is located downstream of Avrll. Then the Xbal and Avrll fragment of pET-LEF9 was cloned into the resulting construct, followed by the LEF4 fragment in the same manner. The final plasmid pET-RNApol is not drawn to the same scale as the other four.

Figure 33:
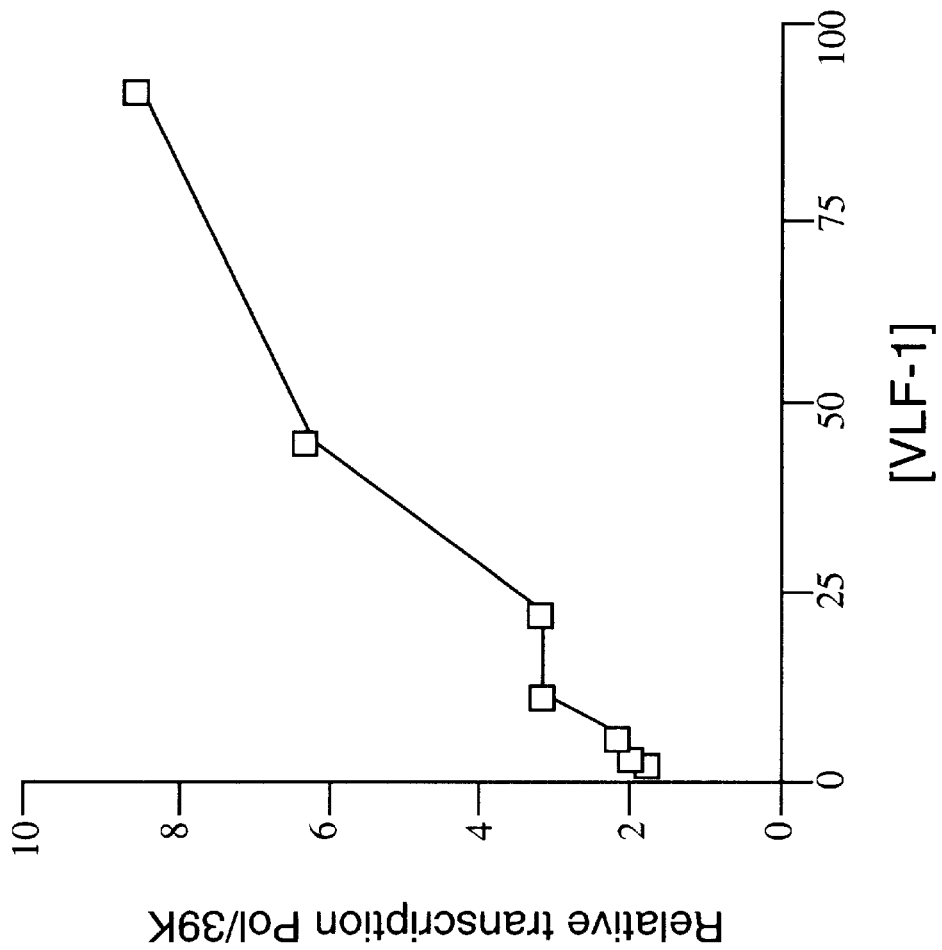

FIG. 33. VLF. VLF-1 increases transcription from the polh promoter and represses 39k transcription. His-tagged VLF-1 was expressed in bacteria and purified by affinity chromatography, followed by cation exchange chromatography. VLF-1 was added in a range of concentrations corresponding to equimolar to 90-fold molar excess of VLF-1 to RNA polymerase. All reactions contained polh/CFS and 39k/CFS. The amounts of RNA transcribed from each template were quantitated by PhosphorImager analysis and the results are plotted as the amount of polh transcript divided the amount of 39k transcript.

Figure 34:
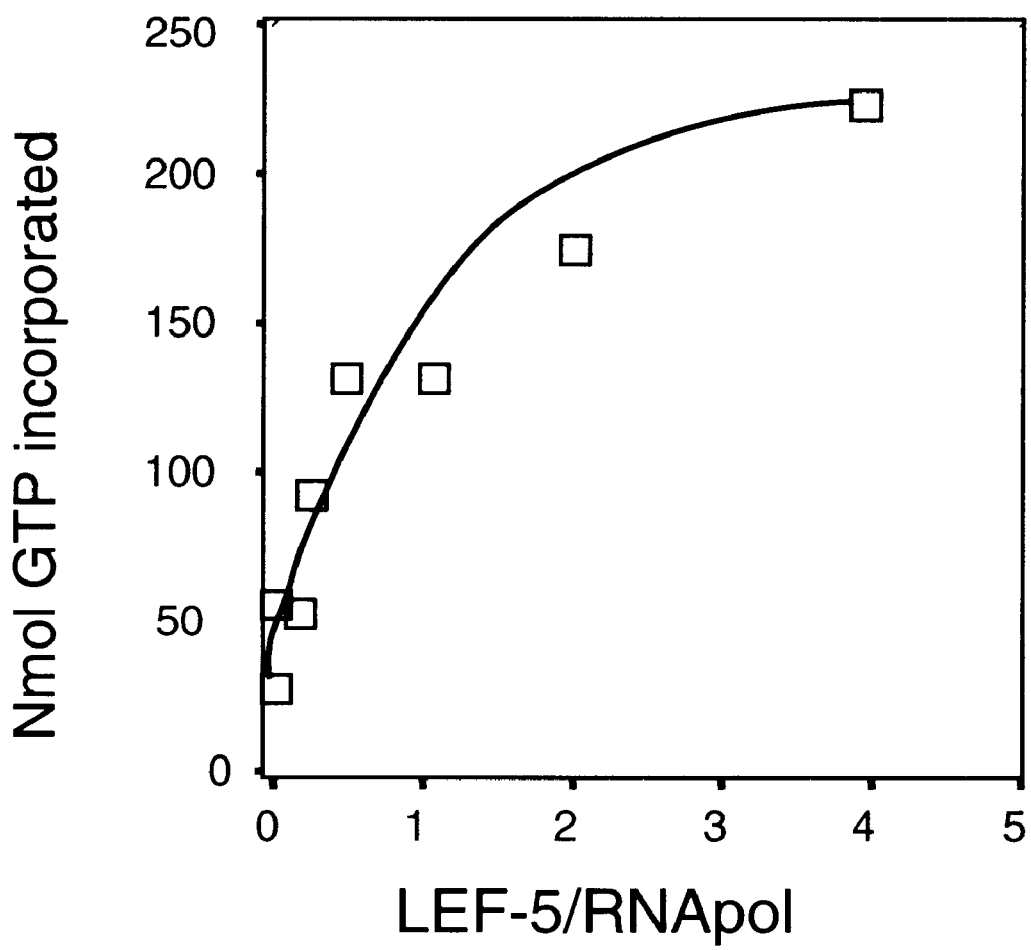

FIG. 34. LEF5, LEF-5 increases RNApol transcription activity. Titrated amounts urified LEF-5 was added to purified RNA polymerase and transcription templates. RNA products were quantitated by PhosphorImager analysis, and the results are plotted as amount of product produced as a function of LEF-5 concentration.

DESCRIPTION OF ILLUSTRATIVE EMBODIMENTS

An object of the present invention herein is the observation and discovery that baculovirus RNA polymerase can be used to cap RNAs in vivo and in vitro.

Of the many advantages of the use of the present invention over the prior art, one advantage is that the use of baculovirus RNA polymerase to cap and polyadenylate RNAs, especially in vitro, is cheaper than using capping enzymes that utilize rGTP than with bacteriophage RNA polymerase plus GpppG (an expensive analog required in high concentrations). Other potential uses of the present invention are for researchers who rely on the baculovirus expression vector system. For example, the baculovirus RNA polymerase can be used to verify that constructs are correct before making recombinant baculoviruses, wherein it would be relatively short time frame to verify constructs by RNA polymerase (days) as opposed to weeks to prepare recombinant baculoviruses.

Kits

It is contemplated that the present invention may be used to develop baculovirus RNA polymerase as a commercial tool for the production of capped and polyadenylated transcripts for research and diagnostic applications. There are a number of advantages to the use of baculovirus RNA polymerase as compared to current protocols using bacteriophage RNA polymerases, cap analog, and templated poly(A) tails. 1) Production of capped RNAs would be cheaper because rNTPs could be used instead of cap analog. 2) Production of capped RNAs would be more efficient because transcription reactions could be done at optimal GTP concentrations since there is no competition between GTP and cap analog—the yield of RNA would be increased as well as the proportion of capped RNAs. 3) Polyadenylation of transcripts made in vitro should offer increased efficiency of translation, as well as increased stability. Polyadenylated tails would be longer than templated poly(A) tails and would also be authentic because they would not be terminated with a restriction enzyme site. 4) Supercoiled DNA could be used as template since baculovirus RNA polymerase can terminate and process transcripts at the 3' end. This would eliminate the need to linearize DNAs prior to in vitro transcription. 5) The problem of reverse caps would be eliminated since the mechanism of cap formation is the same as that used in vivo.

In one embodiment of the present invention, baculovirus may be used to cap transcripts, for example in vitro, using the following illustrative method. A target gene or sequence of choice is cloned into a plasmid containing a baculovirus promoter and terminator sequences. This uses technology known in the art and is similar to current protocols wherein target genes are cloned into plasmids containing bacteriophage promoters and terminators. The clone is then used to direct synthesis of RNA by adding polymerase, for example purified baculovirus RNA polymerase, and ribonucleotides. A major advantage of the present invention over the prior art is that the use of baculovirus RNA polymerase in the transcription automatically produces RNAs that are, efficiently, capped and polyadenylated. These capped and polyadenylated RNAs can then be used in a variety of uses in vivo and in vitro, especially uses where enhanced stability of RNAs is desirous.

It is contemplated that in vitro transcription or in vitro transcription/translation kit may be developed using the baculovirus RNA polymerase to cap and polyadenylate RNAs in vitro. In a non-limiting example, a baculovirus RNA polymerase or variant thereof, may be comprised in a kit. The kits thus comprise, in suitable container means, a baculovirus RNA polymerase and/or additional agents of the present invention necessary to produce a capped, polyadenylated RNA.

The kits may comprise a suitably aliquoted baculovirus RNA polymerase, and/or additional agent compositions of the present invention, including but not limited to labeled or unlabeled labeled nucleotides, expression vectors, standards (e.g., positive and/or negative control DNA) or additional reagents necessary for transcription and/or translation, e.g. accessory proteins. The components of the kits may be packaged either in an aqueous solutions, e.g., RNase free $H_2O$ . The container means of the kits generally include at least one vial, test tube, flask, bottle or other container means, into which a component may be placed, and preferably, suitably aliquoted. Where there are more than one component in the kit, the kit also generally contain a second, third or other additional container into which the additional components may be separately placed. However, various combinations of components may be comprised in a vial. The kits of the present invention also typically include a means for containing the baculovirus RNA polymerase, additional agents, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

It is envisioned that the RNA transcripts produced by these kits may be used to generate probes for hybridization to Northern and Southern blots, plaque and colony lifts, tissue sections and chromosome spreads, S1 nuclease mapping, mRNA synthesis for in vitro translation, generation of antisense RNA to block translation or any other potential use for RNA transcripts.

Baculovirus RNA polymerase may also provide an improvement on coupled transcription-translation systems, which are marketed by several biotech companies. These are very convenient kits that allow for the production of mRNA and its subsequent translation in one tube. But, because cap analog inhibits translation, these systems are limited with respect capping. One solution to the problem is to perform the two reactions sequentially, so that the cap analog is depleted and can also be diluted prior to the translation reaction. Another alternative is to dispense with the cap analog and suffer lower translation efficiencies. This allows the reactions to be truly coupled as opposed to sequential, but the lower levels of product require a very sensitive means of detection. Baculovirus RNA polymerase would be a superior product for a coupled transcription-translation system because the two reactions could be done simultaneously since it does not rely on cap analog. Furthermore, the translational efficiency would b,e very high because all of the RNAs would be capped.

In addition, the inventors envision marketing a protein truncation test (PTT). This is a special type of coupled transcription-translation kit that is marketed as a medical diagnostic assay. This test was initially developed for use with Duchenne muscular dystrophy (Roest et al., 1993), and is now used for screening many different disease genes, including familial adenomatous polyposis, ataxia telangiectasia, hereditary breast and ovarian cancers, cystic fibrosis, neurofibromatosis, and polycystic kidney disease (Hogervorst, 1997). The PTT test is advantageous because the majority of mutations that have been found to cause these diseases result in premature termination of translation. Thus PTT, which can be used to rapidly screen multiple samples for the presence of translation terminating mutations, is the preferred diagnostic test. PTT selectively detects disease mutations and ignores polymorphisms and silent mutations, and so has replaced DNA, sequencing of entire genes in order to look for mutations.

The PTT procedure is outlined in FIG. 1. The first step involves the isolation of genomic DNA and amplification of the target gene coding sequences using PCR. Alternatively, RNA can be isolated and amplified using reverse transcription and PCR (RT-PCR). In either case, a promoter for bacteriophage T7 RNA polymerase is incorporated into the 5' end of the amplified target. The PCR products are then used as a template for the in vitro synthesis of RNA, which is subsequently or sequentially translated into protein in a rabbit reticulocyte extract. The final step is SDS-PAGE analysis of the synthesized protein. The shorter protein products of mutated alleles can be easily distinguished from the full-length protein products of normal alleles. The length of the truncated protein, combined with the knowledge of the protein pair that yielded the truncation, can be used to map the mutation site to within a few hundred base pairs.

A PTT test based on baculovirus RNA polymerase and either the yeast or Drosophila translation system should offer improved translation efficiency, greater sensitivity, and higher throughput as compared to PTT kits based on T7 polymerase and rabbit reticulocyte extracts.

II. In Nitro Transcription

Another embodiment of the present invention is that baculovirus RNA polymerase may be used for in vitro transcription. In vitro transcription assays are well known and used in the art (Sambrook et al., 1989). It is envisioned that baculovirus RNA polymerase may produce stable eukaryotic mRNA, e.g., capped and polyadenylated RNA.

It is well known and understood by those of skill in the art that there are some significant differences between prokaryotic and eukaryotic mRNA transcripts. Typically, eukaryotic mRNAs are characterized by two post-transcriptional modifications: a 5'-7 methyl-GTP cap and a 3' poly(A) tail. Both modifications contribute to the stability of the mRNA by preventing degradation. Additionally, the 5' cap structure enhances the translation of mRNA by helping to bind the eukaryotic ribosome and assuring recognition of the proper AUG initiator codon. This function may vary with the translation system and with the specific mRNA being synthesized. The consensus sequence 5'-GCCACCAUGG-3', also known as the "Kozak" sequence, is considered to be the strongest ribosomal binding signal in eukaryotic mRNA. For efficient translation initiation, the key elements are the G residue at the +1 position and the A residue at the −3 position. An mRNA that lacks the Kozak consensus sequence may be translated efficiently in eukaryotic cell-free systems if it possesses a moderately long 5'-untranslated region (UTR) that lacks stable secondary structure.

Typically, transcription reactions are performed at room temperature or at 37° C. or 30° C. for baculovirus RNA polymerase. Lowering the temperature to ~16° C. or even 4° C. can sometimes improve transcription. It is believed that lower reaction temperatures slow the polymerase's progression, thereby preventing it from being displaced by secondary structure or a string of one specific nucleotide.

A. DNA Templates

The preparation of the DNA does not need to be highly purified—crude minipreparations are acceptable. The essential requirement is that the template be free of RNase contamination. One technique that can be used to fulfill this criteria is by extracting the DNA preparation with phenol:chloroform.

Typically, the DNA templates are blunt-ended or should carry protruding 5' termini. Also, if the DNA template is contained within a plasmid, then the plasmid it is usually necessary to linearize the plasmid DNA in order to provide a means of terminating transcription. Otherwise, the result is extremely long transcripts that include plasmid sequences.

It is envisioned that the present invention may simplify the DNA template preparation. It is contemplated that the use of a baculovirus RNA polymerase eliminate the necessity of linearizing plasmid DNA because transcription stops at the termination sequence provided by the vector. Thus, eliminating the need for additional restriction enzymes and the time that is required for the restriction digest.

B. Transcription Reaction Mix

Transcription buffers may vary slightly depending on exact conditions, but typically the buffer contains 400 mM Tris, 60 mM $MgCl_2$, 20 mM spermidine and 50 mM NaCl. Spermidine or albumin may be added to the buffer to stimulate transcription. Dithiothreitol may also be included in the buffer.

In specific embodiments, the term transcription reaction mix or transcription reaction mix may be used. As used herein this term "transcription reaction mix or transcription mix" refers to the solutions that are necessary to perform transcription. Generally, it is considered to contain all the solutions except the polymerase and the DNA template. For example, the transcription mix may comprise a buffer, which contains, salts, buffering reagents, albumin, and/or DTT, and nucleotides.

Another embodiment of the reaction mixture is nucleotides. The nucleotide concentration should be at least 50 $\mu$M or greater to generate at least 90% of the transcripts as full-length transcripts. The nucleotides or NTPs comprise ATP, CTP, GTP, and UTP. It may be desirable to use a labeled NTP. Such labels include, but are not limited to $^{32}$P, $^{33}$P, $^{35}$S or $^{32}$S.

Transcription reactions that are done with the minimum concentration of labeled nucleotide may produce prematurely terminated transcripts because of insufficient nucleotide concentration. Thus, increasing the concentration of the limiting nucleotide often improves the yield of full-length transcripts.

In the present invention, the bacteriophage RNA polymerase, e.g. SP6, T3, or T7, is replaced with a baculovirus RNA polymerase. The baculovirus RNA polymerase produces mRNA that is capped and polyadenylated. To enhance transcription, accessory proteins may also be included in the reaction mix.

III. In Vitro Translation

The in vitro synthesis of proteins in cell-free extracts is an important tool for molecular biologists and has a variety of applications, including the rapid identification of gene products, localization of mutations through synthesis of truncated gene products, protein folding studies, and incorporation of modified or unnatural amino acids for functional studies. The use of in vitro translation systems can have advantages over in vivo gene expression when the overexpressed product is toxic to the host cell, when the product is insoluble or forms inclusion bodies, or when the protein undergoes rapid proteolytic degradation by intracellular proteases. In principle, it should be possible to prepare a cell-free extract for in vitro translation of mRNAs from any type of cells. In practice, only a few cell-free systems have been developed for in vitro protein synthesis. In general, these systems are derived from cells engaged in a high rate of protein synthesis.

The most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

One method is the use of rabbit reticulocyte lysate, which is a highly efficient in vitro eukaryotic protein synthesis system used for translation of exogenous RNAs (either natural or generated in vitro). In vivo, reticulocytes are highly specialized cells primarily responsible for the synthesis of hemoglobin, which represents more than 90% of the protein made in the reticulocyte. These immature red cells have already lost their nuclei, but contain adequate mRNA, as well as complete translation machinery, for extensive globin synthesis. The endogenous globin mRNA can be eliminated by incubation with $Ca^{2+}$-dependent micrococcal nuclease, which is later inactivated by chelation of the $Ca^{2+}$ by EGTA.

Wheat germ extract is another convenient alternative to the rabbit reticulocyte lysate cell-free system. This extract has low background incorporation due to its low level of endogenous mRNA. Wheat germ lysate efficiently translates exogenous RNA from a variety of different organisms, from viruses and yeast to higher plants and mammals. The wheat germ extract is recommended for translation of RNA containing small fragments of double-stranded RNA or oxidized thiols, which are inhibitory to the rabbit reticulocyte lysate. Both retic and wheat germ extracts translate RNA isolated from cells and tissue or those generated by in vitro transcription. When using RNA synthesized in vitro, the presence of a 5' cap structure may enhance translational activity.

*E. coli* cell-free systems consist of a crude extract that is rich in endogenous mRNA. The extract is incubated during preparation so that this endogenous mRNA is translated and subsequently degraded. Because the levels of endogenous mRNA in the prepared lysate is low, the exogenous product is easily identified. In comparison to eukaryotic systems, the *E. coli* extract has a relatively simple translational apparatus with less complicated control at the initiation level, allowing this system to be very efficient in protein synthesis. Bacterial extracts are often unsuitable for translation of RNA, because exogenous RNA is rapidly degraded by endogenous nucleases. There are some viral mRNAs (TMV, STNV, and MS2) that translate efficiently, because they are somewhat resistant to nuclease activity and contain stable secondary structure. However, *E. coli* extracts are ideal for coupled transcription:translation from DNA templates. Although, *E. coli* extracts are ideal, the mRNA is not capped unless a cap analog is added.

A disadvantage to all of these in vitro translation systems is that the RNA template must be clean. In other words, the RNA transcripts must be free of RNase, salt and free cap analog. Usually RNA transcripts are cleaned by concentrating and purifying the RNA using either ammonium acetate/ethanol or LiCl precipitation, and a subsequent 70% ethanol wash.

It may be desirable to include labeled amino acids. Typically, $^{35}$S-methionine is used because the endogenous pool of methionine in the lysate is low, and most proteins have methionine. Other amino acids suitable for use in labeling are cysteine, valine, leucine, isoleucine and phenylalanine. Both cysteine and methionine are synthesized with $^{35}$S, a strong β-emitter. The other amino acids can be obtained only with $^3$H or $^{14}$C labels, which would necessitate fluorography for quantitation purposes.

Some embodiments of the present invention refer to a translation mix. As used herein the term "translation mix" is defined as the solution that contains all the necessary reagents for in vitro translation. For example, the solution may contain buffers, salts, nucleotides, amino acids, and ribosomes. Those of skilled in the art are aware of the variations and the necessary reagents to translate proteins in vitro.

In standard translation reactions, purified RNA is used as a template for translation. "Linked" and "coupled" systems, on the other hand, use DNA as a template. RNA is transcribed from the DNA and subsequently translated without any purification. Such systems typically combine a prokaryotic phage RNA polymerase and promoter (T7, T3, or SP6) with eukaryotic or prokaryotic extracts to synthesize proteins from exogenous DNA templates. DNA templates for transcription:translation reactions may be cloned into plasmid vectors or generated by PCR.

The "linked" system is a two-step reaction, based on transcription with a bacteriophage polymerase followed by translation. Because the transcription and translation reactions are separate, each can be optimized to ensure that both are functioning at their fall potential. Conversely, many commercially available eukaryotic coupled transcription-:translation systems have compromised one or both reactions so that they can occur in a single tube. Thus, yield is sacrificed for convenience.

Unlike eukaryotic systems where transcription and translation occur sequentially, in *E. Coli*, transcription and translation occur simultaneously within the cell. In vitro *E. Coli* translation systems are thus performed the same way, coupled, in the same tube under the same reaction conditions. During transcription, the 5' end of the RNA becomes available for ribosomal binding and undergoes translation while its 3' end is still being transcribed. This early binding of ribosomes to the RNA maintains transcript stability and promotes efficient translation. This bacterial translation system gives efficient expression of either prokaryotic or eukaryotic gene products in a short amount of time. For the highest protein yield and the best initiation fidelity, make sure the DNA template has a Shine-Dalgarno ribosome binding site upstream of the initiator codon. Capping of eukaryotic RNA is not required. Use of *E. Coli* extract also eliminates cross-reactivity or other problems associated with endogenous proteins in eukaryotic lysates. Also, the *E. Coli* S30 extract system allows expression from DNA vectors containing natural *E. Coli* promoter sequences (such as lac or tac).

In bacteria, the ribosome is guided to the AUG initiation site by a purine-rich region called the Shine-Dalgarno (SD) sequence. This sequence is complementary to the 3' end of the 16s rRNA in the 30S ribosomal subunit. Upstream from the initiation AUG codon, the SD region has the consensus sequence 5'-UAAGGAGGUGA-3'. Specific mRNAs vary considerably in the number of nucleotides that complement the anti-Shine-Dalgarno sequence of 16S rRNA, ranging from as few as two to nine or more. The position of the ribosome binding site (RBS) in relation to the AUG initiator is very important for efficiency of translation (usually from −6 to −10 relative to the A of the initiation site).

It is contemplated in the present invention that the baculovirus RNA polymerase may be a better coupled system. It is envisioned that the baculovirus RNA polymerase resembles the prokaryotic polymerase system in that transcription and translation are coupled, however, it resembles a eukaryotic polymerase in that the RNA is capped and adenylated.

III. Vectors for Cloning, Gene Transfer and Expression

Within certain embodiments expression vectors are employed to express a polypeptide product or the subunits of baculovirus RNA polymerase. Further, accessory proteins may also be expressed by expression vectors. These vectors may be used for in vitro transcription, in vitro translation, and in cyto protein expression. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

1) Regulatory Elements

Throughout this application, the term "expression construct" or "expression cassette" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter is used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

One embodiment of the present invention includes the use of a baculovirus promoter. Any promoter from a late to a very late baculovirus gene may be used.

Another embodiment of the present invention includes that the baculovirus promoter comprises a consensus sequence. The consensus sequence is the sequence which the RNA polymerase recognizes and binds to initiate transcription. The consensus sequence for baculovirus is TAAG or any variant thereof that is a functional equivalent. A functional equivalent as used herein is a variant of the consensus sequence which retains functionality, e.g. the RNA polymerase recognizes the sequence, binds and transcription is initiated. In addition to the sequence TAAG, it is contemplated that the nucleotide before the T may be important, for example, A may be better than G, which may be better than C or T.

Also contemplated are additional sequences surrounding the TAAG and more specifically the -TAAG. It is considered that approximately 8–12 nucleotides on either side of the consensus sequence may influence transcription.

In certain embodiments, a baculovirus promoter may be used to drive expression of a nucleic acid sequence. In further embodiments, a baculovirus consensus sequence may be inserted into a promoter. This consensus sequence does not disrupt the function of the promoter. With the insertion of the consensus sequence, the modified promoter may be considered a dual promoter that would work in any system, prokaryotic or eukaryotic. One of skill in the art will realize that the use of baculovirus consensus sequence may be used in mammalian expression vectors to give the power of the baculovirus system, high level of expression, to mammalian cells.

One of skill in the art realizes that this may be accomplished by co-transfecting cells with two vectors. One vector may contain the nucleic acid sequence of interest inserted between a "modified promoter" and a baculovirus termination site. A modified promoter as used herein refers to any promoter sequence in which a baculovirus consensus sequence has been inserted. The second vector may contain the nucleic acid sequences encoding the four subunits of baculovirus RNA polymerase. Thus, in cyto, baculovirus RNA polymerase is synthesized, which can then bind and initiate transcription of the nucleic acid sequence of interest.

It is also contemplated that accessory proteins may be used. These accessory proteins may enhance transcription. For example, LEF-5 is believed to function as an elongation factor. Another accessory protein is VLF-1, which is a promoter specificity factor. Yet another accessory protein is a methyltransferase. It is known that a methyltransferase methylates the cap of mRNA. A methylated capped mRNA is more stable than a non-methylated capped mRNA. However, methylation of tie cap is not essential. It is contemplated that baculovirus contains a viral mnethyltransferase that methylates capped mRNA. Thus, it is envisioned that this viral methyltransferase may be used as an accessory protein to produce a more stable mRNA. Other accessory proteins may include, but are not limited to IE1, IE2, LEF-1, LEF-2, LEF-3, LEF-5, LEF-6, LEF-7, LEF-1-, P35, pp31/39K and VLF-1.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

Another aspect of the present invention is the baculovirus termination site. This consists of 7 consecutive T residues in the non-template strand or similar sequence that is T-rich in the non-template strand resulting in transcription termination.

The following sequences are within the scope of the invention and are referenced with the corresponding GenBank (http://www.ncbi.nlm.nih.gov/Genbank/GenbankSearch.html) Accession Numbers: LEF1 (NP_054043; SEQ ID NO:1); LEF2 (NP_054035; SEQ ID NO:2); LEF3 (NP_054097; SEQ ID NO:3); LEF4 (NP_054120; SEQ ID NO:4); LEF5 (NP_054129; SEQ ID NO:5); LEF6 (NP_054057; SEQ ID NO:6); LEF7(NP_054155; SEQ ID NO:7); LEF8 (NP_054079; SEQ ID NO:8); LEF9 (NP_054092; SEQ ID NO:9); LEF10 (NP_054083; SEQ ID NO:10); LEF11 (NP_054066; SEQ ID NO:11); LEF12 (NP_054070; SEQ ID NO:12);IE1 (RGNVE2; SEQ ]D NO:13); IE2 (SEQ ID NO:14); helicase (NP_054125 (SEQ ID NO:15); H72861 (SEQ ID NO:16); HJNVAV (SEQ ID NO:17); AAA66725 (SEQ ID NO:18); AAA67907 (SEQ ID NO:19); P24307 (SEQ ID NO:20)); DNA polymerase (NP_054095 (SEQ ID NO:21); B72858 (SEQ ID NO:22); DJNVCP (SEQ ID NO:23); P18131 (SEQ ID NO:24); AAA66695 (SEQ ID NO:25); BAA00461 (SEQ ID NO:26); BAA00460 (SEQ ID NO:27); AAA46692 (SEQ ID NO:28)); PP31 NP_054065 (SEQ ID NO:29); P11042 (SEQ ID NO:30); AAA66666 (SEQ ID NO:31)); p35 (P08160; SEQ ID NO:32); vlfl (NP_054107; SEQ ID NO:33); and p47 (NP_054069 (SEQ ID NO:34); H72854 (SEQ ID NO:35)).

Also within the scope of the invention is the genome sequence of *Autographa californica* nuclear polyhedrosis virus (AcNPV) (NC_001623; SEQ ID NO:36 or L22858; SEQ ID NO:37).

2) Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

IV. Proteins and Peptides

The present invention relates to the entire protein complex, or subunits or fragments of the baculovirus RNA polymerase (Gene Bank accession numbers are contained herein in other areas of the present disclosure that correspond to the nucleic acid and protein sequences of the baculovirus RNA polymerase and related proteins) that retains the function of an RNA polymerase, which is initiation of transcription. Yet further, other proteins that aid in transcription, e.g., accessory proteins, are also contemplated in the present invention. Such accessory protein include, but are not limited to lef5, vlfl or methyltransferase. Fragments, including the N-terminus of the molecule may be generated by genetic engineering of translation stop sites within the coding region (discussed below). Alternatively, treatment of the polypeptides with proteolytic enzymes, known as proteases, can produce a variety of N-terminal, C-terminal and internal fragments. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

1. Variants of Protein

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying nucleic acid coding sequence, and nevertheless obtain a protein with like properties. It is thus contemplated by the inventors that various changes may be made in the nucleic acid sequences of genes without appreciable loss of their biological utility or activity as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics Byte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0 ±1); serine (+0.3); asparagine (+0.2); glutamine (+0.2); glycine (0); threonine (−0.4); proline (−0.5+1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

As outlined above, amino acid substitutions are generally based on the relative similarity of the amino acid side-chain substituent, for example, their hydrophobicity, hydrophilicity, charge, size, and the like. Exemplary substitutions that take the foregoing characteristics into consideration are well known to those of skill in the art and include: arginine and lysine; glutamate and aspartate; serine and threonine; glutamine and asparagine; and valine, leucine and isoleucine.

2. Domain Switching

Domain switching involves the generation of chimeric molecules using different but, in this case, related polypeptides. By comparing various RNA polymerase, one can make predictions as to the functionally significant regions of these molecules. It is possible, then, to switch related domains of these molecules in an effort to determine the criticality of these regions to RNA polymerase function. These molecules may have additional value in that these "chimeras" can be distinguished from natural molecules, while possibly providing the same function.

3. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction facilitates removal of the extraneous polypeptide after purification. Other useful fusions include linking of functional domains, such as active sites from enzymes, glycosylation domains, cellular targeting signals or transmembrane regions.

4. Purification of Proteins

It may be desirable to purify the RNA polymerase complex, subunit proteins or variants thereof. Also, it is envisioned that accessory proteins may be purified. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et. al., 1977). It can therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix, should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elate the substance without destroying the sample or the ligand. One of the most common forms of affinity chromatography is immunoaffinity chromatography. The generation of antibodies that would be suitable for use in accord with the present invention is discussed below.

5. Synthetic Peptides

The present invention also includes RNA polymerase-related peptides for use in various embodiments of the present invention. The peptides of the invention can also be synthesized in solution or on a solid support in accordance with conventional techniques. Various automatic synthesizers are commercially available and can be used in accordance with known protocols. See, for example, Stewart and Young, (1984); Tam et. al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

IV. Gene Therapy

Figure 2:
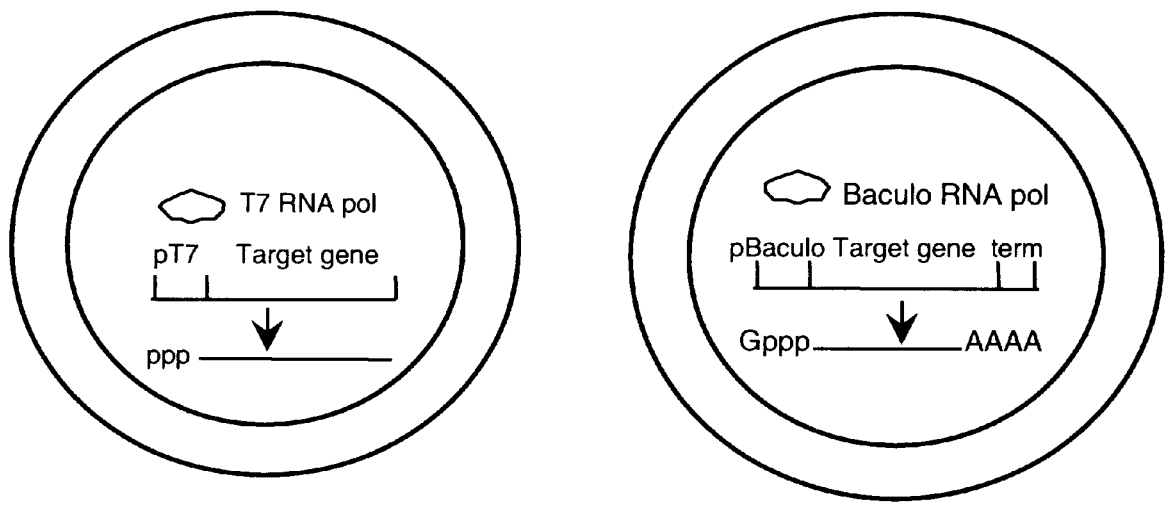
FIG. 2 Diagram of liposome-mediated non-viral vectors for gene therapy. The T7 vectors are modeled after those previously described (Brisson et al., 1997; Mizugichi et al., 1997). The baculovirus vector offers improved translational efficiency and stability due to posttranscriptional processing at the 5' and 3' ends. Expression from both types of vectors can be sustained for longer periods of time by including another gene cassette that drives expression of the polymerase from the viral promoter.

Another potential application of the baculovirus RNA polymerase system is as a non-viral vector. This would be an alternative to, and probably an improvement upon, vectors using T7 RNA polymerase (Brisson et al., 1997; Mizuguchi et al., 1997). A T7 non-viral vector uses T7 RNA polymerase packaged in a liposome with a plasmid or PCR fragment encoding a target gene linked to the T7 RNA polymerase (FIG. 2). Continuous express-ion for several days can be obtained with vectors containing the gene for T7 RNA polymerase also under control of the T7 promoter. We expect that levels of expression could be significantly improved by substituting the baculovirus RNA polymerase for T7 RNA polymerase because the transcripts would be correctly processed. Therefore, they would be more stable and more efficiently translated in transfected cells.

One skilled in the art may recognize that the mode of DNA delivery of this invention could potentially be used to deliver DNA to specific cells for gene therapy. For gene therapy, a skilled artisan will be cognizant that the vector or vectors to be utilized must contain the gene of interest operatively limited to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying, large volumes of a liquid (pressure); and (2) methods wherein said vector is complexed to another entity, such as a liposome, aggregated protein or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridization, or transcription assays to detect the nucleic acid in host cells, or using immunoblot analysis, antibody mediated detection, mRNA or protein half life studies, or particularized assays to detect protein or polypeptide encoded by the transferred nucleic acid, or impacted in level or function due to such transfer).

These methods described herein are by no means all inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g. based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene, which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidine kinase (Tdk::Tmk) and AZT; and deoxycytidine kinase and cytosine arabinoside.

Those of skill in the art are well aware of how to apply gene delivery to in vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below. Various routes are contemplated, but local provision to the heart and systemic provision (intraarterial or intravenous) are preferred.

V. Lipid Formulations and/or Nanocapsules

In certain embodiments, the use of lipid formulations and/or nanocapsules is contemplated for the introduction of gene therapy vectors, including both wild-type and/or antisense vectors, into host cells.

Nanocapsules can generally entrap compounds in a stable and/or reproducible way. To avoid side effects due to intracellular polymeric overloading, such ultrafine particles (sized around 0.1 μm) should be designed using polymers able to be degraded in vivo. Biodegradable polyalkylcyanoacrylate nanoparticles that meet these requirements are contemplated for use in the present invention, and/or such particles may be easily made.

In a preferred embodiment of the invention, the gene therapy vector may be associated with a lipid. The gene therapy vector associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/gene therapy vector associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY—YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hrs, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-flee water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

VI. Method of Nucleic Acid Delivery

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1) Injection

In certain embodiments, a nucleic acid may be delivered to an organelle, a cell, a tissue or all organism via one or more injections (i.e., a needle injection), such as, for example, subcutaneously, intradermally, intramuscularly, intervenously, intraperitoneally, etc. Further embodiments of the present invention include the introduction of a nucleic acid by direct microinjection. Direct microinjection has been used to introduce nucleic acid constructs into Xenopus oocytes (Harland and Weintraub, 1985).

2) Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al, 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

3) Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4) DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

5) Sonication Loading

Additional embodiments of the present invention include the introduction of a nucleic acid by direct sonic loading. LTK-fibroblasts have been transfected with the thymidine kinase gene by sonication loading (Fechheimer et al., 1987).

6) Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

7) Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

8) Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

VII. Stable Cells Lines

The baculovirus expression vector system (BEVS) is widely used for expression of foreign genes in a eukaryotic system. One limitation of BEVS is that expression requires infection of insect cells with virus. Because infection kills the cells, expression is transient and, therefore, the usefulness of the system is limited. Transient expression is acceptable for research applications, but it is unfavorable for commercial applications. One way to overcome this limitation would be to develop stable cell lines that express the subunits of baculovirus RNA polymerase under an inducible promoter, such as the tetracyline promoter so that the genes were not expressed in the absence of tetracycline. These cell lines would be marketed as an expression line along with a vector for cloning target genes under the polyhedrin promoter. This vector would contain a selectable marker suitable for use in insect cells, such as neomycin phosphotransferase or the zeocin resistance gene. Users of this system would clone their desired target gene into the multiple cloning site, transform the cells and select for stable transformants. The cells could be grown and amplifed. Then expression of the target gene could be induced by adding tetracycline to stimulate transcription of RNA polymerase, which would then transcribe the target gene.

In certain cases in which the target gene is non-toxic to the cells, it may also be possible to amplify the cells under conditions where the target gene is continually expressed.

In this way, it should be possible to harness the high expression capability of the baculovirus; RNA polymerase/polyhedrin promoter, which has made the baculovirus expression system popular, without killing cells in the process of viral infection.

VIII. EXAMPLES

The following examples are included to demonstrate preferred embodiments of the invention. Further, the following mauscripts are hereby incorporated by reference in their entirety, Jin, et al., *J. Virology* 74:8930–8937, 2000, Guarino, et al., *J. Virology* 72:7985–7991, 1998, Guarino, et al., *J. Virology* 72:10003–10010, 1998 and Jin, et al., *J. Virology* 72:10011–10019, 1998. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Purification of Baculovirus RNA Polymerase Complex

Figure 3:
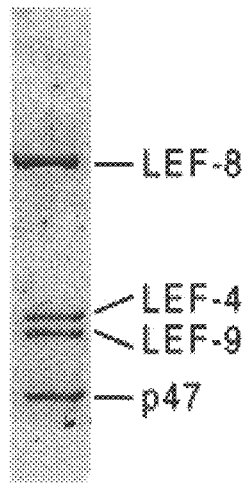
FIGS. 3 SDS-PAGE analysis of baculovirus RNA pol.

As previously mentioned, baculoviruses use host RNA polymerase II for transcription of early genes, and encodes its own RNA polymerase that transcribes the structural genes. The viral RNA polymerase was purified and characterized. Baculovirus RNA polymerase is a four subunit complex with a combined molecular weight of 258,000 (FIG. 3).

Methods

Preparation of nuclear extracts. *Spodopter frugiperda* (Sf9) cells were cultured and infected with the E2 strain of AcNPV as previously described (Summers and Smith, 1987). Nuclear extracts were prepared from AcNPV-infected Sf9 cells at 36 h postinfection, with two modifications to the previous protocol (Xu et al., 1995). After Dounce homogenization, the nuclei were washed twice by low-speed centrifugation in hypotonic buffer containing 6% sucrose and then pelleted through a 30% sucrose cushion by centrifugation at 3,000×g for 10 min. After centrifugation of the nuclear extracts at 100,000×g, the supernatants were frozen in liquid nitrogen and stored at −80° C.

Purification of the RNA polymerase complex. All procedures were carried out at 4° C. Nuclear extracts were prepared from two to five 1-liter cultures and frozen until a total of 25 liters of infected cells had been collected. Pooled nuclear extracts were treated with 0.1% polymin P to precipitate nucleic acids. Soluble proteins were then precipitated with 50% ammonium sulfate. The ammonium sulfate precipitate was collected by centrifugation, resuspended in 25 ml of buffer A (50 mM Tris [pH 7.9]. 0.1 mM EDTA, 1 mM dithiothreitol) containing 0.5M $(NH_4)_2SO_4$, and loaded onto a 12-ml phenyl-Sepharose column (Pharmacia) at a rate of 2 ml/min. The column was washed with 50 ml of buffer A-0.5M $(NH_4)_2SO_4$, and bound protein was eluted with buffer A-300 mM KCl-0.5% 3-[(3-cholamidopropyl)-dimethylammonio]-1-propanesulfonate (CHAPS; Pierce). Fractions (1.8 ml) were collected and assayed for transcription activity. Active fractions were pooled, dialyzed against buffer A-300 mM KCl-0.1% CHAPS, and applied at 1 ml/min to a 5-ml heparin (Bio-Rad) column connected to a Pharmacia FPLC system previously equilibrated with buffer A-300 mM KCl-0.1% CHAPS. The column was washed with loading buffer and eluted with a 20-ml linear gradient from 300 to 500 mM KCl. Peak fractions were pooled, the KCl concentration was adjusted to 250 mM, and the protein was applied to a Mono Q HR 5/5 column (Pharmacia) previously equilibrated with buffer A-200 mM KCl-0.1% CHAPS. The column was washed with 10 ml of loading buffer and then eluted with a 20-ml linear KCl gradient from 100 to 500 mM. Fractions that contained transcription activity were concentrated to 200 µl and filtered through a Superose 6 column in buffer A-2 M KCl-0.1% CHAPS. Fractions (0.5 ml) were individually dialyzed against buffer A-250 mM KCl-0.1% CHAPS, assayed for transcription activity, frozen in liquid nitrogen, and stored at −80° C. Protein concentrations of the crude extract and partially purified fractions were determined by the method of Bradford (1976). The concentration of the purified complex was determined by UV absorbance using a molar extinction coefficient of 259,350, predicted by the amino acid sequences of the four subunits (Ayres et al., 1994).

Results

RNA polymerase activity was tested after each purification step by using a baculovirus promoter-specific assay as previously described (Xu et al., 1995). The transcription complex eluted in a single peak from each column, indicating that all factors required for enzymatic activity and promoter recognition were tightly associated in a single complex. In the crude extract and in the phenyl-Sepharose peak, transcription activity was not linear with respect to amount of protein added, probably because of contaminating nucleases or other proteins that interfere with the assay. The specific activity of the purified RNA polymerase was approximately 134,000 U/mg of protein.

The distribution of transcription activity on Superose 6 coincided with a peak of protein as measured by absorbance at 280 nm (FIG. 4A). RNA polymerase fractionated with an apparent molecular weight of 560,000. When fractions across the peak were assayed by SDS-PAGE, four polypeptides with apparent molecular weights of 98,000, 55,000, 53,000, and 46,000 were found to increase and decrease concomitant with the peak of enzymatic activity as well as with the peak of protein (FIG. 4B). Additional bands were detected in the molecular weight range of 55,000 to 65,000. These probably represent contaminating keratins since they were observed in most lanes, including lanes with no protein loaded.

The stoichiometry of the four proteins was determined to be equimolar on the basis of Coomassie brilliant blue staining relative to protein markers of known concentration (FIG. 4C), which suggests that an active transcription complex contains two molecules of each subunit. There was no evidence for additional protein bands in the Coomassie blue-stained gel, which suggests that contaminating proteins, if present, were submolar. Analysis of polymerase subunits on a 13% polyacrylamide gel, followed by staining with either silver or Coomassie blue, failed to reveal the presence of smaller subunits.

Example 2

Template Specificity of the Baculovirus RNA Polymerase

Methods

In vitro transcription assays. In vitro transcription assays for AcNPV late and very late promoters were performed by using slight modifications of conditions previously described (Xu, 1995). Transcription reaction mixtures contained 50 µg of nuclear extract of 10 µl of column fractions and the following components in a volume of 50 µl: 25 mM Tris (pH 7.9), 100 mM KCl, 2 mM MgCl2, 1 mM dithiothreitol, 1.0 mM each ATP and UTP, 20 µM GTP, 5 µCi of [α-$^{32}$P]GTP(800 Ci/mmol), 5 U of RNasin, 0.2 U of inorganic pyrophosphatase, and 1.0 µg each of Polh/CFS and 39 kL/CFS. Addition of α-amantin was not necessary and was not routinely used. As shown by Xu et al. (1995), the host RNA polymerases cannot transcribe the baculovirus templates used in these assays. Components were added to the enzyme at the same time, reaction mixtures were incubated for 12 min at 30° C., and then the reaction was stopped by the addition of 150 µl of stop buffer (50 mM Tris [pH 7.5], 1% sodium dodecyl sulfate [SDS], 5 mM EDTA, 25 µg of tRNA per ml). RNA was extracted once with phenol-choloroform (1:1), precipitated with ethanol, resuspended in 90% formamide, and resolved on a 6% polyacrylamide-8M urea gel. For quantitation of RNA polymerase activity, transcription reaction mixtures were spotted onto glass fiber filters and precipitated with tricholoacetic acid. By definition, 1 U of transcription activity incorporates 1 pmol of GMP into RNA in 10 min at 30 ° C. The conditions for in vitro transcription from early viral promoters have been previously described (Yoo and Guarino, 1994).

Results

Two plasmids containing either the late 39 k promoter or the very late polh promoter linked to a cytidine-free synthetic template (Xu et al., 1995) were used in the in vitro transcription assay. Purified RNA polymerase was incubated with template, ATP, UTP, and [α-$^{32}$P]GTP for 15 min at 30° C. RNA products were purified by phenol extraction and separated on denaturing polyacrylamide gels. As shown in FIG. 5, the purified polymerase supported accurate and specific initiation from both the late 39 k and the very late polyhedrin promoter. Templates lacking a promoter or linked to an early promoter were not transcribed. This indicates that promoter recognition is an integral property of RNApol. Primer extension assays confirmed that transcription initiated within the ATAAG motif that is the primary determinant of late transcription in vivo.

The finding of a viral-encoded RNA polymerase answered the essential question of how baculoviruses were able to produce such high levels of virion proteins during the very late stage of viral infection—baculoviruses encode a very active RNA polymerase that specifically recognizes viral promoters and takes over the cellular synthetic machinery. This strategy is the same as that used by the bacteriophages T3, T7, and SP6. But baculoviruses, which function in a eukaryotic cell, have additional requirements for their transcription machinery. The baculovirus RNAs must be capped at the 5' ends with methyl-7-guanosine and polyadenylated at the 3' ends; these modifications confer message stability as well as improved translation. Both of these modifications are mediated by enzymes that recognize their substrates through interactions with RNA polymerase II. This model suggests that baculoviruses should encode their own capping and polyadenylation enzymes.

Example 3

Identification of Protein Subunits

Methods

Preparation of LEF-8 antiserum. The AcNPV lef-8 gene was amplified by PCR using an upstream primer (5'-AATCGCTT<u>CCATATG</u>ACGGACGTGGTTCAAG-3') which produced an NdeI site (underlined) it the translation initiation codon of the lef-8 coding sequence and a second primer (5'-GTTTGCAATCGTCGAAGC-3') that hybridized downstream of the lef-8 stop codon. The amplified fragment was first cloned into the pCRII vector (Invitrogen) and then subcloed into the T7 expression vector pET15b (Novagent). The resulting plasmid, pET-lef8, was used to express LEF-8 in *Escherichia coli* BL21(DE3)LysE cells. Overexpressed LEF-8 protein was purified by SDS-PAGE and used to generate polyclonal antiserum in mice by using a standard immunization protocol (Harlow and Lane, 1988).

Samples for immunoblot analysis were boiled for 3 min and electrophoresed on an 8% acrylamide gel. The proteins were electrophoretically transferred to nitrocellulose sheets by using a semidry apparatus. The sheets were reacted with LEF-8 antiserum, and immune complexes were detected by using alkaline phosphatase-conjugated anti-mouse immunoglobulin G.

Primer extension mapping of lef-9. Total RNA was isolated from AcNPV-infected cells by the guanidine isothiocyanate-cesium chloride method (Chirgwin et al., 1979). A lef-9 specific primer (GTGAGGGTCTAATATGAGG) was radiolabeled at the 5' end and hybridized with 20 µg of RNA. Annealed primers were extended with avian myeloblastosis virus reverse transcriptase (Sambrook et al., 1989). Reaction products were analyzed on 6% polyacrylamide-8 M urea gels. Sequencing ladders were generated by using pPstI-H DNA (Gong and Guarino, 1994) and the same oligonucleotide primer.

Results

Figure 4:
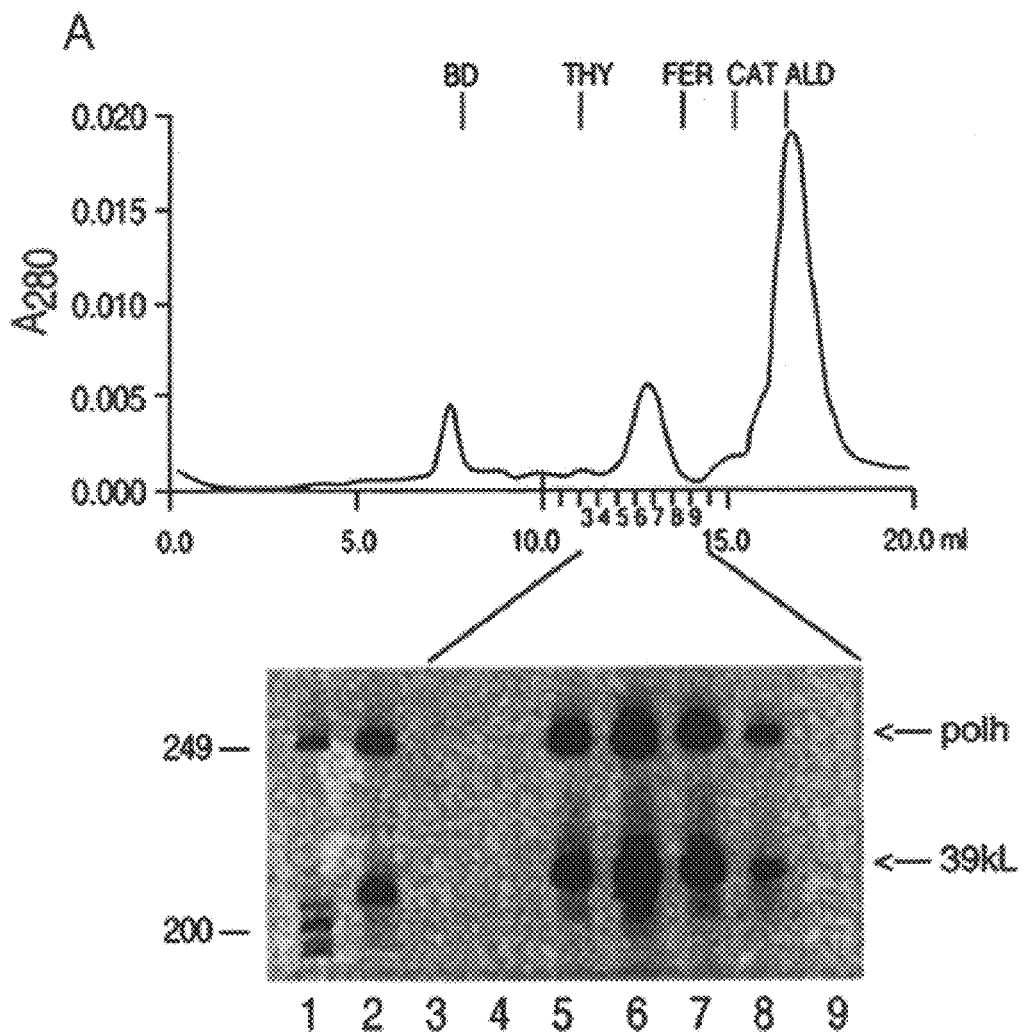
FIG. 4(A) Gel filtration chromatography of RNA polymerase. RNA polymerase was filtered through Superose 6. Fractions (0.5 ml) were collected from 10 to 15 ml and assayed for transcription activity. The indicated fractions were assayed for in vitro transcription activity. A transcription assay of the pooled Mono Q peak is shown in lane 2. Lane 1 contains φX174-HindIII molecular markers;, and the sizes (in kilobases) of relevant fragments are shown on the left. The transcripts corresponding to Polh/CFS and 39kL/
Figure 4:
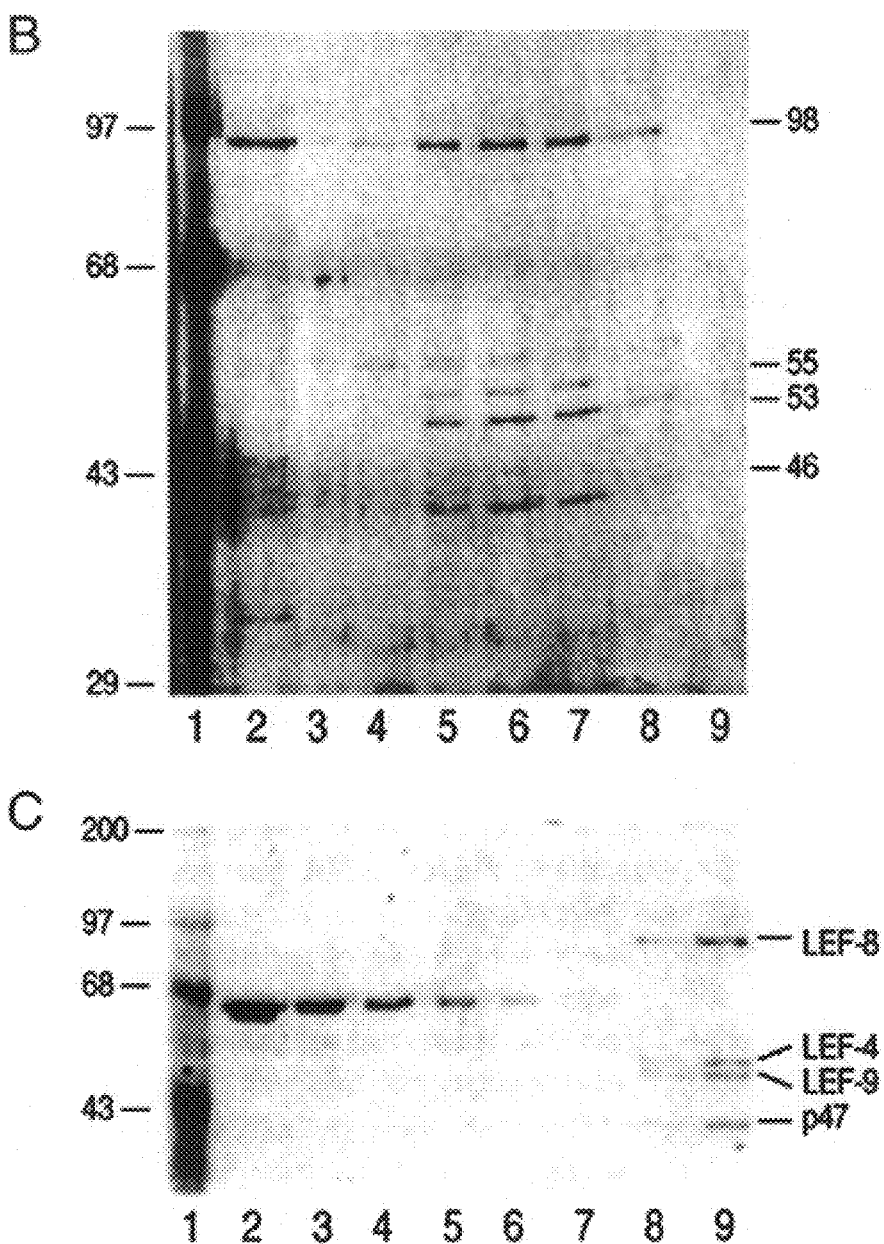

The two smallest RNA polymerase subunits were identified by N-terminal amino acid sequence. Purified RNA polymerase subunits were separated by electrophoresis on SDS-8% polyacrylamide gels, transferred to polyvinylidene difluoride membranes, and submitted for automated Edman degradation. The sequence of the smallest subunit was Met-Phe-Val-Thr-Arg-Leu. The only perfect match for this sequence in the combined SwissProt/GenBank protein databases is the AcNPV protein known as p47. The gene encoding p47 was originally identified as the site of the temperature-sensitive mutant ts317 (Carstens et al., 1994). This mutant was defective in the release of infectious virus and expression of polyhedrin at the nonpermissive temperature, although viral DNA synthesis appeared to be normal. This phenotype suggested that the mutation disrupted a function required for transcription of late and very late genes. P47 was also identified by Todd et al. (1995) as one of the 18 genes required for transient expression of reporter genes under the control of baculovirus late and very late promoters. The p47 gene is predicted to encode a protein of 47.5 kDa, which is in good agreement with an apparent molecular mass of 46 kDA calculated from SDS-gels (FIG. 4). Thus, identification of p47 as one of the RNA polymerase subunits is consistent with the known biology of he protein.

The N-terminal sequence of the next-smallest subunit was determined to be Met-Phe-Ser-Phe-Leu-Asp. The only perfect match to this sequence in the protein databases was the AcNPV LEF-9 protein. The lef-9 gene was originally mapped by Lu and Miller (1994) as part of a screen for viral genes required for transient expression of baculovirus late and very late genes. The amino acid sequence that the inventors determined corresponds to residues 27 to 32 of the LEF-9 ORF as originally published (Lu and Miller, 1994). However, in that report, transcriptional mapping of the lef-9 gene was not performed and the ORF was assumed to start at the furthest upstream methionine codon. This discrepancy suggests either that the protein the inventors sequenced was subject to posttranslational processing or the incorrect start site was identified by Lu and Miller (1994).

To address the question of which methionite codon was used for initiation of translation of the lef-9 ORF, the inventors performed primer extension assays. RNA purified from AcNPV-infected cells was hybridized with an oligonucleotide complementary to a sequence within the N terminus of ORF-9. The inventors found that the 5' ends of lef-9 transcripts mapped to heterogeneous sites between the upstream methioline codon and the residue identified in the sequence analysis (FIG. 7). Transcription initiating from two start sites proximal to the lef-9 ORF was detected primarily at the 6-h time point, although low levels of transcripts initiated at a CACT motif, which occurs 26 nucleotides downstream of a TATA sequence. This arrangement of promoter motifs is similar to that found in many of the baculovirus early promoters, in which initiation begins at a CAGT motif (Blissard and Rohrmann, 1990). A single distal transcription start site was mapped to a point 12 nucleotides further upstream. Sequences surrounding this start site do not correspond to consensus early promoters. Transcription from this point was detected in a 6 h postinfection, and transcripts persisted through 36 h postinfection.

The primer extension data strongly argue that he LEF-9 ORF initiates with the sequence Met-Phe-Ser-Phe-Leu-Asp and not at the upstream site previously identified (Lu and Miller, 1994). Recalculation of the molecular weight for LEF-9 according to the protein sequence data predicts a polypeptide of 56 kDa, which is closer to the apparent molecular weight of this subunit than the previously published value of 59 kDa.

N-terminal sequence analysis of the 55-kDa polypeptide failed to yield useful sequence information. Therefore, protein fingerprinting was used to identify this subumit. An SDS-polyacrylamide gel slice containing the 55-kDa subunit was digested with trypsin, and then the eluted peptides were analyzed by mass spectroscopy to determine their molecular masses. The masses of all tryptic peptides were entered into the MOWSE database searching program (Pappin et al., 1993), which matches peptide fingerprints of an unknown protein with the predicted fingerprints of all ORFs in the OWL database. The most significant match returned by the database search was for the AcNPV LEF-4 protein. Eleven of the 19 tryptic peptides entered matched those predicted for LEF-4, which confirms the identity of this protein. LEF-4 was first mapped by Pasarelli and Miller (1993) as a factor required for expression of viral late genes, and it was subsequently identified as the site of a temperature-sensitive mutation producing a phenotype similar to the p47 mutation described above (Carstens et al., 1994). The predicted molecular size of LEF-4 is 54 kDa, consistent with an apparent molecular size of 55 kDa calculated from FIG. 4B.

Attempts to sequence the largest subunit were not successful. However, the inventors were able to predict and confirm the identity of the protein by immunochemical analysis. AcNPV encodes relatively few proteins in the molecular weight range observed for the largest subunit. One of these, LEF-8, contains a conserved sequence motif that is common to prokaryotic and eukaryotic RNA polymerases (Passarelli and Miller, 1993). In addition, LEF-8 is required for viral late and very late gene expression in a transient assay, consistent with its proposed role as a component of the virus-specific RNA polymerase. Therefore, the inventors raised antiserum against LEF-8 expressed in bacteria and immunoblotted fractions across the Superose 6 peak. As shown in FIG. 6, the large subunit of purified RNA polymerase was recognized by the LEF-8 antiserum. The intensity of the immunoreactive bands closely correlated with the peak of transcription activity. The inventors conclude, therefore, that the large subunit is encoded by lef-8.

Example 4

Cloning and Overexpression of RNA Polymerase
Methods

Construction of vBAC-RNApol. The transfer vector pBAC4x-1 (Novagen) contains two copies of the polh promoter and two copies of the p10 promoter with unique restriction sites downstream of each promoter. The four RNA polymerase subunit genes were cloned into this plasmid for overexpression of AcNPV RNA polymerase in infected cells according to standard cloning protocols (Sambrook et al., 1989). A BamHI site (GTGCGCAGTAATGGATCCACGATGACGGAC; BamHI site underlined) was inserted upstream of the lef-8 open reading frame (ORF) in the genomic clone pEcoRI-M by site-directed mutagenesis (Deng and Nickoloff, 1992). The resulting 2-kb BamHI-EcoRI fragment containing lef-8 was cloned into pBAC4x-1 (Novagen) under polyhedrin control. The AcNPV genomic clone pHindIII-C was digested with NarI and XhoI and incubated with Klenow enzyme and deoxynucleoside triphosphates to fill in 540 overhangs. A 1.6-kb fragment containing the complete lef-4-ORF was purified by agarose gel electrophoresis and cloned into the SmaI site of pBAC4x-lef8. Insertion of the fragment in the correct orientation was determined by restriction digestions. Site-directed mutagenesis was used to construct a BamI site (underlined) upstream of the lef-9 ORF (ACGCGTTCGTGTACGGATCCAAACATGTTT). The resulting plasmid was digested with BamHI and BglII, and the ends were repaired with Klenow enzyme. A 1.4-kb fragment containing lef-9 was cloned into the StuI site of pBAC4x-lef8/lef4 under the control of the polh promoter. The orientation of the insert was screened by restriction digest analysis. The genomic clone pPstI-F was digested with EcoRI and PstI sites of pVL1391. The p47 ORF was excised from this plasmid by digestion BglII, followed by repair with Klenow enzyme and digestion with BamHI. The p47 fragment was then ligated with pBAC-RNApol, was cotransfected with linearized BakPAK6 (Clontech) DNA into Sf9 cells. Recombinant viruses were amplified and used to prepare nuclear extracts by the same protocol as described above except that cells were harvested at 60 h postinfection and the polymin P concentration was increased to 0.2%.

Results

To confirm that the RNA polymerase subunits had been correctly identified, the inventors cloned the genes encoding p47, LEF-9, LEF-4, and LEF-8 into the baculovirus transfer vector pBAC4x-1. This plasmid contains two copies of the polh promoter and two copies of the p10 promoter and allows for overexpression of four proteins in a baculovirus expression system. Sf9 cells were infected with the recombinant virus pBAC-RNApol, and nuclear extracts were prepared from cells harvested at 60 h postinfection. In a wild-type virus infection, in vivo synthesis of viral RNAs had ceased by 60 h postinfection, and RNA polymerase activity was undetectable in extracts prepared from wild-type virus-infected cell, harvested at this time. However, in cells infected with Pbac-rnaPOL, transcription activity was high in extracts prepared at 60 h postinfection. Overall yields of RNA polymerase per liter of infected cells were 10-fold higher than yields with wild-type virus harvested at 36 h postinfection. From 5 liters of cells infected with Pbac-rnaPOL the inventors were able to purify 70 µg of RNA polymerase, while the yield from wild-type virus-infected cells was only 36 µg from 25 liters of infected cells.

The data suggest that baculoviruses are more similar to T7 and related bacteriophages than to the host or other eukaryotic viruses. The replication strategies employed by the two viruses are strikingly similar, although one infects insect cells and the other infects bacteria. In both cases, the early viral promoters resemble their host promoters and are transcribed by the corresponding host RNA polymerases. However, the structures of the viral late gene promoters are dramatically different from those of their early promoters and they do not contain motifs recognized by the host polymerases. In fact, the structures of the baculovirus and T7 late promoters are more similar to each other than either is to the structures of the promoters of their hosts. Both promoters consist of a short conserved sequence that serves as both a promoter and an initiator element (Rankin et al., 1988; Rohrmann, 1986). Therefore, it is not surprising to find that baculoviruses, like T7 bacteriophage (Chamberlin and Ring, 1973), use a virus-encoded RNA polymerase to transcribe viral late genes. The T7 RNA polymerase is a single polypeptide which contains both promoter recognition and enzymatic activities (Bailey et al, 1983). Although simple in structure, the viral polymerases transcribe their cognate genes efficiently and with high specificity.

The baculovirus-encoded RNA polymerase, which was purified and characterized (Guarino et al., 1998), is composed of four subunits (FIG. 3). All four of these proteins (p47, LEF-4, LEF-8, and LEF-9) are essential for viral replication in tissue culture cells and for transient expression of viral late genes (Todd et al., 1995). LEF-8 is the largest subunit at 102,000 mol wt and it contains a motif that is conserved amongst the β subunits of bacterial and eukaryotic RNA polymerases (Passarelli et al., 1994). The LEF-9 subunit, which is 55 kDa, also contains one short region of homology to the β' subunits of RNA polymerases. This suggests that these subunits constitute the catalytic domain of baculovirus RNA polymerase. The LEF-4 subunit is an mRNA capping enzyme, and the function of p47 is unknown.

Example 5

Production of Capped Messages with Baculovirus RNA Polymerase

Although protein database searches failed to reveal homologies between capping enzymes and the RNA polymerase subunits, the inventors noted the presence of a KxDG motif in the LEF-4 subunit. This sequence element is a conserved motif found guanylyltransferases (Cong and Shuman, 1993). This is one of the three enzymes required for formation of a methyl-7-guanosine cap. Guanylyltransferases bind GMP to the lysine residue within this conserved motif (Niles and Christen 1993; Wang et al., 1997). To test whether LEF-4 was a guanylyltransferase, purified RNA polymerase and purified LEF-4 subunit were assayed for guanylyltransferase activity (Guarino et al., 1998b). Incubation of enzyme with radiolabeled GTP and divalent cation resulted in the formation of a LEF-4-GMP complex, confirming that LEF-4 was a capping enzyme.

Methods

Construction of vLEF-4. The *Autographa californica* nuclear polyhedrosis virus (AcNPV) genomic clone pHindIII-C was digested with NarI and XhoI and incuvated with Klenow enzyme and deoxynucleoside triphosphates to fill in 5' overhangs. A 1.6-kb fragment containing the complete left-4 open reading frame was purified by agarose gel electrophoresis and cloned into the SmaI site of pVL1391. Correct orientation of the insert was determined by restriction digest. The resulting plasmid pVL1391-LEF4 was cotransfered with Bsu36I-digested RP6-SC DNA into *Spodoptera frugiperda* cells. Recombinant viruses were plaque purified and amplified by standard protocols (Summers and Smith, 1987). One plaque isolate with the correct insert was named vLEF-4.

Purification of LEF-4 from baculovirus-infected cells. *S. frugiperda* cells grown in 1-liter spinner cultures were infected with vLEF-4 and harvested at 60 h postinfection. Cells were washed in phosphate-buffered saline, and resuspended in four times the packed cell volume of hypotonic buffer (10 mM Tris [pH 7.9], 10 mM KCl, 3 mM dithiothreitol [DTT], 0.1 mM EDTA, 0.1 mM EGTA, 0.75 mM spermidine, 0.15 mM spermine, 3 µg of leupeptin per ml). The cells were allowed to swell on ice for 20 min and broken by homogenization in a glass ounce homogenizer (B pestle). Cells were checked by phase microscopy for complete breakage, and then a 1/10 volume of restoration buffer (50 mM Tris [pH 7.9], 0.75 mM spermidine, 0.15 mM spermine, 10 mM KCl, 0.2 mM EDTA, 3 mM DTT, 67.5% sucrose) was added. The homogenate was layered over a 10-ml sucrose cushion (30% sucrose in hypotonic buffer) and centrifuged for 10 min at 3,000 rpm. The supernatant (cytosolic fraction) was saved, and the pelleted nuclei were resuspended in four times the packed-cell volume of nuclear extraction buffer (50 mM Tris [7.9 pH], 0.42M KCl, 6 mM DTT, 0.1 mM EDTA, 10% sucrose, 5 mM $MgCl_2$, 20% glycerol, 0.5 mM phenylmethylsulfonyl fluoride). The nuclei were then lysed by gentle rocking at 4° C. for 30 min, and the lysate was centrifuged at 40,000 rpm in a Beckman Ti 50.2 rotor for 90 min at 4° C. to remove the DNA. The protein components of cytosolic and nuclear fractions prepared from vLEF-4 and RP6-SC-infected cells were compared by sodium dodecyl sulfate (SDS)-polyacrulamide gel electrophoresis (PAGE) analysis. By this method, overexpressed LEF-4 was localized to the cytosolic fraction.

The LEF-4 cytosolic extract was precipitated with 40% saturated $NH_4SO_4$, resuspended in 8 ml of buffer A (50 mM Tris [pH 7.9], 0.1 mM EDTA, 1 mM DTT) containing 50 mM KCl, and dialyzed against 800 ml of the same buffer. Then the sample was applied to a ml/min to a 5-ml heparin (Bio-Rad) column connected to a Pharmacia FPLC system previously equilibrated with buffer A-50 mM KCl. The column was washed with 10 ml of loading buffer and eluted with a 20-ml linear gradient from 50 to 500 mM KCl. Samples were analyzed by SDS-PAGE. Peak fractions containing LEF-4 were pooled, dialyzed against buffer A-50 mM KCl, ad the protein was applied to a Mono Q HR 5/5 column (Pharmacia) previously equilibrated with buffer A-50 mM KCl. The column was washed with 5 ml of loading buffer and then eluted with a 20-ml linear KCl gradient from 50 to 500 mM. Fractions that contained LEF-4 were concentrated to 200 μl and filtered through a Superdex 200 column in buffer A-100 mM KCl. Fractions (0.5 ml) were collected, individually frozen in liquid nitrogen, and stored at −8°° C. The protein concentration of LEF-4 was determined by UV absorbance using a molar extinction coefficient of 57,800.

Assay of enzyme-GMP complex formation. Standard reaction mixtures contained 1 pmol of purified RNA polymerase of LEF-4, 1 mM $MnCl_2$, 5 mM DTT, and 5 μM [α-$^{32}$P]GTP in 25 μl. Samples were incubated for 15 mm at 30° C. and then stopped by the addition of 1% SDS. Samples were boiled and electrophoresed through an SDS-8% polyacrylamide gel. Gels were fixed, dried, and exposed to film.

Results

Guanylyltransferases catalyze the transfer of GMP from GTP to a diphosphate-terminated RNA. This is a two-step reaction involving the formation of a covalent enzyme-guanylate intermediate in which GMP is linked by a phosphamide bond to a lysine residue in the enzyme (Shuman and Hurwitz, 1981). The first step in the guanylyltransferase reaction is routinely assayed by transfer of 32P label from [α-$^{32}$P]GTP to the enzyme. Therefore, the inventors used this assay to test for guanylyltransferase activity copurifying with baculovirus RNA polymerase.

AcNPV RNA polymerase was purified from *S. frugiperda* cells infected with a recombinant baculovirus that overexpresses all four RNA polymerase subunits as described previously (Guarino and Summers, 1986). The purified RNA polymerase was filtered through a Superose 6 size exclusion column in 2 M KCl, and individual fractions were tested for RNA polymerase activity in the standard in vitro transcription assay (Xu et al., 1995). This assay uses two nucleoside-free templates that are separately linked to the late 39k gene and the very late polyhedrin gene. After incubation at 30° C., samples were extracted with phenol and RNA products were analyzed by acrylamide gels in the presence of 8 M urea. As previously shown, the baculovirus late promoters (FIG. 8A, lanes 2 to 7). The level of transcripts obtained was directly proportional to the amount of protein in each fraction, indicating that the enzyme was essentially homogenous.

The corresponding fractions were also analyzed for the formation of SDS-resistant GMP-protein adducts (FIG. 8B, lanes 2 to 7). A single radiolabeled protein that migrated as a 54-kDa species was detected in the autoradiographs of the resulting protein gels. The guanylyltransferase reactions contained only RNA polymerase, GTP, and divalent cation. Thus, the formation of the protein nucleoside was not dependent on the addition of DNA template, RNA product, or the other nucleotides. The amount of guanylate-enzyme (EpG) formed in each fraction was directly proportional to the amount of transcription activity (FIG. 8A, lanes 2 to 7). Physical association of the guanylyltransferase activity with RNA polymerase activity in 2 M salt strongly argues that guanylyltransferase was an integral component of the viral RNA polymerase complex.

The radiolabeled protein comigrated with the LEF-4 subunit of the polymerase complex (FIG. 8B, lane 8), suggesting that LEF-4 is the guanylyltransferase. Capping enzymes are members of a superfamily of nucleotidyltransferases, and members of this family bind nucleotides to an invariant lysine residue that is contained within a conserved KxDG motif This motif is present in all three of the baculovirus LEF-4 proteins that have been sequenced (motif I in FIG. 9). Five additional motifs have been noted for the capping enzymes and ligases (Wang et al., 1997), and these sequences are conserved in the same order and with similar spacing in the baculovirus proteins. Sixteen amino acids in these six motifs have previously been shown to be essential for function of the Saccharomyces cerevisiae capping enzyme (Wang et al., 1997). Comparison of these residues (underlined in FIG. 9) with the corresponding sequences in the baculovirus LEF-4s reveals that 10 of them are identical while 8 have conservative substitutions. This sequence comparison strongly supports the biochemical data suggesting that LEF-4 is a guanylyltransferase.

To confirm that lef-4 encodes a protein with guanylyltransferase activity, the inventors constructed a recombinant baculovirus that overexpressed LEF-4 under the control of the polyhedrin promoter. Infected cells were harvested at 48 h postinfection and separated into cytosolic and nuclear fractions. To determine the subcellular localization of overexpressed LEF-4, nuclear and cytosolic fractions were analyzed by denaturing PAGE (FIG. 10). Straining of total proteins with Coomassie brilliant blue revealed that LEF-4 was strongly overexpressed in the recombinant virus compared to the parental control, RP6-SC. Overexpressed LEF-4 was predominantly found in the cytosolic fraction. It has previously bee shown that LEF-4 is primarily localized in the nuclei of infected cells Durantel et al., 1998), as is the ciral RNA polymerase (Guarino et al., 1998). The failure of overexpressed LEF-4 to accumulate in the nucleus suggests that the LEF-4 subunit lacks a nuclear targeting signal and must rely on other components of the viral RNA polymerase for nuclear transport.

Cytosolic 3LEF-4 was purified by ion-exchange chromatography. LEF-4 bound to heparin-agarose of 50 mM KCI and eluted at 150 mM KCl. The peak fractions from heparin agarose were dialyzed and loaded onto a Mono Q column at 50 mM KCl. LEF-4 bound to Mono Q and was eluted at 230 mM KCl. The Mono Q peak was nearly homogeneous with respect to the 54-kDa band, as judged by Coomassie brilliant blue staining of SDS-polyacrylamide gels (FIG. 10, lane 1). Approximately 340 mg was obtained from 1 liter of vLEF-4 infected cells.

The peak of LEF-4 protein from the Mono Q column was further purified by filtration through a Superdex 200 column at 100 mM KCl. A single UV-absorbing peak eluted at 13.6 ml (FIG. 11A). Fractions corresponding to the peak of A280 were analyzed by SDA-PAGE, and a 54-kDa band was observed in the Coomassie brilliant blue-stained gels (FIG. 11B). Comparison of the elution volume for LEF-4 relative to marker proteins filtered through the same column indicated a molecular mass of 114,200 for the native protein. At 400 mM KCl, LEF-4 eluted from the same column at 14.8 ml, consistent with a monomer molecular mass of 47,600. This finding suggests that the 54-kDa LEF-4 protein forms a dimer in solution at physiological salt concentrations. The dimers dissociate into monomers at higher salt concentrations indicating that the interactions at the dimer interface are relatively weak. The baculovirus RNA polymerase complex is also a dimer of four subunits, but the polymerase dimer is stable at 2 M KCl (Guarino et al., 1998).

The Superdex 200 gel filtration fractions were analyzed for guanylytransferase activity by the GMP label transfer assay. A single radiolabeled protein that comigrated with LEF-4 was detected on autoradiographs (FIG. 11C). The peak of guanylyltransferase activity exactly coincided with thepeak of LEF-4 protein. These data confirm that LEF-4 is the guanylytransferase subunit of RNA polymerase.

Characterization of the guanylyltransferase reactions of RNA polymerase and LEF-4. With both purified LEF-4 and purified RNA polymerase, the amount of enzyme-guanylate formed was proportional to the amount of protein added (FIG. 12A). However, purified LEF-4 was not as active as the viral RNA polymerase in the guanylylation reaction. With purified RNA polymerase, approximately 15% of the protein was guanylylated in this experiment. This value varied from 7.5 to 20%, depending on the particular preparation. However, with the LEF-4 single subunit, the inventors consistently observed that less than 1% of the enzyme was guanylylated, and only 0.84% of the input enzyme was radiolabeled in this experiment. It has been established in other systems that the activities of guanylyltransferases in vitro are limited by the number of open sites for guanylation (Rankin et al., 1988). The Kms for GTP are usually below the in vivo concentrations of GTP, and thus most enzymes are isolated in the guanylylated form. Guanylytransferase reactions are reversible in the presence of PPI, which is the product of the reaction and therefore shifts the equilibrium resulting in release of GTP form the enzyme. Thus, the addition of low levels of PPI can stimulate the forward reaction by freeing occupied binding sites for subsequent reaction with radiolabeled GTP.

To test whether in vivo guanylylation was responsible for the low activity of the purified subunit, the inventors performed pyrophosphate titration experiments with both enzymes (FIG. 12B). The addition of low levels of pyrophosphate increased the formation of radiolabeled EpG with the purified RNA polymerase. The amount of guanylate-enzyme formed increased linearly to 62 $\mu$M PPI, and al. this concentration 92% of the input enzyme was radiolabeled. The results of this, experiment show that the trnsguanylylation reaction is freely reversible and that essentially all of the enzyme is catalytically active. Furthermore, this experiment serves to confirm that the LEF-4 subunit of purified polymerase is the guanylytransferase, as it is the only protein of that size that is present in stoichiometric amounts. Minor contaminants, if present, would be unlikely to bind GTP at the molar amounts observed in this experiment.

The amount of EpG formed with the purified LEF-4 submit was also increased in a linear fashion by the addition of low levels of PPI (FIG. 12B). However, the increase was modest compared to RNA polymerase. In the presence of 62 $\mu$M PPI 2.1% of the enzyme was guanylylated, only a 2.6-fold increase over that seen in the absence of pyrophosphate. This finding suggests that the low activity of the purified subunit compared to the holoenzyme is due to intrinsic differences between the two enzyme sources and not to preguanylylation of the enzyme in vivo.

Nucleotide specificity of the guanylytransferase activity of RNA polymerase. The guanylylation reaction showed high specificity for [$\alpha$-$^{32}$P]GTP, (FIG. 13A). There was no label transfer to the LEF-4 subunit of RNA polymerase in the presence of [$\alpha$-$^{32}$P]CTP, [$\alpha$-$^{32}$P]UTP, or [$\gamma$-$^{32}$P]ATP. Also no radiolabeled product was formed with [$\gamma$-$^{32}$P]dGTP (lane 7). However, the amount of labeled enzyme formed at this substrate concentration was 30-fold lower than with [$\alpha$-$^{32}$P]GTP, indicating that LEF-4 discriminates between ribose and deoxyribose sugars.

To further investigate the ribose specificity of LEF-4, a nucleoside triphosphate titration experiment was performed (FIG. 13B). With GTP, the yield of EpG increased linearly to 2.5 uM and reached at 1 $\mu$M . With dGTP as the substrate, the reaction was linear to 5 $\mu$M, and at this concentration 10-fold less product was formed with dGTP than with GTP. The formation of LEF-4—dGMP continued to increased slowly up to 40 uM dGTP (FIG. 13B), and at this concentration the amount of EpG was approximately 25% of that fgormed with saturating GTP. With dGTP, the reaction was half-maximal at 10 $\mu$M. These data confirm that RNA polymerase discriminates between the sugars and prefers ribose over deoxyribose.

Titration of GTP with the purified LEF-4 in the transguanylylation reaction. The formatin of guanylate-enzyme was linear with respect to increasing GTP up to 500 $\mu$M and continued to increase slowly up to 5 mM GTP (FIG. 13C). At saturating levels of GTP, approximately 30% of the input enzyme was guanylated in vitro. At 5 $\mu$M GTP, the optimal concentration for the guanylyltransferase activity of RNA polymerase, the reaction with LEF-4 was only 2.5% of maximal. Tiration of sodium pyrophosphate at 1 mM GTP increased the level of guanylation approximately threefold, indicating that nearly all of the protein was catalytically active. This finding confirms that the transguanylylation reaction is fully reversible by the addition of pyrophosphate. Furthermore, these experiments indicate that the low activity of the single subunit is primarily due to the fact that LEF-4 by itself binds GTP poorly, which suggests that assembly of LEF-4 into the RNA polymerase complex lowers the Km for GTP.

Cation dependence of the guanylyltransferase activity of RNA polymerase and of purified LEF-4. With both sources of enzyme, guanylyltransferase activity was dependent on the addition of a divalent cation (FIG. 14). For both LEF-4 and RNA polymerase, manganese was a more efficient cofactor than magnesium at concentrations below 10 mM, although the optimal concentrations differed for the two enzyme preparations. With RNA polymerase, activity was maximal between 0.6 and 10 mM, while the LEF-4 activity peaked at 5 mM. With both enzymes, activity declined between 10 and 20 mM. With magnesium as cofactor, the yield of guanylated RNA polymerase was proportional to the cation concentration between 0.2 and 1 mM $MgCl_2$, the standard concentration for in vitro transcription, the yield of EpG was 90% of maximal. Magnesium was less efficient as a cofactor for LEF-4 than for RNA polymerase. The guanylyltransferase activity gradually increased as a function of magnesium concentration, and reached saturation between 20 to 40 mM (FIG. 14B).

Example 6

RNA Polymerase has RNA 5'-triphosphatase and ATPase Activities

The guanylyltransferase domain is localized in the C-terminal half of the protein, which suggested to us that the N-terminal part of the protein might have additional functions. In support of this hypothesis, the inventors noted local sequence conservation with the triphosphatase domain of vaccinia virus capping enzyme (Yu et al., 1997), and biochemical assays confirmed that LEF-4 had RNA 5'-triphosphatase and ATPase activities (Jin et al., 1998). Additional tests demonstrated that both RNA 5'-triphosphatase and ATPase activities co-purified with the guanylyltransferase and transcription activities of AcNPV RNA polymerase (Jin et al., 1998). Further confirmation of both activities was provided by mutagenesis data showing that substitution of alanine at critical residues abolished the RNA 5'-enzymatic activities of LEF-4. 5'RACE experiments have confirmed that RNAs transcribed by baculovirus RNA polymerase are capped at the 5' ends (Jin and Guarino, unpublished).

Methods

Construction of LEF4-intein clones. The AcNPV genomic clone pHindIII-C was amplified by using Pfu I DNA polymerase. The 5' primer (CTGCAG<u>CCATGG</u>ACTACGGCGATTTTGTG) inserted at an NcoI site (underlined) at the ATG codon of LEF-4. The 3' primer (TTA<u>CCCGGG</u>CACGATTCGGTCGCG) was designed to substitute a glycine residue for the C-terminal aspartate and added a SmaI site (underlined) at the C-terminal glycine. The PCR products were cloned into pBluescript and screened by restriction enzyme digestion. A clone containing LEF-4 was digested with NcoI and SmaI and ligated to pCYB4 (New England Biolabs) previously digested with NcoI and SmaI. This plasmid directs the synthesis of a fusion protein containing a self-cleavable affinity tag under control of the tac promoter. Recombinant DNAs were screened by restriction enzyme digestion, and a clone with the correct size insert was sequenced. Alanine substitution mutations in LEF-4 were constructed by using a QuikChange site-directed mutagenesis kit (Stratagene) as recommended by the manufacturer. Potential mutant clones were verified by DNA sequence analysis.

Purification of LEF-4 from bacteria. *Escherichia coli* XL1-Blue cells containing pLEF4intein were grown to late log phase, and expression of LEF-4 was induced by the addition of 0.4 mM 5-bromo-4-chloro-3-indolyl-β-D-galactopyranoside. After induction, cells were incubated at 20 ° C. overnight. Cells were harvested by centrifugation, resuspended in buffer B (50 mM Tris [pH 7.9], 0.1 mM EDTA, 500 mM NaCl, 0. 1% Triton X-100), lysed by sonication, and clarified by low-speed centrifugation. The resulting supernatant was loaded onto a 2-ml chitin column. The column was washed with 20 volumes buffer B plus 30 mM dithiothreitol (DTT) and allowed to sit overnight in the presence of 30 mM DTT. Cleaved LEF-4 was eluted with 3 column volumes of buffer B plus 30 mM DTT. Sodium dodecyl sulfate (SDS)-polyacrylamide gel electrophoresis (PAGE) followed by staining with Coomassie brilliant blue showed a single protein that migrated in the expected position for LEF-4. LEF-4 was further purified by anion-exchange chromatography. Peak fractions were dialyzed against buffer A (50 mM Tris [pH 7.9], 0.1 mM EDTA, 1 mM DTT) containing 50 mM NaCl, and the protein was applied to a Mono Q HR 5/5 column (Pharmacia) previously equilibrated in the same buffer. The column was washed with 10 ml of loading buffer and then eluted with a 20-ml linear NaCl gradient from 50 to 500 mM. LEF-4 eluted from Mono Q in a single sharp peak at 230 mM NaCl. LEF-4 was quantitated by a Coomassie blue G250 binding assay performed as recommended by the manufacturer (Pierce).

Assay of LEF-4-GMP complex formation. Standard reaction mixtures (25 μl) contained 50 mM Tris-HCl (pH 7.9), 1 to 5 mM $MnCl_2$, 5 mM DTT, 5 μM [α-$^{32}$P]GTP, and purified RNA polymerase or LEF-4 as indicated. Samples were incubated for 15 min at 30° C. and then stopped by the addition of 1% SDS. Samples were boiled and electrophoresed through an SDS-8% polyacrylamide gels. Gels were fixed, dried, and exposed to film.

RNA triphosphatase assays. RNA 5'-triphosphatase activity was assayed by the liberation of [32P]$P_i$ from [γ-$^{32}$P] GTP-terminated RNA. Template RNA was synthesized by in vitro transcription of pBluescript KS DNA previously digested with BssHII. The linearized template was transcribed with T3 RNA polymerase, using standard conditions for in vitro transcription in the presence of [γ-$^{32}$P]GTP added at a final specific activity of 5,000 cpm/pmol. This produced a 150-nucleotide-long RNA transcript specifically labeled at the 5' end. γ-$^{32}$P-labeled RNA was purified from transcription reactions by three rounds of precipitation with 2.5 M LiCl, followed by standard ethanol precipitation. Standard RNA triphosphatase assay mixtures (20 μl) contained 50 mM Tris-HCl (pH 7.9), 5 mM DTT, 0.3 mM $MnCl_2$, 50 mM KCl, 1 to 5 μM RNA, and enzyme as indicated. Reactions were incubated for 15 min at 30 ° C. and then terminated by the addition of 1 M formic acid. Samples were applied to polyethylenimine (PEI)-cellulose thin-layer chromatography (TLC) plate (J. T. Baker) and chromatographed with 0.5 M $KH_2PO_4$ (pH 3.4). Reactions were quantitated by scanning the TLC plate in a FUJIX BAS PhosphorImager.

ATPase assays. Standard reaction mixtures (20 μl) contained 50 mM Tris-HCl (pH 7.9), 5 mM DTT, 50 mM KCl, 0.3 mM $MnCl_2$, 1 μM [γ-$^{32}$P]ATP or GTP, and enzyme as indicated. Reactions were incubated 15 min at 30 ° C., and aliquots were spotted on PEI-cellulose plates. Reactions were quantitated by scanning the plates with a PhosphorImager.

Results

The inventors have previously shown that the LEF-4 subunit of AcNPV RNA polymerase has guanylyltransferase activity, suggesting that LEF-4 is an RNA capping enzyme (Guarino et al, 1998). Furthermore, analysis of the LEF-4 amino acid sequence revealed homology to six motifs that are shared among viral and cellular guanylyltransferases in the C-terminal half of the protein. Sequence analysis of the N-terminal portion of the LEF-4 revealed homologies with the triphosphatase domains of capping enzymes in the poxviruses and African swine virus (FIG. 15). Two pairs of glutamic acid residues and a single arginine have been shown to be essential for the RNA triphosphatase and ATPase activities of vaccinia virus capping enzyme (Yu et al., 1997). These glutamates and arginines are present in AcNPV LEF-4 with a similar order and spacing as found in the vaccinia virus and African swine fever virus capping enzymes. Furthermore, these residues are conserved among all three of the baculovirus LEF-4 proteins that have been submitted to protein and nucleic acid databases. These similarities suggested to us that the LEF-4 subunit of baculovirus RNA polymerase may have RNA triphosphatase and ATPase activities in addition to guanylyltransferase function.

To test this hypothesis, purified AcNPV RNA polymerase was filtered through Superose 6 (FIG. 16A). As previously shown (Guarino et al., 1998), a peak of guanylyltransferase activity coincided with the peak of absorbance at 280 nm and the peak of polymerase activity (FIG. 16B). To test for RNA triphosphatase activity, γ-$^{32}$P-labeled RNA was prepared by in vitro transcription with T3 RNA polymerase in the presence of [γ-$^{32}$P]GTP. This produces an RNA transcript that is singly labeled in the gamma phosphate position at the 5' end of the RNA. RNA polymerase fractions were then incubated with 1 μM [γ-$^{32}$P]RNA in the presence of 1 mM $MnCl_2$. After incubation for 15 min at 30° C., free phosphate was separated from the RNA substrate by TLC on EPI-cellulose. As shown in FIG. 16B, RNA polymerase fractions catalyzed the hydrolysis of gamma phosphates from the RNA substrate. Furthermore, the extent of cleavage was proportional to input protein, and the peak of RNA triphosphatase activity exactly matched the peak of transcription activity. This finding indicates that RNA triphosphatase is an integral component of the baculovirus RNA polymerase.

To examine the specificity of the triphosphatase activity, fractions were also incubated with [γ-$^{32}$p]ATP, and the release of free phosphate was monitored by PEI chromatography. The peak of activity of gamma phosphate release exactly coincided with the three other enzymatic functions analyzed (FIG. 16B). Essentially identical results were obtained with [γ-$^{32}$P]GTP as the substrate. This finding suggests that the baculovirus enzyme, like the vaccinia virus capping enzyme, has nucleoside triphosphatase activity in addition to RNA triphosphatase activity.

RNA triphosphatase and the ATPase activities were due to LEF-4 and not to other components of the RNA polymerase. Purified LEF-4 was also assayed for both activities (FIG. 17). LEF-4 was overexpressed in baculovirus-infected cells and purified to near homogeneity by heparin-agarose and Mono Q chromatography as previously described (Guarino et al., 1998). Purified LEF-4 was then filtered through a Superdex 200 gel exclusion column. Fractions corresponding to the peak of UV absorbance were assayed for guanylyltransferase activity, using the GMP label transfer assay. The same fractions were also active in the RNA triphosphatase and ATPase assays. The specific activities of the three enzymatic functions were nearly constant across the peak of protein. This result is at consistent with the hypothesis that the triphosphatase and ATPase activities of RNA polymerase map to the LEF-4 subunit.

The RNA triphosphatase activity of LEF-4 was absolutely dependent on the addition of a divalent cation (FIG. 18A). Manganese was a more efficient cofactor than was magnesium at all concentrations tested. Activity peaked sharply at 0.3 mM and declined at higher concentrations. Magnesium was active over a broader range and was maximal at 1 mM, at which concentration the activity was 30% of that achieved with manganese. Essentially the same results were seen with RNA polymerase.

Under optimal conditions, the extent of gamma phosphate hydrolysis during a 15-min incubation was proportional to input protein with both sources of enzyme (FIG. 18B). In the linear range of enzyme concentration, the turnover number for RNA polymerase was 0.16 fmol/s/fmol of enzyme, while that of LEF-4 was 0.31 fmol/s/fmol.

Hydrolysis of ATP was also absolutely dependent on the addition of a divalent cation (FIG. 19A). In the presence of manganese, ATPase activity increased linearly from 0.08 to 0.6 $\mu$M and then declined slowly at higher concentrations. Magnesium was a poor substitute for manganese, unlike the results observed for magnesium in the RNA triphosphatase assays. The ATPase activity at 10 mM magnesium was only 1% of the maximal activity gained with manganese.

Specificity for the gamma phosphate was monitored by using [$\alpha$-$^{32}$P]GTP as a substrate (FIG. 19B). GDP accumulated linearly at a rate of 6.4 pmol/min/pmol of enzyme. GDP was slowly converted to GMP at a rate of 0.22 pmol/min/pmol of enzyme. Free phosphate was not detected during the 30-min time course.

RNA triphosphatase and ATPase activities observed were attributable to LEF-4. The inventors expressed three mutated versions of LEF-4. Four glutamates and one arginine corresponding to residues previously shown to be essential for vaccinia virus triphosphatase activity (Yu et al., 1997) were changed to alanine. The inventors also expressed a mutant protein in which the lysine residue of the guanylyltransferase KxDG motif was substituted with alanine. For ease of expression and purification, the mutant LEF-4 proteins were expressed in the E. coli expression system IMPACT I (New England Biolabs). This system produces fusion proteins with a self-cleavable intein tag linked to a chitin-binding domain. Cleavage of the intein tag produces a protein that is identical to the wild-type LEF-4 except for the substitution of a glycine residue for the C-terminal asparagine. This substitution does not affect the enzymatic activities of the protein, as all of the assays indicated that LEF-4 produced in E. coli was equivalent to native LEF-4 purified from baculovirus-infected cells (FIG. 20).

After elution from the intein column, the LEF-4 protein samples were further purified by Mono Q chromatography. FIG. 20 shows that the wild-type and mutant proteins expressed in E. coli were purified to single-band homogeneity. Guanylyltransferase assays were performed to ensure that the mutant proteins were correctly folded. The specific activities of the mutant and wild-type enzymes were determined within the linear range of enzymatic activity. With the wild-type enzyme, 0.5% of the available binding sites were radiolabeled, comparable to the level observed with native LEF-4 produced in baculovirus-infected cells (Guarino et al., 1998). The activities of the triphosphatase mutants were equivalent to that of the wild-type protein, with the exception of that of E9/11A, which was 2.5-fold higher than the activity of the wild-type protein. As expected, the guanylyltransferase activity of the K255A mutant was undetectable. It has been established in other systems that nucleotidyltransferases form covalent intermediates with adenylate or guanylate linked to the lysine residue of the KxDG motif (t, Myette and Niles, 1996). Thus, analysis of this mutation serves to demonstrate that the guanylyltransferase and triphosphatase activities are localized to separate domains.

RNA triphosphatase activities of the mutant and wild-type enzymes were assayed by release of $^{32}$Pi from 1 $\mu$M [$\gamma$-$^{32}$P] RNA. The wild-type protein hydrolyzed 210 pmol of Pi per pmol of protein in a 15-min incubation. RNA triphosphatase activity was undetectable in the E181/183A mutant, reduced 100-fold in the E9/11A mutant, and reduced to 2.5% of control levels in the R51A mutant. ATPase activities were assayed by release of $^{32}$Pi from 1 $\mu$M [$\gamma$-32P]ATP. The wild-type enzyme liberated 108 pmol of Pi per mol of LEF-4 in 15 min at 30° C. The activity of all three mutants was reduced to less than 1% of that of the control. The K255A mutant retained both RNA triphosphatase and ATPase activities. These data are consistent with results obtained with corresponding mutations in the vaccinia virus capping enzyme (Yu and Shuman, 1996).

The lef-4 gene was first described as the site of a mutation in a virus that was temperature sensitive (ts) for expression of late genes (Partington et al., 1990). The ts lesion in LEF-4 was mapped to a single-nucleotide transversion resulting in a substitution of phenylalanine for leucine at amino acid residue 105 (Carstens et al., 1994), within the RNA triphosphatase domain (FIG. 15). This finding suggested the possibility that the defect in late gene expression may be due to incomplete hydrolysis of the gamma phosphates of late transcripts and therefore inefficient capping of late transcripts. One function of the m7G cap is to protect mRNAs from degradation. Therefore, a defect in capping could lead to rapid turnover of late mRNAs, producing the phenotype observed in this mutant.

The inventors expressed a mutant L105F protein with this substitution as described above for the alanine substitutions. The protein was expressed at 20° C. and tested for guanylyltransferase, RNA triphosphatase, and ATPase activities at 25 and 33° C. As shown in FIG. 21A, the purity of the L105F protein was commensurate with that of the wild-type protein. Guanylyltransferase activities were also equivalent to those of the wild-type protein at both permissive and nonpermissive temperatures. With both mutant and wild-type proteins, the activity was slightly higher at 25 than at 30° C., while the activity was reduced by half at the higher temperature (FIG. 21B). The wild-type protein bound GMP to an extent that occupied 0.7% of available sites at 25° C. and only 0.2% at 33° V. The activity of the, mutant protein was approximately 85% that of the wild type at both temperatures. These data indicate that substitution of the phenylalanine for leucine did not lead to temperature-dependent unfolding of LEF-4.

The RNA triphosphatase and ATPase activities of L105F were determined by protein titration at the permissive and nonpermissive temperatures. Both activities were indistinguishable from that of the wild-type protein at the permissive temperature. At the nonpermissive temperature, the ATPase activity of the ts mutant was equivalent to wild-type activity but the RNA triphosphatase activity was reduced to 74% of the wild-type level. Mutational analyses of the vaccinia virus capping enzyme indicate that the RNA triphosphatase and ATPase activities map to the same active site (Myette and Niles, 1996; Yu and Shuman, 1996). Therefore, it is possible that this residue maps to an RNA binding site rather than to the catalytic site. However, this effect is minimal and unlikely to account for the ts phenotype observed for the LEF-4 mutant virus.

The activities of L105F were investigated at the nonpermissive temperature. Thermal inactivation profiles for the three enzymatic activities were produced (FIG. 22). Wild-type and L105F proteins were incubated at the permissive (25° C.) or nonpermissive (33° C.) temperature for defined lengths of time and then tested for guanylyltransferase and triphosphatase activities at the nonpermissive temperature. In addition, the inventors analyzed the effect of preincubation at 37° C., which is higher than the nonpermissive temperature in vivo.

The temperature inactivation profile for the guanylyltransferase activities indicated that both wild-type and mutant enzymes were sensitive to incubation at elevated temperatures (FIG. 22A). After 30 min at 37° C., the activity of the wild-type enzyme was reduced to 1% of control levels (no preincubation). Incubation for 30 min at 33 or at 25° C. reduced activity to approximately 20% of control levels. At 25 and 33° C., the inactivation profiles of the L105F mutant mirrored those of the wild type, and the values averaged 87% of wild-type values. At 37° C., the difference between the two proteins was greater. The activity of L105F was averaged 50% of that of the wild type after incubation at 37° C.

ATPase profiles were similar for the wild type and L105F. The activities of both enzymes in ATPase assays decreased approximately 50% after 30 min of preincubation at 25° C., 56% at 33° C., and 74% at 37° C. RNA triphosphatase activities showed the highest level of thermal stability for both proteins. The inactivation profiles for L105F and the wild type were indistinguishable at 25 and 33° C., with both enzymes losing only 10% of their activities after 30 min of preincubation. L105F was somewhat more sensitive than the wild type to incubation at 37° C. and retained only 60% of its activity after 30 min, while the wild-type enzyme retained 78% of its activity.

As yet, an RNA methyltransferase activity in the viral RNA polymerase has not been identified. Thus the RNAs would be capped but not methylated. However, this is unlikely to affect the translation efficiency or stability of the RNAs because (GpppG caps are rapidly methylated after addition to cell-free protein synthesizing extracts or after transfection into eukaryotic cells (Gallie, 1991).

Example 7

3' End Processing by Baculovirus RNA Polymerase

Transcripts made by the baculovirus RNA polymerase are capped at the 5' ends (Guarino et al., 1998a,b; Jin et al., 1998) and polyadenylated at the 3' ends (Jin and Guarino, unpublished). Both of these modifications are essential for function and stability of eukaryotic mRNAs, and baculoviruses are unusual in that they are nuclear viruses that encode proteins with these functions. Vaccinia virus also encodes its own RNA polymerase and RNA processing enzymes, but vaccinia replicates in the cytosol and, so must encode its own enzymes because it does not have access to the cellular transcription machinery. The baculovirus RNA polymerase is also unusual in that it is composed of only four subunits, and thus is very simple in structure as compared to enzyme complexes needed for transcription and processing in eukaryotic cells. A typical eukaryotic cell needs 3 or more large protein complexes for promoter recognition, a 12-subunit complex for RNA synthesis, three enzymes for capping, and 5 proteins for cleavage and polyadenylation. Even vaccinia virus RNA polymerase is a large enzyme complex of nine subunits, with a two subunit complex for capping and a two subunit complex for polyadenylation. In its simplicity, the baculovirus RNA polymerase is more similar to the bacterial and bacteriophage enzymes.

Methods

Construction of DNA template for transcription termination assay. A SwaI recognition site was inserted in the C-free cassette of Polh/CFS plasmid (Xu et al., 1995), using a QuikChange site-directed mutagenesis kit (Stratagene) as recommended by the manufacturer. Potential mutant clones were identified by restriction digestion and then verified by DNA sequence analysis. The mutant plasmid was linearized with SwaI and then ligated to a 47-bp synthetic globin sequence. A plasmid containing an insert in the correct orientation was identified by DNA sequence analysis and named Polh/CFS-T. The other mutants in the synthetic globin sequence were constructed using same procedure with the appropriate mutant oligonucleotides.

In vitro transcription assays. In vitro transcription assays for transcription termination reactions were carried out using conditions previously described (42), with some modifications. Briefly, 50 µl of transcription reaction mixture contains 0.2 pmol of purified RNA polymerase, 50 mM Tris (pH 7.9), 100 mM KCl, 2 mM $MgCl_2$, 5 mM STT, 0.1% 3-[(3-cholamidopropyl)-dimethylammonio]-1-propanesulfonate (CHAPS), 1 mM each ATP and UTP, 20 µM GTP, 5 µCi of [$\alpha$-$^{32}$P]GTP, 8 U of RNasin, 0.2 U of inorganic pyrophosphatase, 0.2 pmol of Polh/CFS or Polh/CFS-T. Reaction mixtures were incubated at 30° C. for 15 min. The reactions were stopped by adding 150 µl of stop buffer (20 mM Tris [pH 7.5], 0.1% sodium dodecyl sulfate [SDS], 1 mM EDTA, 400 mM NaCl, 50 µg of tRNA/ml). RNA transcripts were extracted once with an equal volume of phenolchloroform and precipitated by adding a 2.5× volume of 100% ethanol at −80° C. for 30 min. After centrifugation at 4° C., the RNA was resuspended into sequence stop buffer and resolved on a 6% polyacrylamide-8 M urea gel. The gel was dried and exposed on Kodak film or PhosphorImager plates.

Northern blot analysis. After in vitro transcription, RNA transcripts were resolved on a 6% polyacrylamide-8 M urea gel and transferred to nylon membrane with 0.6×Tris-borate-EDTA (TBE) buffer at 16 V at 4° C. for 16 h. The RNA transcripts were then cross-linked to the nylon membrane using a Stratagene UV cross-linker. The membrane was prehybridized in hybridization bugger (6×SSPE (1×SSPE is 0.18 M NaCl, 10 mM $NaH_2PO_4$, and 1 mM EDTA [pH 7.7]), 10 mM EDTA, 5×Denhardt's solution, 0.5% SDS, 100 µg of sheared calf thymus DNA/ml, 25% formamide) at room temperature for 2 h and then a biotin-labeled oligonucleotide prove (10 mg/ml) was added to hybridize for 16 h. After hybridization, the membrane was rinsed with 2×SSC (1×SSC is 0.15 M NaCl plus 0.015 M sodium citrate)–0.1% SDS, washed in 0.2×SSC–0.1% SDS for 15 min twice, and then washed in 2×SSC for 5 min once at room temperature. The hybridization signals were detected by alkaline phosphatase-conjugated steptavidin (Gibco) and developed with nitroblue tetrazolium and 5-bromo-4-chloro-3-indolylphosphate as substrates.

Synthesis of RNA templates for in vitro cleavage assays. PCR was performed using Pfu DNA polymerase with Polh/CFS or Polh/CFS-T plasmid as DNA template and two oligonucleotides (<u>GCGGTACCATTTAGTGACACTATAG</u>AAGTATTTTAGTGTTTTTGTAATT TGTAATAAAAAAATTATAAATGGG and

GGCCTCGAGCTCCATACCCTTCCTCATCTATACCACCC as primers. The underlined sequence corresponds to the SP6 promoter; the remaining sequences hybridize to the C-free cassette. PCR products were inserted into a pUC18 plasmid previously linearized with SmaI. The resulting plasmids were called SP6/CFS and SP6/CFS-T. The RNA templates were synthesized using SP6 RNA polymerase and purified on an agarose-TBE gel.

RNA 3' RACE. Transcription reactions were performed as described above but incubated at 30° C. for 60 min. Then the RNA transcripts were precipitated with 5 μg glycogen and 2 volumes of ethanol at −80° C. for 30 min. RNA pellets were resuspended into diethylpyrocarbonate-treated sterile water. The RNA samples were then used to make the first-strand cDNA using Superscript II reverse transcriptase (Gibco) with the oligo(dT) adapter primer (AP primer; GGCCACGCGTCGACTAGTAC) as recommended by the manufacturer. Reverse transcriptase reactions were performed in the absence of dGTP. Then the first-strand cDNA was amplified by PCR with Taq DNA polymerase (Promega), an abridged universal amplification primer (AUAP primer; GGCCACGCGTCGACTAGTAC) corresponding to sequence beyond oligo(dT) of the AP primer, and a 3' RACE (rapid amplification of 3' cDNA ends) primer (TGGAGGGGATATGGAAAGGGAAAGGAG) corresponding to the upstream region of the C-free cassette. The PCR products were ligated with a linear T vector (Promega). The 3'-end sequences of RNA transcripts were determined by sequencing using the primers that hybridized to sequences on the T vector flanking the insert.

RNA 5' RACE. After in vitro transcription, RNA transcripts were resolved on a denaturing 60% acrylamide-8 M urea gel. The 130-nucleotide (nt) transcripts were excised, crushed in buffer, and purified by centrifugation through a spin column. RNA transcripts were then precipitated by the addition of 5 μg of glycogen and 2 volumes of ethanol at −80° C. for 30 min. The RNA pellets were resuspended in diehtylpyrocarbonate-treated sterile water. The RNA samples were then used to make the first-strand cDNA using Superscript II reverse transcriptase (Gibco) in the absence of dGTP, using a 3' primer (CTCCATACCCTTCCTCCAT) that hybridized to the C-free cassette. The cDNA samples were purified on a Sphadex G-80 spin column to remove the free nucleotides. The first-strand cDNAs were tailed using terminal deoxynucleotidyltransferase (Gibco) in the presence of 1 mM dGTP. The dG-tailed cDNAs were amplified with Taq DNA polymerase (Promega) with 3' long primer (GGCCTCGAGCTCGCGTCGACTAGTACCCCCCCCC CCCCCCCC). The PCR products were ligated with linearized T vector (Promega). The 5' ends of the RNA transcripts were determined by sequencing using the primers that annealed to sequences on the T vector flanking the insert.

Results

Baculovirus RNA polymerase terminates within the synthetic globin sequence. Previous studies have shown that a synthetic globin cleavage/polyadenylation signal directs 3'-end formation in vivo as well as the native polyhedrin signal (Westwood et al., 1993). To determine whether purified baculovirus RNA polymerase recognizes this globin signal in vitro, a 47-nt C-free version (FIG. 23A) was inserted into the template region of Polh/CFS, the transcription template used for purification of viral RNA polymerase (Guarino et al., 1998 ;Xu et al., 1995). The resulting construct, Polh/CFS-T, should direct the synthesis of a 286-nt transcript if the signal is not recognized by the baculovirus RNA polymerase (FIG. 23B). Alternatively, if RNA polymerase terminates transcription or cleaves the RNA transcripts within the globin signal, then the RNA products should be approximately 88 nt shorter than those transcribed from the standard Polh/CFS template.

In vitro transcription reactions were performed in parallel with purified RNA polymerase and either the standard Polh/CFS template or Polh/CFS-T. The transcription products were resolved on a denaturing polyacrylamide gel to compare the sizes of the transcription products. As usual, in vitro transcription with Polh/CFS template produced two transcripts (FIG. 23C, lane 2). The major band was 239 nt, which corresponds to the full-length transcript that initiates at TAAG and stalls at the first C in the nontemplate strand. The minor one was approximately 50 nt shorter than the full-length RNA transcripts. The origin of this shorter transcript is unknown, although the inventors have speculated that it is a pause product (Xu et al., 1995). In vitro transcription reactions with Polh/CFS-T generated four different RNA products (FIG. 23C, lane 3). The size of the largest band, 286 nt. corresponds to the size predicted for initiation at the polyhedrin promoter and stalling at the first C on the nontemplate strand. The minor band at 239 nt is probably equivalent to the pause product seen with Polh/CFS. The shorter two bands were unique to the transcription reaction with Polh/CFS-T. The major product was a heterogeneously sized band of approximately 170 to 220 nt. There was also a less abundant transcript of 130 nt.

To confirm that this transcription pattern was due to intrinsic properties of baculovirus RNA polymerase and not to contaminants in the enzyme preparation, the inventors assayed for copurification of this transcription pattern with RNA polymerase (FIG. 23D). The last step in the purification protocol is a Superose 6 gel exclusion column in the presence of 2 M KCl to disrupt nonspecific interactions with other proteins (Guarino et al., 1998). Aliquots of the individual fractions from the Superose column were analyzed by polyacrylamide gel electrophoresis (PAGE) to confirm the purity of the enzyme preparation (FIG. 1D, top). The corresponding fractions were also assayed for transcription activity on Polh/CFS-T. As expected, the total transcription activity increased and decreased concomitantly with the peak of RNA polymerase. The pattern of transcripts produced was identical in every fraction, indicating that minor contaminants probably do not contribute to the pattern observed (FIG. 23D, bottom). The peaks of protein and transcription activity also exactly copurified with the guanylyltransferase activity of the RNA polymerase.

The inventors consider the possibility that the two smaller RNAs were transcriptional pause products resulting from the low concentration of GTP used in the in vitro transcription reactions; [α-$^{32}$P]GTP is used as the radiolabel, and so the GTP concentration is 50 times lower than the concentration of other nucleotides. To test this, reaction products from a 15-min reaction (FIG. 24, lane 2) were chased with 1 mM GTP (lane 4). All four of the major bands, including the 130- and 170- to 220-nt transcripts, were resistant to the GTP chase (lane 4). This indicates they are not transcriptional pause products due to limiting GTP concentration. Other minor products, however, were chased by the addition of GTP, confirming that polymerase was still active and able to extend paused products. Addition of 1 mM CTP and 1 mMGTP chased the 130-nt product as well as the 239- and 286-nt transcripts (lane 5), indicating that these transcripts were in stable ternary complexes that stalled at the first C on the nontemplate stand. The 170- to 220-nt fragments, however, were not extended, indicating that these transcripts were no longer associated with RNA polymerase ternary complexes.

Northern blot analyses were performed to confirm this result. Parallel in vitro transcription reactions with both templates were performed and separated by acrylamide gel electrophoresis. The reaction products were transferred to nylon membrane and exposed to film to locate the positions of the reaction products (FIG. 25B). Blots were then separately probed with biotin-labeled oligonucleotides that corresponded to unique sequences that mapped to either the 5' or 3' region of the C-free cassette. Both probes hybridized to the full-length transcripts, as expected. The 170- to 220-nt transcripts hybridized with only the 5' probe, while the 130-nt band hybridized with the 3' probe but not the 5' probe (FIG. 25C).

Purified RNA polymerase has polyadenylation, but not cleavage activity. The results of the Northern blot analysis combined with the CTP chase data indicate that the 5' ends of the 170- to 220-nt transcripts mapped to the polyhedrin promoter, and so the 3' ends must map to positions within, or downstream of the globin sequence. The 3' ends of the 130-nt transcripts, on the other hand, must correspond to the last nucleotide of the C-free cassette. This positions the 5' ends of 130-nt transcripts at the extreme left end of the globin cassette, apparently upstream of the 3' ends of the 170- to 220-nt transcripts. This would suggest that these two bands were not produced by cleavage of the full-length transcript. Also arguing against a cleavage hypothesis is the fact that the relative molar amounts of the two products are not equivalent. The 170- to 220-nt fragments were present at an approximately fivefold molar excess compared to the 130-nt band.

The inventors assayed directly for posttranscriptional RNA cleavage activity associated with RNA polymerase. The Polh/CFS and Polh/CFS-T cassettes were cloned under the control of the SP6 promoter, and RNA transcripts were synthesized using SP6 RNA polymerase. Transcripts made by SP6 RNA plymerase are identical to the baculovirus RNA polymerase-derived RNAs except for an additional G at the 5' end. SP6 RNA polymerase-derived RNA transcripts were incubated with purified baculovirus RNA polymerase for 15 min at 30° C. in the standard in vitro transcription buffer (FIG. 26). RNAs were then analyzed for cleavage activity on a 6% polyacrylamide—8 M urea denaturing gel. RNAs were stable in both the presence and absence of RNA polymerase, indicating that they were not cleaved by the enzyme and also did not self-cleave. Addition of ATP along or ATP plus GTP and CTP resulted in the formation of longer, heterogeneously sized products, suggesting the RNA substrates were polyadenylated (FIG. 26, lanes 5, 6, 10, and 11). The polyadenylation reaction was apparently not sequence dependent, since the two transcripts were elongated to similar extents.

This polyadenylation activity of the purified RNA polymerase suggests that heterogeneity of the 170- to 220-nt transcripts was due to polyadenylation of the terminated transcripts. To test this, we performed a time course experiment with Polh/CFS-T plasmid (FIG. 27). If the terminated transcripts were polyadenylated, they should be elongated with the extended reaction time. Alternatively, if heterogeneity was due to random termination or cleavage, the sizes should not change with time of incubation.

Analysis of the time course experiment revealed that all four reaction products were synthesized by 5 min of incubation. The amount of product increased somewhat between 5 and 10 min of incubation, but the four bands were relatively constant in abundance at the later time points. The reaction products were constant with respect to size, with the exception of the 170- to 220-nt transcripts, which were elongated with increasing time. At later times the heterogeneous transcripts ranged in size from 200 to >400 nt, with an average length of approximately 250 nt.

Significantly, the amount of fall-length product did not decrease with time, and there was no evidence of cleavage of this product. This supports the conclusion that the shorter RNAs are not produced by cleavage of the full-length transcript. Thus, these data suggest a model in which the 170- to 220-nt transcripts arise by termination of transcription, followed by posttranscriptional polyadenylation.

Viral RNA polymerase terminates at a T-rich region in the globin cleavage/polyadenylation sequence. To determine the site of transcription termination, the 3□ RACE using oligo (dT) for the initial reverse transcription reaction. Sequencing of cDNA clones revealed the presence of a poly(A) tail, confirming that the transcripts were indeed polyadenylated. The 3' ends of these transcripts were mapped to the two T-rich regions of the synthetic globin sequence (FIG. 27B). Several clones had two additional, nontemplated T residues before the poly(A) tail. This suggests that baculovirus RNA polymerase may terminate by a slippage mechanism.

The inventors also performed RNA 5' RACE on the transcription products to determine the origin of the 130-nt product. Sequence analysis revealed that the 5' end of this transcript mapped to the poly(A) signal AATAAA (FIG. 26B). Therefore, the 130- and 170- to 220-nt transcripts could not possibly arise by cleavage of the fall-length product, since their 5' and 3' ends overlap. Presumably, the 130-nt product is produced by internal initiation of transcription, although there is not a consensus baculovirus late promoter motif (A/GTAAG) near the putative transcriptional start site. The poly(A) signal is followed by an AG dinucleotide, and it is possible that the resulting sequence ATAAAAG is read as a transcription start site in this in vitro system.

To confirm that the 130-nt transcripts were due to internal initiation and not to cleavage of the full-length transcript, the inventors used the construct SP6/Polh-T as a transcription template with purified RNA polymerase (FIG. 28A). This plasmid has the same C-free termination cassette as Polh/CFS-T but has a bacteriophage SP6 promoter instead of the baculovirus polyhedrin promoter. The inventors found that 130-nt transcripts were transcribed by purified viral RNA polymerase from this template (FIG. 28A, lane 3). Transcripts were not synthesized from a similar plasmid in which the AATAAA motif was changed to AGGAAA, confirming that this sequence directed internal initiation of transcription.

Oligo(T) is the major determinant for transcription termination. The synthetic globin sequence has two major sequence features of RNA polymerase II cleavage/polyadenylation signals; an AAUAAA motif located 10 to 30 bases upstream of the cleavage site and a GU-rich sequence 20 to 40 bases downstream. To determine whether these sequence features are essential for transcription termination by baculovirus RNA polymerase, the hexanucleotide AATAAA in the globin C-free cassette was changed to AGGAAA (Polh/CFS-M3) and the T residues in the CGT-rich sequence were changed to A's (Polh/CFS-M1). The ability of these mutant versions to direct transcription termination was tested by in vitro transcription. The termination activity of viral RNA polymerase was not affected either by substitutions in the GT-rich sequence (FIG. 28B, lane 3) or by the poly(A) signal mutation (FIG. 28B, lane 5). This indicates that neither of these sequence features is a major determinant for termination in vitro.

However, transcription of the hexanucleotide mutant produced two alterations in the pattern of transcription products (FIG. 28B), lane 5). The 130-nt product was not produced. This was expected from the results presented in FIG. 28A, showing that the sequence surrounding the poly(A) signal could function as a weak initiator. Also a transcript of approximately 160 nt was produced; this is apparently a transcription pause product, because it could be chased by the addition of 1 mM GTP.

Sequence analysis of 3' RACE products indicated that termination occurred at the two T-rich sequences of the synthetic globin C-free cassette (FIG. 27B). Therefore, the inventors also constructed mutant versions of Polh/CFS-T to test whether T-rich sequences are required for transcription termination. Both of the T-rich sequences were changed to TTGGGTT to make the double mutant Polh/CFS-M2, in which both of the T-rich sequences were disrupted by G residues. In vitro transcription reactions were then performed to compare the transcription patterns between Polh/CFS-T and the double mutant Polh/CFS-M2. Termination was completely abolished during transcription of this mutant template (FIG. 28B, lane 4). This result confirms the hypothesis that the globin termination cassette was able to function in 3'-end formation because it contained T-rich sequences, not because it was recognized by cellular cleavage/polyadenylation enzymes.

The mutation in the T-rich regions also resulted in a dramatic decrease in the production of the nonspecific initiation product at 130 nt. This suggests that the ability of the ATAAAAG sequence to serve as an initiator is strongly influenced by any probably dependent on, the presence of a T-rich sequence immediately downstream.

Transcription termination by baculovirus RNA polymerase is an energy-uncoupled process. In some systems, termination of transcription requires ATP to provide the energy to break the hydrogen bonds between the template and the transcript. Previous data from the lab have shown that transcription initiation and elongation are independent of ATP hydrolysis and are able to proceed in the presence of 1 mM ATP-yS (B. Xu and L. A. Guarino, unpublished data). To test whether transcription termination is coupled to ATP hydrolysis, 1 mM ATPyS was substituted for ATP in a transcription assay with Polh/CFS-T plasmid. There were no differences in either the transcription or termination patterns in parallel reactions containing ATP or ATPyS (FIG. 29). These data indicate that transcription termination by baculovirus RNA polymerase does not require ATP hydrolysis.

S1 mapping of baculovirus RNAs revealed the presence of canonical AAUAAA motifs upstream of most 3' ends (Westwood et al., 1993 and references therein). This suggested to many researchers that 3' ends were formed by the cellular cleavage/polyadenylation machinery. Experiments by Westwood et al. (1993) seemed to support this hypothesis. They analyzed alternative poly (A) signals and found that a synthetic globin sequence (AATAAAAGATCTTTATTTTCATTAGATCTGTGTT GGTTTTTTTGTGT) functioned as well as the native polh signals in baculovirus expression vectors. This globin sequence has the two major determinants of an efficient cleavage/polyadenylation signal: an AAUAAA sequence 10–30 bases upstream of the cleavage site and a GU-rich motif located 20–40 bases downstream. So for many years, most of the baculovirus community assumed that host enzymes were responsible for 3' end formation. Furthermore, many baculovirus vectors were developed with the SV40 cleavage and polyadenylation signal sequences, assuming that they would be more efficient than the native polyhedrin sequences.

Example 8

3' End Processing Using C-free Cassettes

The inventors to reevaluate this dogma, because of recent reports showing that cleavage and polyadenylation enzymes are targeted to their substrates through interactions with the CTD of RNA polymerase II (Dantonel et al., 1997; McCracken et al., 1997a,b). The inventors also noted that the 3' non-coding regions of baculovirus genes tend to be very A+T rich, and that the AATAAA sequences are not consistently located 10–30 bp upstream. This suggested to us that the presence of these sequences might be coincidental and not functional. T-rich motifs, however, were consistently located near the 3' ends of transcripts. The globin signal also contains at least one oligo(T) region. Oligo(T) is common to termination signals found in E. coli and vaccinia virus genes (Platt, 1986; Yuen et al., 1987). Thus, the inventors developed an alternative hypothesis that was consistent with 3' mapping data and the results of Westwood et al. (1993). Therefore, the inventors hypothesized that transcription of viral late genes terminated at oligo(T), and that messages were polyadenylated either by a template slippage mechanism catalyzed by the viral RNApol or by a viral-encoded poly(A) polymerase.

To test this hypothesis, a C-free version of the synthetic globin termination sequence was inserted 88 nt from the 3' end of the standard polh/CFS template (FIG. 30). The new construct polh/term should yield a transcript that is 47 nt longer than the transcript than polh/CFS template if the termination signal is not used. If the signal is recognized then polh/term should yield a shorter product of 198 nt. If the transcript is terminated and polyadenylated, then a heterogeneously sized product would be produced.

As shown in FIG. 30B, transcription from the termination cassette produced a transcript of a length that corresponds to initiation at ATAAG and termination at the oligo(T) region. In addition, a product was observed that is 47 nt longer than the standard template. This indicates that approximately 50% of the transcripts were terminated correctly, but polymerase read through the termination signal in the other half of the RNAs.

Considerable heterogeneity was observed in the size of the terminated transcript, suggesting that it may be polyadenylated. To confirm this and to map the termination site, 3' RACE was performed on the transcription products using oligo(dT) as primer for the reverse transcription reaction. Sequencing of many clones revealed the presence of a poly(A) tail, confirming that the transcripts were polyadenylated. The 3' ends of the transcripts were heterogeneous and mapped to the T-rich regions within the globin termination cassette (FIG. 31).

Example 9

A Bacterial Expression System for Baculovirus RNA Polymerase

The Guarino lab currently purifies baculovirus RNApol from insect cells infected with baculovirus recombinants that overexpress all four subunits of RNApol. The yields the inventors obtain are low, but acceptable, for experimental purposes but not for commercial production. In addition, the baculovirus system is not suitable for commercial production of RNApol due to the expense of culturing insect cells. Therefore, the inventors want to develop a bacterial expression system for baculovirus RNA polymerase.

The LEF-4 protein has already been overexpressed in bacteria (Jin et al., 1998). The enzyme was isolated in soluble form and, after purification, was found to be enzymatically identical to that produced in insect cells. Overexpression of the other three subunits has not been as successful. The LEF-8, LEF-9 and p47 subunits are highly expressed, but are insoluble. The inventors are currently trying several different strategies to improve solubility, including the use of different promoters, expression at lower temperatures, and expression in cells that overexpress the bacterial chaperone proteins GroES and GroEL. In addition, the inventors are constructing an expression vector that will permit expression all four subunits in one cell controlled by single promoter (FIG. 32). The inventors expect that simultaneous expression of all four subunits results in proper folding and assembly into an active complex. This strategy was successful for the expression of DNA polymerase-α-primase in E. coli (Schneider et al., 1998; Nasheuer, pers. comm). This is also a four-subunit complex that could only be expressed in soluble form when all four genes were cloned into the same expression vector.

Example 10

A Large-scale Purification Protocol for Baculovirus RNA Polymerase

E. coli cells are transformed with pET-RNApol. This construct, which allows expression of all four subunits in one cell, yields an active and largely soluble holoenzyme complex. Initially, fermentations on the scale of 1–4 liters are attempted to ensure that expression and solubility are satisfactory before scaling up to the 72-liter scale. The inventors experiment with fermentation conditions (temperature, media, induction regime, etc.) in order to maximize yields. Co-induction of all four subunits and solubility of the proteins is monitored by SDS-PAGE.

After induction, cells are lysed and the soluble proteins collected. Several routine batch fractionation steps, followed by standard open column chromatography are used to purify the RNA polymerase. Enzymatic activity is assayed using the standard transcription assay. Purification is monitored by electrophoresis on SDS gels stained with Coomassie blue. With cell yields of 5–10 g/liter, expression levels of 1–10%, and an overall recovery of 25% after purification, the inventors expect to obtain 15–300 mg of RNA polymerase at 99% purity from a 72-liter production run.

Enzymatic purity of the RNA polymerase is determined by performing standard assays for deoxyribonuclease, ribonuclease, triphosphatase, polynucleotide phosphorylase, etc. These enzymes interfere with in vitro transcription assays, and their absence is critical in order to carry out the other experiments. Additional polishing steps may be required to obtain enzymatic purity. This may simply involve re-chromatography on one or two of the original column materials, or employment of a different sorbent that can be shown to remove the interfering activity. The inventors monitor for protease contamination by examining the SDS-PAGE gel patterns of subunits during purification and in the purified enzyme. Absence of proteolysis is crucial for long-term storage of the enzyme in house, in a customer's freezer, as well as during the shipment process. Proteolysis may also modify the enzymatic properties with time and must be eliminated.

Functional assays are carried out to ensure that the enzyme preparation possesses the intrinsic transcription, capping, and polyadenylation activities described above.

Example 11

Analysis of Promoter Specificity

The precise sequences that define a baculovirus late promoter have not been systematically identified, although evidence suggests that specificity is conferred by a conserved 12 bp sequence surrounding the essential core (Guarino and Smith, 1992; Rankin et al., 1988; Rohrmann, 1986). Transcription initiates within the (A/G)TAAG motif, and substitution of any of the residues within TAAG completely inhibits transcription (Possee and Howard, 1987). Several lines of evidence suggest that (A/G)TAAG alone is not sufficient for transcription initiation. First, linker scan mutations that introduce substitutions within the 12 bp flanking the TAAG decrease transcription. In addition, there are (A/G)TAAG motifs in the baculovirus genome that are not utilized as promoters in infected cells, suggesting that the surrounding sequence context is not favorable for binding of polymerase (Blissard and Rohrmann, 1989). Furthermore, the inventors have observed that introduction of ATAAG motifs into the standard C-free cassette were not recognized as promoters by the viral RNA polymerase (Jin and Guarino, unpublished).

In order for baculovirus RNA polymerase to be useful as a research tool, it must have a high degree of promoter specificity and not recognize cryptic promoter motifs within target genes. Because the exact sequence that is recognized by the viral RNA polymerase has not been completely defined, this has been a concern among users of the baculovirus expression system. Some instruction manuals for baculovirus vectors caution researchers to search the DNA sequence of a target gene for ATAAG motifs (O'Reilly, 1992), although there are no published reports demonstrating that initiation of transcription at cryptic sites has been observed. The sequence (A/G)TAAG occurs less frequently in baculovirus genomes than would be predicted for a random 5-nt sequence. On average it occurs at approximately 30% the predicted level, so there is selective pressure against this sequence in non-promoter regions.

The inventors use a combined approach to define the promoter specificity of the baculovirus RNA polymerase. First, the inventors conduct saturation mutagenesis of the 12 nucleotides surrounding the TAAG motif, individually substituting each nucleotide with the other three possible bases. Transcription assays are performed using purified RNA polymerase and the standard C-free cassette. Template and polymerase are titrated in order to quantitatively determine the effect of substitution at each base.

The inventors also conduct run-off transcription assays using plasmids that contain each of the 217 (A/G)TAAG motifs in the AcNPV baculovirus genome (Ayres et al., 1994). These plasmids are already available in the Guarino lab, and the complete sequence of the genome is known so that restriction enzyme sites can be picked that will permit synthesis of appropriately sized fragments. Although 217 promoters may sound like a large number to analyze, it is really not, because many of the baculovirus late open reading frames contain multiple promoter motifs. Thus, it is possible to analyze many of the (A/G)TAAG motifs simultaneously. This analysis complements the saturation mutagenesis and allows us to compile an empirical list of favored promoter sequences.

Example 12

Production of Monoclonal Antibodies Against the Purified Transcription Complexes The purified transcription complexes LEF-4, -8, -9, and p47 are separately injected into mice in order to raise monoclonal antibodies against the individual subunits (Harlow and Lane 1988). Monoclonals against ubiquitin (Guarino et al., 1995), LEF-3/SSB (Hang et al., submitted), LEF-1 and LEF-2 have been produced. Based on the yield obtained in the initial experiment, the inventors estimate that the inventors need to purify complex from 5–10 liters of cells for the inoculations and screening of monoclonals, and this should be obtainable. The monoclonals may be used to monitor expression and intracellular localization of RNA polymerase subunits. The antibodies are also used to confirm that the proteins are associated into a complex by radioimmunoprecipitation (RIP) experiments using extracts prepared from infected cells labeled with $^{35}$S-methionine.

In addition, the inventors attempt to develop an immunopurification protocol for the transcription complex. Obviously the monoclonals are only useful for purification if they recognize native proteins in the enzyme complex. The results of the Radioimmunoprecipitation experiments may be used help to identify high affinity monoclonals that immunoprecipitate the entire transcription complex. An immunopurification protocol should greatly simplify the purification and analysis of the transcription complexes. The current protocol takes two weeks because the inventors test for activity after every column. This could probably be shortened to one week, but immunopurification would take only one or two days.

For immunopurification, antibodies are purified on protein A agarose, and crosslinked to CNBR-activated Sepharose (Harlow and Lane, 1988). Crude nuclear extracts or phosphocellulose column fractions are passed through an affinity column al a controlled rate of 2 ml/hr. The best elution conditions are then determined empirically. The inventors want to maintain functional activity and first try the more gentle conditions, such as mild acid or base, high salt, or ethylene glycol. Elution of transcription activity is monitored using the C-free cassettes. Immunopurification is an extremely powerful technique; however, it is impossible to predict which monoclonals are useful for this purpose. The inventors expect that the development of an immunopurification protocol will take a large investment of time.

Example 14

Characterize Proteins Specifically Required for Late Gene Expression

The inventors are particularly interested in clarifying the functions of proteins that permit the transcription of the very late gene polyhedrin. The initial results indicate that this very late specific factor is in a complex with the viral RNA polymerase during the early stages of purification, but is lost from the final purified complex. Therefore, the inventors initially analyze the partially purified polymerase, specifically to look for different interactions between the complexes and the late and very late promoters. In these experiments, the inventors compare native 39k and polyhedrin promoters with the sequences used to generate the C-free cassettes. These experiments should help to determine whether the use of a C-free cassettes with mutated promoters was justified.

Promoter recognition. The inventors use a restriction fragment of the polyhedrin promoter corresponding to −92 to +1 of translation as a probe for protein binding experiments. Purified transcription complexes are incubated with the probes, and gel shift assays used to detect the formation of protein-DNA complexes (Fried and Crothers, 1981; Garner and Revzin, 1982). The inventors have synthesized oligonucleotides corresponding to the downstream activator region of the polyhedrin promoter, a 12 bp sequence surrounding the TAAG motif, and a larger fragment of the polyhedrin promoter containing this 12 bp sequence. These oligonucleotides are used as competitors of the −92 to +1 probe, and they are also labeled and analyzed directly as probes.

This fragment of the polyhedrin promoter is large enough to bind several proteins. Thus, the inventors use DNase I protection (Galas and Schmitz, 1978) or orthophenathroline-copper ion protection analysis (Kuwabara and Sigman, 1987) to provide sequence-specific information on the binding sites. In the lab, the inventors have used gel shift assays to document binding of IE1 to hr5 (Guarino and Dong, 1991, 1994) and DNase I footprinting to identify residues in hr5 that are protected by IE1. The copper ion protection assays give more detailed information than DNase I when multiple components are utilized. The inventors compare the protection patterns obtained with the late and very late transcription complexes.

For the 39k promoter, the inventors initially use a restriction fragment corresponding to −92 to +9 for gel retardation analyses (Guarino and Smith, 1992). The inventors previously conducted a linker scan of the 39k promoter through this entire region, and the inventors have several oligonucleotides that can be used as competitors or as probes for further mapping. DNase I and copper ion protection experiments are performed as discussed for polyhedrin.

These experiments with the purified transcription complexes may permit quantitation of identify differences in binding activities, but do not permit the identification of the proteins that are responsible for this activity. Thus, the inventors may also attempt to purify the very late stimulatory factor in order to study the individual subunits. This is done using the standard in vitro transcription assay containing both promoters to assay for factors that specifically stimulate polh transcription and not 39k.

Example 15

VLF-1 Characterization

As a complementary approach, the inventors wanted to characterize VLF-1 (a protein believed to be responsible for the shift from late to very late gene expression in vivo. When VLF-1 was originally described, a similarity with the integrase family of tyrosine recombinases was noted (Esposito et al., 1997; Nunes-Duby et al., 1998). Members of the integrase family catalyze DNA transposition and insertion of viral genomes into host chromosomes. Other tyrosine recombinases are essential for resolution of bacterial or plasmid dimers formed during replication. All integrases and tyrosine recombinases are characterized by an essential active site tyrosine which forms a covalent protein-DNA intermediate used to catalyze the reaction.

To test whether VLF-1 was active in a purified in vitro transcription system, it was expressed in both bacteria and baculovirus-infected cells, and purified to homogeneity by affinity chromatography, followed by ion exchange chromatography con Mono S, and filtration through a Superdex-200 size exclusion column. Then titrated amounts of VLF-1 were added to purified RNA pol and the two transcription templates, one containing a C-free cassette linked to the late 39k and another with the same cassette linked to the very late polh promoter. This permits quantiation of template preference under competitive conditions.

Addition of VLF-1 from either bacterial or baculovirus sources resulted in a concentration-dependent increase in transcription from the polyhedrin promoter (FIG. 33). This is the pattern expected for the protein involved in switching from late to very late gene expression, as one type of promoter has to be activated while the other type has to be repressed.

A complementary approach would be to express selected proteins in an overexpression system, such as bacteria (Rosenberg et al., 1987), vaccinia virus (Elroy-Stein and Moss, 1990) or the baculovirus expression system (O'Reilly et al., 1992). The best system for expressing each protein must be determined empirically. The inventors have considerable experience with bacterial and baculoviral expression systems, and do not anticipate problems with the techniques. The inventors have relatively little experience with vaccinia expression systems, although I have done some work on vaccinia in the past (Hruby et al., 1979). Most likely, the inventors use a combination of all of these approaches to fully characterize the most interesting proteins.

The inventors identified two fractions containing additional transcription factors: the flow-through of the phosphocellulose column, and the factor that permits transcription of linear templates. It is possible that these factors are also DNA binding proteins. Therefore, the inventors analyze the DNA binding activity of these factors as described above. These experiments are performed first with purified proteins, and then an attempt to develop an overexpression system for further analysis is done.

Example 16

Stably Transformed Cells

The ultimate goal of the research program is to identify all of the viral proteins required for transcription of polyhedrin. The practical application of this knowledge would be to improve the efficiency of the baculovirus expression vector system (BEVS). This system is widely used for expression of foreign genes in a eukaryotic system. One limitation of BEVS is that, but is limited in two respects. One, expression requires infection of insect cells with virus. Because infection kills the cells, expression is transient and, therefore, the usefulness of the system is limited. Transient expression is acceptable for research applications, but it is unfavorable for commercial applications. Another problem with BEVS is that, post-translational processing of foreign genes is often incomplete during the late stages of viral infection (Jarvis and Summers, 1989). Presumably this reflects the fact that some protein processing pathways (e.g., for protein glycosylation and secretion), which are not used by viral proteins during this time, are no longer functioning.

One way to overcome these limitations is to design replicating baculovirus vectors that contain only the viral genes required for optimal transcription from the polyhedrin promoter or to produce insect cell lines that stably express these genes. All other viral factors, particularly those that induce cytopathic effects, would be deleted from these vectors or cell lines. The inventors previously used the ie1 promoter of AcNPV to produce insect cells that continuously express tissue plasminogen activator (TPA), a complex human glycoprotein (Jarvis et al., 1990). IE1 is an early promoter that is transcribed by the host RNA polymerase. *S. frugiperda* cells were transformed with two plasmids, one containing a neomycin-resistance gene and the other containing TPA, both under the control of the ie1 promoter. Neomycin-resistant clones were isolated and assayed for expression of the second gene. As expected, the level of TPA was less than that obtained under polyhedrin control. However, the transformed cells expressed TPA continuously, and processed TPA more efficiently that infected cells.

A similar strategy could be used to produce a cell line that stably expressed the fours subunits of RNA polymerase, and possibly one or more accessory proteins, under ie1 control. Then a heterologous gene could be stably added under polyhedrin control. This would be an improvement on the ie1 promoter because the levels of expression would be much greater due to the polyhedrin promoter.

Example 17

Transcription Stimulation by LEF-5

The baculovirus protein LEF-5 has homology to the eukaryotic transcription elongation factor TFIIS. Therefore, the inventors wanted to test the ability of LEF-5 to increase the transcriptional activity of baculovirus RNA polymerase.

The entire lef-5 open reading frame (ORF) was subcloned into the IMPACT expression vector pCYB1 (New England Biolabs). The advantage of this system is that it produces fusion proteins with a self-cleavable intein tag. The tag can be cleaved after affinity purification resulting in a protein that is identical to the wildtype protein with no additional or substituted amino acids. The LEF-5-intein fusion protein was expressed in soluble form and bound to a 1.5 ml chitin column. Contaminating proteins were removed by washing the column and LEF-5 was cleaved and eluted with 30 mM DTT. Fractions containing LEF-5 were pooled and dialyzed against 150 mM NaCl buffer and subsequently loaded onto a single-stranded DNA agarose column. LEF-5 bound to ssDNA and was eluted at 500 mM NaCl.

Purified LEF-5 was added to in vitro transcription assays containing 39 k and polh C-free cassettes and purified RNA polymerase. LEF-5 increased the level of transcription products in a concentration-dependent manner (FIG. 34). There was no difference in the amount of stimulation for the two templates. At a 4-fold molar excess of LEF-4/RNApol, the amount of product was 7.6 fold higher than in the absence of LEF-5. To confirm that the stimulation was due to LEF-5, and not to contaminants, the effect of adding mutant versions of LEF-5 in which the glu and/or asp residues in the QTRxxDE motif were mutated to alanine. This motif is essential for TFIIS function. None of the mutants were active in stimulation of transcription.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

REFERENCES CITED

Ayres, M. D., S. C. Howard, J. Kuzio, M. Lopez-Ferber, and R. D. Possee. 1994. The complete DNA sequence of Autographa californica nuclear polyhedrosis virus. Virology 202: 586–605.

Blissard, G. W. and G. F. Rohrmann. 1989. Location, sequence, transcriptional mapping, and temporal expression of the gp64 envelope glycoprotein gene of the Orygia pseudotsugata multicapsid nuclear polyhedrosis virus. Virology 170: 527–555.

Burgess, R. R. 1996. Purification of overproduced *Escherichia coli* RNA polymerase sigma factors by solubilizing inclusion bodies and refolding from sarkosyl. Methods Enzymol. 273: 145–149.

Cong, P., and S. Shuman. 1993. Covalent catalysis in nucleotidy transfer: a KTDG motif essential for enzyme-GMP complex formation by mRNA capping enzyme is conserved at the active sites of RNA and DNA ligases. J. Biol. Chem. 268: 7256–7260.

Dantonel, J. W., R. Wall, and R. J. Rushinski. 1997. CPSF links transcription and mRNA 3' end formation. Nature 389: 399–402.

Esposito, D. and Scocca, J. J. 1997. The integrase family of tyrosine recombinases-evolution of a conserved active site domain. Nucl. Acids Res. 25:3605–3614.

Fujita, N. and A. Ishihama. 1996. Reconstitution of RNA polymerase. Methods Enzymol. 273: 121–130.

Gallie, D. R. 1991 The cap and poly(A) tail function synergistically to regulate mRNA translation efficiency. Genes.Dev. 5:2108–2116.

Gebauer, D., F. V. Corona, P. Becker, M. W. Hentze. 1998. A cell-free system from multicellular eukaryotes that recapitulates the in vivo functions of the cap and poly(A) structures of mRNA. Patent abstract.

Guarino, L. A. and M. W. Smith. 1992. Regulation of delayed-early gene transcription of dual TATA boxes. J. Virol. 66: 3722–3739.

Guarino, L. A., B. Xu, J. Jin, and W. Dong. 1998a. A viral-encoded RNA polymerase purified from baculovirus infected cells. J. Virol. 72:7985–7991.

Guarino, L. A., J. Jin, and W. Dong. 1998b. Guanylyltransferase activity of the LEF-4 subunit of baculovirus RNA polymerase. J. Virol 72: 10003–10010.

Hagervorst, F. B. L. 1997. The Protein Truncation Test. Promega Notes Magazine. 62: 7–9.

Iizuka, N., L. Najita, A. Franzusoff, and P. Sarnow. 1994. Cap-dependent and cap-independent translation by internal initiation of mRNAs in cell exracts prepared from *Saccharomyces cerevisiae*. 14: 7322–7330.

Jackson, R. J. and N. Standart. (1990). Do the poly(A) tail and 3' untranslated region control mRNA translation? Cell 62: 15–18.

Jin, J., W. Dong, and L. Guarino. 1998. The LEF-4 subunit of baculovirus RNA polymerase has 5'-RNA triphosphatase and ATPase activities. J. Virol. 72: 10011–10019.

Li. S., M. Brisson, Y. He, and L. Huang. Delivery of a PCR amplified DNA fragment into cells: a model for using synthetic genes for gene therapy.

McCracken, S., N. Fong, K. Yankulov, S. Ballantyne, G. Pan, J. Greenblatt, S. D. Patterson, M. Wickens, and D. L. Bentley. 1997a. The C-terminal domain of RNA polymerase II couples mRNA processing to transcription. Nature 385: 357–361.

McCracken, S., N. Fong, E. Rosonina, K. Yankulov, G. Brothers, D. Siderovski, A. Hessel, S. Foster, Amgen EST Program, S. Shuman, and D. L. Bentley. 199b. 5'-Capping enzymes are targeted to pre-mRNA by binding to the phosphorylated carboxy-terminal domain of RNA polymerase II. Genes & Dev. 11: 3306–3318.

Miller, L. K., ed. 1997. The baculoviruses. Plenum Press, New York.

Mizuguchi, H., T. Nakagawa, Y. Morioka, S. Imazu, M. Nakanishi, T. Kondo, T. Hayakawa, T. Mayumi. 1997. Cytoplasmic gene expression system enhances the efficiency of cationic liposome-mediated in vivo gene transfer into mouse brain. Biochem. Biophys. Res. Comm. 234: 15–18.

Niles, E. G., and L. Christen. 1993. Identification of the vaccinia virus mRNA guanylyl-transferase active site lysine. J. Biol. Chem. 268: 24968–24989.

Nunes-Duby, S. E., Kwon, H. J., Tirumalai, R. S., Ellenberger, T., and Land, A. 1998. Similarities and differences among 105 members of the int family of site-specific recombinases. Nucl. Acids Res. 26:391–406.

O'Reilly, D. R., L. K. Miller, and V. A. Luckow. 1992. Baculovirus expression vectors: a laboratory manual. W.H. Freeman & Co., New York.

Pasquinelli, A. E., J. E. Dahlberg, and E. Lund. 1995. Reverse 5' caps in RNAs made in vitro by phage RNA polymerases. RNA 1: 957–967.

Passarelli, A. L., J. W. Todd, and L. K. Miller. 1994. A baculovirus gene involved in late gene expression predicts a large polypeptide with a conserved motif of RNA polymerases. J. Virol. 68: 4673–4678.

Platt, T. 1986. Transcription termination and the regulation of gene expression. Annu. Rev. Biochem. 55: 339–372.

Possee, R. D., and S. C. Howard. 1987. Analysis of the polyhedrin gene promoter of the *Autographa californica* nuclear polyhedrosis virus. Nucl. Acids. Res. 15: 10233–10237.

Rankin, C. B., B. G. Ooi and L. K. Miller. 1988. Eight base pairs encompassing the transcriptional start point are the major determinant for baculovirus polyhedrin expression. Gene 70: 39–49.

Roest PAM, Roberts R G, Sugino S, Van Ommen G J B, Den Dunnen J T. 1993. Protein truncation test (PTT) for rapid detection of translation-terminating mutations. Hum Mol Genet 2: 1719–21.

Rohrmann, G. F. 1986. Polyhedrin structure. J. Gen. Virol. 67: 1499–1508.

Schneider, A. R. W. P. Smith, A. R. Kautz, K. Weisshart, F. Grosse, and H. P. Nasheuer. 1998. Primase activity of human DNA polymerase a-primase. J. Biol. Chem. 273: 21608–21615.

Todd, J. W., Passarelli, A. L., and Miller, L. K. 1995. Eighteen baculovirus genes, including lef-11, p35, 39k and p47, support late gene expression. J. Virol. 69: 968–974.

Wang, S. P., L. Deng, C. K. Ho, and S. Shuman. 1997. Phylogeny of mRNA capping enzymes. Proc. Natl. Acad. Sci., USA 94: 9573–9578.

Westwood, J. A., I. M. Jones, and D. H. L. Bishop. 1993. Analyses of Alternative poly(A) signals for use in baculovirus expression vector. Virology 195: 90–99.

Xu, B., Yoo, S., and Guarino, L. A. 1995. Differential transcription of baculovirus late and very late promoters, fractionation of nuclear extracts by phosphocellulose. J. Virol. 69: 2912–2917.

Yu, L., A. Martins, L. Deng, S. Shuman. 1997. Structure-function analysis of the triphosphatase component of vaccinia virus mRNA capping enzyme. J. Virol. 71:9837–9843.

Yuen, L. and B. Moss. 1987. Oligonucleotide sequence signaling transcriptional termination of vaccinia virus early genes. Proc. Natl. Acad. Sci., USA 84: 6417–6421.

Guarino, L. A. 1990. Identification of a viral gene encoding a ubiquitin-like protein. Proc. Natl. Acad. Sci., USA 87:409–413.

Jarvis, D. L., J. G. W. Fleming, G. R. Kovacs, M. D. Summers, and L. A. Guarino. 1990. Constitutive expression of a foreign gene product in stably-transformed Lepidopteran insect cells using early baculovirus promoters. Bio/Technology 8:950–955.

Guarino, L. A., and M. W. Smith. 1990. Nucleotide sequence of the 39K gene region of *Autographa californica* nuclear polyhedrosis virus. Virology 179:1–8.

Carson, D. D., M. D. Summers, and L. A. Guarino. 1991a. Transient expression of the AcMNPV immediate early gene IEN is regulated by three viral elements. Virol. 65:945–951.

Carson, D. D., M. D. Summers, and L. A. Guarino. 1991b. Molecular analysis of a baculovirus, regulatory gene. Virology 182:279–286.

Guarino, L. A., and W. Dong. 1991. Expression of an enhancer-binding protein in insect cells transfected with the AcNPV IE1 gene. J. Virol. 65:3676–3680.

Kovacs, G. R., J. Choi, L. A. Guarino and M. D. Summers. 1992. Functional dissection of the *Autographa californica* nuclear polyhedrosis virus immediate early-1 transcriptional regulatory protein. J. Virol. 65:7429–7437.

Guarino, L. A., W. Dong, B. Xu, D. R. Broussard, R. W. Davis, and D. L. Jarvis. 1992. The baculovirus phosphoprotein pp31 is associated with the virogenic stroma. J. Virol. 66:7113–7120.

Yoo, S., and L. A. Guarino. 1994a. Functional dissection of the *Autographa californica* nuclear polyhedrosis virus ie2 gene product. Virology 202:164–172.

Yoo, S., and L. A. Guarino. 1994b. The *Autographa californica* nuclear polyhedrosis virus ie2 gene encodes a transcriptional regulator. Virology 202:746–753.

What is claimed is:

1. A method of capping and polyadenylation RNA transcripts comprising the steps of:
   producing an RNA transcript using baculovirus RNA polymerase, wherein the baculovirus RNA polymerase caps and polyadenylates the RNA transcript.

2. The method of claim 1, wherein producing comprises use of an expression vector comprising a promoter sequence, a polynucleotide sequence and a baculovirus terminator sequence.

3. The method of claim 2, wherein said promoter sequence comprises a baculovirus consensus sequence.

4. The method of claim 3, wherein said consensus sequence is TAAG.

5. The method of claim 2, wherein said promoter sequence is a functional equivalent of the baculovirus consensus sequence.

6. The method of claim 1 further comprising enhancing the production of the RNA transcript by adding an accessory protein.

7. The method of claim 6, wherein said accessory protein is LEF-5 or VLF-1.

8. The method of claim 6, wherein said accessory protein is a viral methyltransferase.

9. The method of claim 1 further comprising more than one accessory protein.

10. The method of claim 2, wherein said expression vector is prokaryotic or eukaryotic.

11. The method of claim 1, wherein said method is performed in a cell.

12. The method of claim 11, wherein said cell is prokaryotic or eukaryotic.

13. The method of claim 1, wherein said method is performed in a cell-free system.

14. The method of claim 1, wherein said method is performed in vivo.

15. The method of claim 1, wherein said polymerase is a four subunit complex.

16. The method of claim 15, wherein said subunit complex comprises LEF-8, LEF-4, LEF-9 and p47.

17. The method of claim 16, wherein LEF-4 subunit mediates capping.

18. The method of claim 1, wherein said polymerase terminates after a T-rich region in the transcript.

19. A method of capping RNA transcripts comprising the steps of:
   producing an RNA transcript in vitro using baculovirus RNA polymerase, wherein the baculovirus RNA polymerase caps the RNA transcript.

20. The method of claim 19, wherein said polymerase is a four subunit complex.

21. The method of claim 20, wherein said subunit complex comprises LEF-8, LEF-4, LEF-9 and p47.

22. The method of claim 21, wherein LEF-4 subunit mediates capping.

23. A method of polyadenylating RNA transcripts comprising the steps of:
   producing an RNA transcript in vitro using baculovirus RNA polymerase, wherein the baculovirus RNA polymerase polyadenylates the RNA transcript.

24. The method of claim 23, wherein said polymerase terminates after a T-rich region in the transcript.

* * * * *